US012636366B2

(12) United States Patent
Gasser et al.

(10) Patent No.: US 12,636,366 B2
(45) Date of Patent: May 26, 2026

(54) RUTHENIUM (II) COMPLEXES AND CONJUGATES THEREOF FOR USE AS PHOTOSENSITIZER AGENT IN PHOTODYNAMIC THERAPY

(71) Applicants: Paris Sciences et Lettres, Paris (FR); Ecole Nationale Superieure de Chimie de Paris, Paris (FR); University of Zürich, Zurich (CH)

(72) Inventors: Gilles Albert Gasser, Paris (FR); Franz Heinemann, Erlenbach (DE); Malay Patra, Mumbai (IN); Marta Jakubaszek, Dlugopole Zdroj (PL); Chloe Subecz, Arceuil (FR); Johannes Karges, Eichenzell (DE)

(73) Assignees: Ecole Nationale Superieure de Chimie de Paris, Paris (FR); University of Zürich, Zurich (CH)

( * ) Notice: Subject to any disclaimer, the term of this patent is extended or adjusted under 35 U.S.C. 154(b) by 1104 days.

(21) Appl. No.: 17/619,324

(22) PCT Filed: Jun. 24, 2020

(86) PCT No.: PCT/EP2020/067757

§ 371 (c)(1),
(2) Date: Dec. 15, 2021

(87) PCT Pub. No.: WO2020/260424

PCT Pub. Date: Dec. 30, 2020

(65) Prior Publication Data

US 2022/0296711 A1 Sep. 22, 2022

(30) Foreign Application Priority Data

Jun. 24, 2019 (EP) .................................... 19305828

(51) Int. Cl.

| | |
|---|---|
| ***A61K 41/00*** | (2020.01) |
| ***A61K 47/64*** | (2017.01) |
| ***A61P 17/00*** | (2006.01) |
| ***A61P 17/10*** | (2006.01) |
| ***A61P 31/00*** | (2006.01) |
| ***A61P 31/04*** | (2006.01) |
| ***A61P 31/12*** | (2006.01) |
| ***A61P 35/00*** | (2006.01) |

(Continued)

(52) U.S. Cl.

CPC ........ *A61K 41/0057* (2013.01); *A61K 47/643* (2017.08); *A61P 17/00* (2018.01); *A61P 17/10* (2018.01); *A61P 31/00* (2018.01); *A61P 31/04* (2018.01); *A61P 31/12* (2018.01); *A61P 35/00* (2018.01); *C07D 401/04* (2013.01); *C07D 401/14* (2013.01); *C07F 15/0053* (2013.01)

(58) Field of Classification Search

None

See application file for complete search history.

(56) References Cited

U.S. PATENT DOCUMENTS

2010/0216993 A1* 8/2010 Mei ..................... C07F 15/0053 546/2
2015/0303063 A1* 10/2015 Tada ......................... C07F 7/02 556/136
2018/0334473 A1* 11/2018 Mei ..................... C07F 15/0046

FOREIGN PATENT DOCUMENTS

CN 109053809 A 12/2018
CN 109233547 A 1/2019
CN 109535066 A 3/2019

OTHER PUBLICATIONS

Monro et al. "Transition Metal Complexes and Photodynamic Therapy from a Tumor-Centered Approach: Challenges, Opportunities, and Highlights from the Development of TLD1433", Chem. Rev. 2019, 119, 797-828.

(Continued)

*Primary Examiner* — Sin J Lee

(74) *Attorney, Agent, or Firm* — Banner & Witcoff, Ltd.

(57) ABSTRACT

The present invention relates to a compound of the following formula (I):

(I)

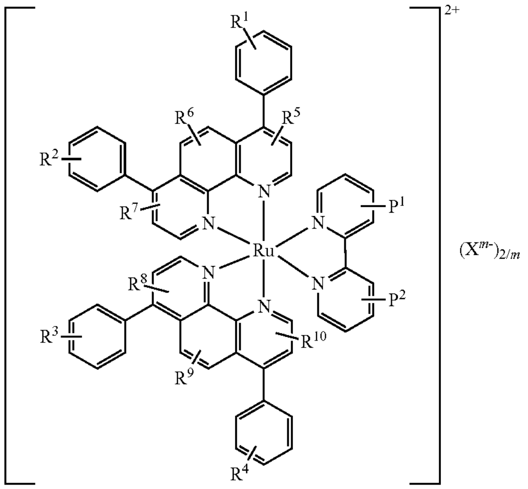

or a pharmaceutically acceptable salt and/or solvate thereof, for use as photosensitizer agent in photodynamic therapy.

The present invention relates also to a pharmaceutical composition comprising such a compound and at least one pharmaceutically acceptable excipient.

The present invention relates also to a conjugate comprising such a compound linked to a biomolecule such as a peptide, a protein, an aptamer, an affibody, an antibody or an antigen binding fragment thereof.

3 Claims, 2 Drawing Sheets

(51) Int. Cl.
*C07D 401/04* (2006.01)
*C07D 401/14* (2006.01)
*C07F 15/00* (2006.01)

(56) References Cited

OTHER PUBLICATIONS

Heinemann et al. "Critical Overview of the Use of Ru(II) Polypyridyl Complexes as Photosensitizers in One-Photon and Two-Photon Photodynamic Therapy" Acc. Chem. Res. 2017, 50, 2727-2736.
Poynton et al. "The development of ruthenium(II) polypyridyl complexes and conjugates for in vitro cellular and in vivo applications" Chem. Soc. Rev. 2017, 46, 7706-7756.
Shi et al. "Ru(II) dyads derived from ?-oligothiophenes: A new class of potent and versatile photosensitizers for PDT", Coord. Chem. Rev. 2014, 282-283, 127-138.
Sullivan et al. "Mixed Phosphine 2,2/-Bipyridine Complexes of Ruthenium", Inorg. Chem. 1978, 17 (12), 3334-3341.
Duong et al. "Syntheses and Structures of Isomeric Diaminotriazinyl-Substituted 2,20-Bipyridines and 1,10-Phenanthrolines" The Journal of organic chemistry 2011, 76 (5), 1333-1341.
Maury et al. "Design and synthesis of 4,40-p-conjugated[2,20]-bipyridines: a versatile class of tunable chromophores and -- fluorophores --" New J. Chem. 2001, 25 (12), 1553-1566.
Mari et al. "Combination of Ru(II) complexes and light: new frontiers in cancer therapy" J. Inorg. Chem. 2015, 2015 (23), 3879-3891.
Crosby et al. "Excited States of Mixed Ligand Chelates of Ruthenium (II) and Thodium (III)1" The Journal of Physical Chemistry 1976, 80 (20), 2206-2211.
Jones et al. "Photochemistry of Hetero-Tris-Chelated Ruthenium(II) Polypyridine Complexes in Dichloromethane" Inorg. Chem. 1989, 28 (12), 2281-2285.
Nakamaru, K., "Solvent Effect on the Nonradiative Deactivation of the Excited State of Tris (2,2'-bipyridyl)ruthenium (II) Ion". Bull. Chem. Soc. Jpn. 1982, 55 (5), 1639-1640.
Ishida et al. "Recent advances in instrumentation for absolute emission quantum yield Measurements", Coord. Chem. Rev. 2010, 254 (21-22), 2449-2458.
Nakamaru, K., "Synthesis, Luminiscence Quantum Yields, and Lifetimes of Trischelated Ruthenium(II) Mixed-ligand Complexes Including 3,3'-Dimethyl-2,2'-bipyridyl" Bull. Chem. Soc. Jpn. 1982, 55 (9), 2697-2705.
Lim et al. "Current state of immunotherapy for glioblastoma" Nature Reviews Clinical Oncology 2018, 15 (7), 422-442.
Lomzik et al. "New ruthenium compounds bearing semicarbazone 2-formylopyridine moiety: Playing with auxiliary ligands for tuning the mechanism of biological activity" Journal of Inorganic Biochemistry 2017, 175, 80-91.
Brennan et al. "Photonic and Electrochemical Propoerties of Absorbed [Ru9dpp)2(Qbpy)]2+ Luminophores" Langmuir, 2006, p. 10754-10761.
Pichler et al. "Maleimide-functionalised platinum(IV) complexes as a synthetic platform for targeted drug delivery" Chem. Commun. 2013, 49, p. 2249-2251.
Jan. 17, 2020 (EP) Extended European Search Report App. No. 19305828.6.
Nov. 9, 2020 (WO) International Search Report PCT/EP2020/067757.
Mazuryk et al. "Multifaceted interplay between lipophilicity, protein interaction and luminescence parameters of non-intercalative ruthenium (II) polypyridyl complexes controlling cellular imaging and cytotoxic properties", J Biol Inorg Chem, vol. 19, Aug. 26, 2014 (Aug. 26, 2014), pp. 1305-1316, XP002796687.
Mazuryk et al. "Nitroimidazole derivatives of polypyridyl ruthenium complexes: Towards understanding their anticancer activity and mode of action", European Journal of Pharmaceutical Sciences, Elsevier, Amsterdam, NL, vol. 101, Jan. 28, 2017, pp. 43-55, XP029953852.
Caspar et al. "A new family of Mono- and Dicarboxylic Ruthenium complexes . . . ", Inorganic Chemistry, vol. 45, No. 10, Apr. 14, 2006, 4071-4078 XP002796688.
Gosh et al. "Mixed-ligand complexes of ruthenium(II) containing new photoactive or electroactive ligands: synthesis, spectral characterization and DNA interactions". J Biol Inorg Chem (2005) 10: 496-508.

* cited by examiner

RUTHENIUM (II) COMPLEXES AND CONJUGATES THEREOF FOR USE AS PHOTOSENSITIZER AGENT IN PHOTODYNAMIC THERAPY

RELATED APPLICATIONS

This application is a National Stage Application under 35 U.S.C. 371 of expired PCT application PCT/EP2020/067757 designating the United States and filed Jun. 24, 2020; which claims the benefit of EP Application Serial No. 19305828.6 and filed Jun. 24, 2019, each of which are hereby incorporated by reference in their entireties.

FILED OF THE INVENTION

The present invention relates to ruthenium (II) complexes bearing polypyridyl ligands and conjugates thereof with a biomolecule such as a peptide, a protein, an aptamer, an antibody or an antigen binding fragment thereof, in particular for use as photosensitizer agent in photodynamic therapy. The present invention also relates to a method of preparation of ruthenium (II) complexes bearing polypyridyl ligands.

BACKGROUND OF THE INVENTION

Photodynamic Therapy (PDT) is a non-invasive medical technique for the treatment of various types of cancer (i.e. lung, bladder, oesophageal and brain cancer) as well as bacterial, fungal or viral infections. The effect of PDT relies on the combination of an ideally non-toxic molecule, so called photosensitizer (PS), oxygen and light.

Photofrin is currently the most commonly used PS in PDT. It has been approved for the treatment of bladder cancer, early stage lung cancer, oesophageal cancer and early non-small cell lung cancer. However, based on its low solubility and low absorption at the therapeutic wavelengths, high concentrations as well as high light doses required for an adequate tumor treatment, Photofrin is not an ideal PS. Additionally, it was shown that the drug has an exceptionally long half-life excretion time, leading to severe photosensitivity for the patients. Since the majority of investigated and approved PS are based on a tetrapyrrolic scaffold (i.e. porphyrins, chlorins, phthalocyanines), these PSs are likely to have similar drawbacks that are 1) poor water solubility; 2) tedious synthesis and purification; 3) absorption in the spectral range of the biological environment (i.e. skin, fat, blood); 4) low cancer selectivity; 5) photobleaching effect and 6) slow clearance from the body causing photosensitivity.

New classes of PSs are thus being developed by the scientist. Among these new classes of PSs, the development of Ru(II) polypyridyl complexes as PDT PS is currently booming due to their ideal photophysical and photochemical properties (i.e. high water solubility, high chemical stability and photostability, intense luminescence, large Stokes shifts, high $^{1}O_2$ production) (McFarland, S. A. et al., 2019 and Gasser, G. et al., 2017). Nonetheless, despite these remarkable properties, the majority of Ru(II)-based PS suffer from a lack of absorption in the biological spectral window (600-900 nm). Based on absorption and light scattering effects in the biological environment, the light penetration depth into the tissue is low at this wavelength which limits their application to treat deep tumors.

To overcome this limitation, there is thus a need for optimization of the absorption properties of Ru(II)-based PSs. It has been well established that the photophysical properties including absorption, emission as well as excited state lifetimes of Ru(II) polypyridyl complexes are dependent from the bound ligand and therefore can be tuned (Gunnlaugsson, T. et al., 2017 and McFarland, S. A. et al., 2014).

SUMMARY OF THE INVENTION

The inventors have thus investigated ruthenium polypyridyl complexes with improved photophysical properties for use as photosensitizer agent in photodynamic therapy.

In a first aspect, the present invention thus relates to a compound of formula (I):

(I)

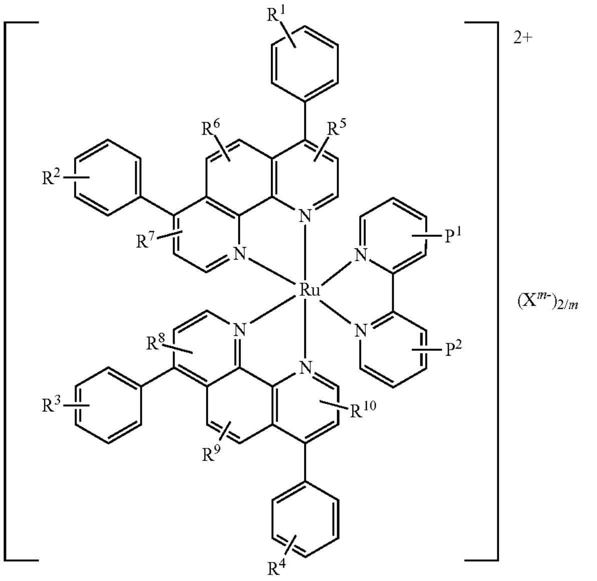

or a pharmaceutically acceptable salt and/or solvate thereof, wherein $R^1$ to $R^{10}$ each independently represent one or several substituents selected in the group consisting of H, halogen, optionally substituted $C_1$-$C_6$ alkyl, optionally substituted $C_2$-$C_6$ alkenyl, optionally substituted $C_2$-$C_6$ alkynyl, optionally substituted carbocycle, optionally substituted aryl, optionally substituted heteroaryl, optionally substituted heterocycle, CN, $NO_2$, $COR^{11}$, $OR^{12}$ and $NR^{13}R^{14}$, $R^{11}$ is selected in the group consisting of H, optionally substituted $C_1$-$C_6$ alkyl, $OR^{15}$ and $NR^{16}R^{17}$, $R^{12}$, $R^{13}$, $R^{14}$, $R^{15}$, $R^{16}$ and $R^{17}$ are each independently selected in the group consisting of H, optionally substituted $C_1$-$C_6$ alkyl and optionally substituted CO—($C_1$-$C_6$ alkyl), preferably H or $C_1$-$C_6$ alkyl, $P^1$ and $P^2$ each independently represent one or several substituents selected in the group consisting of H, halogen, optionally substituted $C_1$-$C_6$ alkyl, optionally substituted $C_2$-$C_6$ alkenyl, optionally substituted $C_2$-$C_6$ alkynyl, optionally substituted carbocycle, optionally substituted aryl, optionally substituted heteroaryl, optionally substituted heterocycle, CN, $NO_2$, $N_3$, $COR^{18}$, $OR^{19}$ and $NR^{20}R^{21}$, or $P^1$ and $P^2$ together with the pyridyl groups to which they are bonded represent:

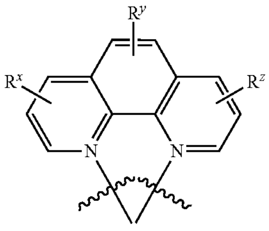 or 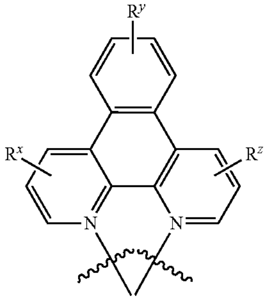

$R^x$, $R^y$ and $R^z$ each independently represent one or several substituents selected in the group consisting of H, halogen, optionally substituted $C_1$-$C_6$ alkyl, optionally substituted $C_2$-$C_6$ alkenyl, optionally substituted $C_2$-$C_6$ alkynyl, optionally substituted carbocycle, optionally substituted aryl, optionally substituted heteroaryl, optionally substituted heterocycle, CN, $NO_2$, $N_3$, $COR^{18}$, $OR^{19}$ and $NR^{20}R^{21}$, $R^{18}$ is selected in the group consisting of H, optionally substituted $C_1$-$C_6$ alkyl, $OR^{22}$ and $NR^{23}R^{24}$, $R^{19}$, $R^{20}$, $R^{21}$, $R^{22}$, $R^{23}$ and $R^{24}$ are each independently selected in the group consisting of H, optionally substituted $C_1$-$C_6$ alkyl and optionally substituted CO—($C_1$-$C_6$ alkyl), preferably H or $C_1$-$C_6$ alkyl, $X^{m-}$ is a pharmaceutically acceptable anion, preferably selected in the group consisting of $PF_6^-$, $Cl^-$, $Br^-$, $I^-$, $BF_4^-$, ($C_1$-$C_6$ alkyl)-C(O)$O^-$, ($C_1$-$C_6$ haloalkyl)-C(O)$O^-$, ($C_1$-$C_6$ alkyl)-$SO_3^-$, ($C_1$-$C_6$-haloalkyl)-$SO_3^-$, $SO_4^{2-}$ and $PO_4^{3-}$, m is 1, 2 or 3, for use as photosensitizer agent in photodynamic therapy.

The present invention therefore also relates to the use of a compound of formula (I) or a pharmaceutically acceptable salt and/or solvate thereof for the manufacture of a drug intended to be used as a photosensitizer agent in photodynamic therapy.

The present invention also relates to the use of a compound of formula (I) or a pharmaceutically acceptable salt and/or solvate thereof as a photosensitizer agent in photodynamic therapy.

The present invention also concerns a method of treatment by photodynamic therapy comprising administering to an animal, in particular a mammal such as a human, in need thereof an effective amount of a compound of formula (I) or a pharmaceutically acceptable salt and/or solvate thereof as a photosensitizer agent.

In a second aspect, the present invention relates to a compound of formula (I) or a pharmaceutically acceptable salt and/or solvate thereof.

Preferably, said compound is not:

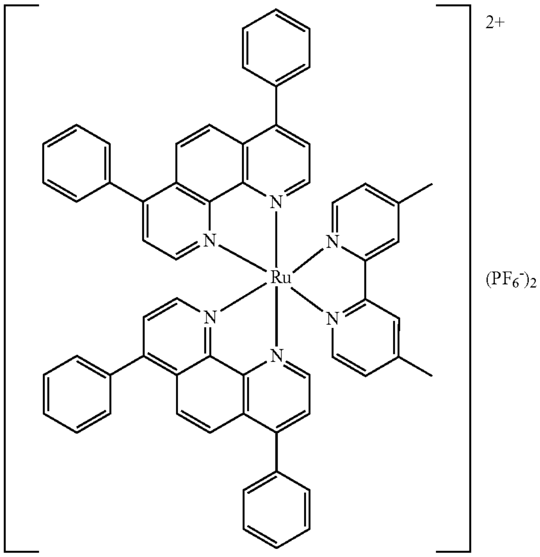

$(PF_6^-)_2$ and

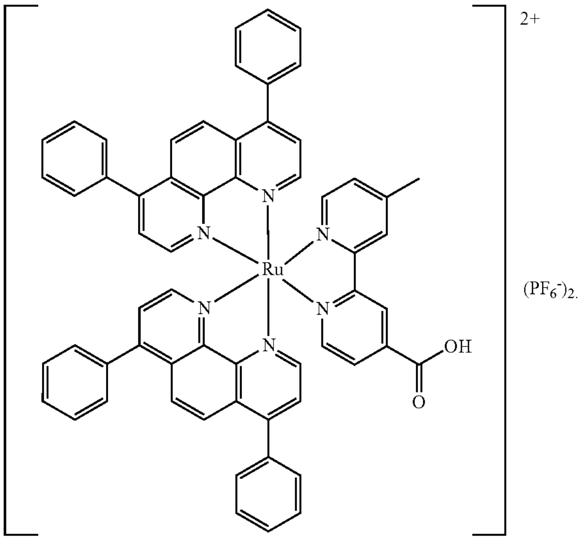

$(PF_6^-)_2$.

Preferably, said compound is also not:
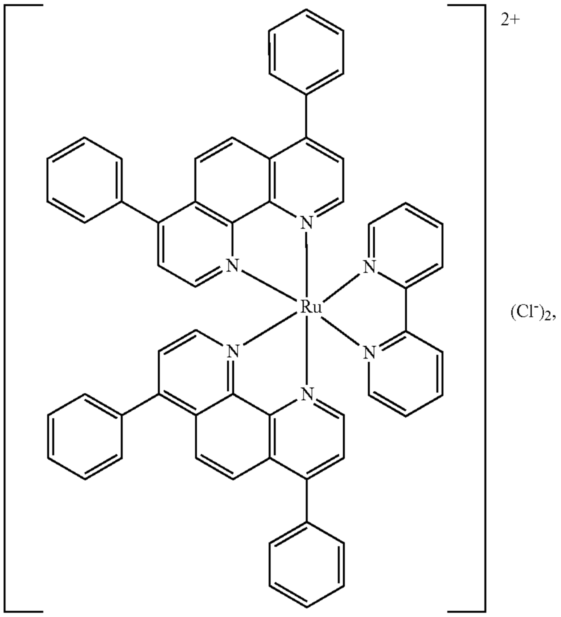
,
-continued
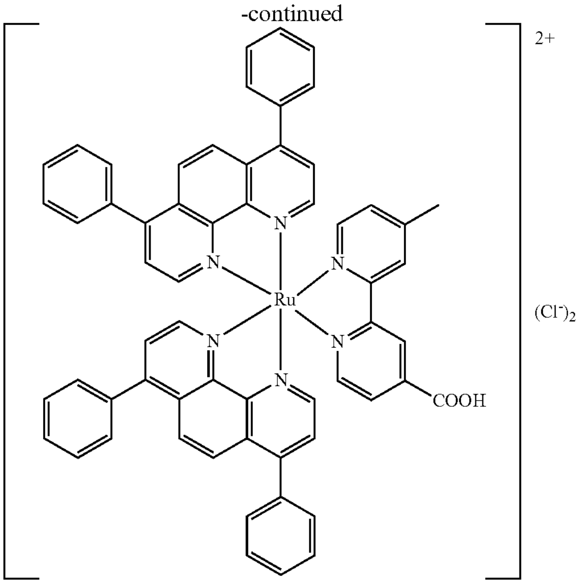
which are described in Mazuryk, O. et al., 2014.
Preferably, said compound of formula (I) is also not:
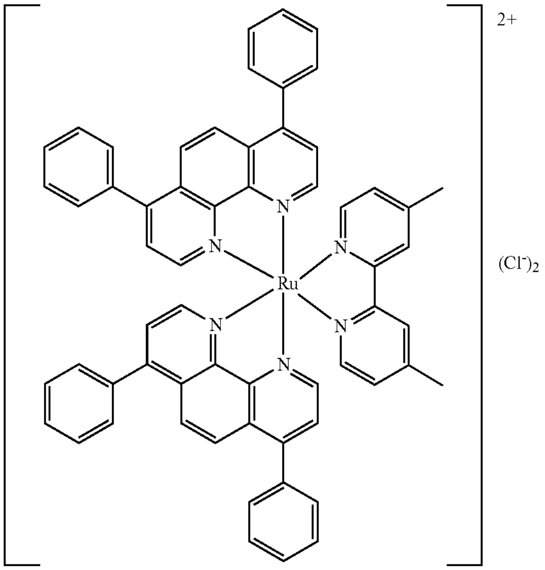
and
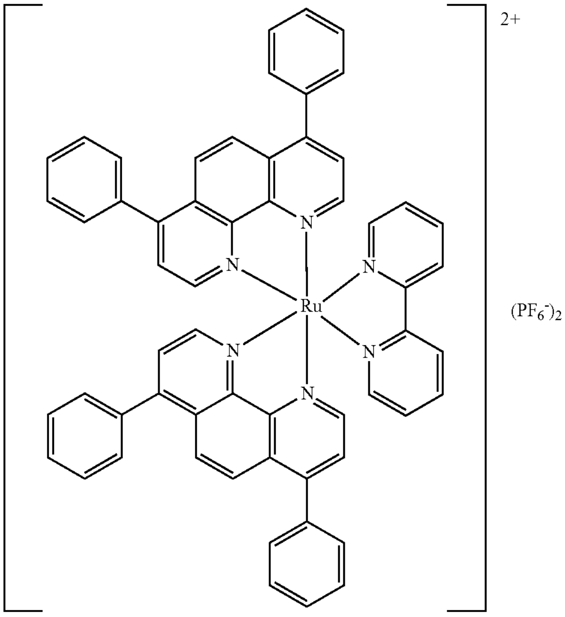
which is described in CN 109 535 066.

Preferably, said compound of formula (I) is also not:
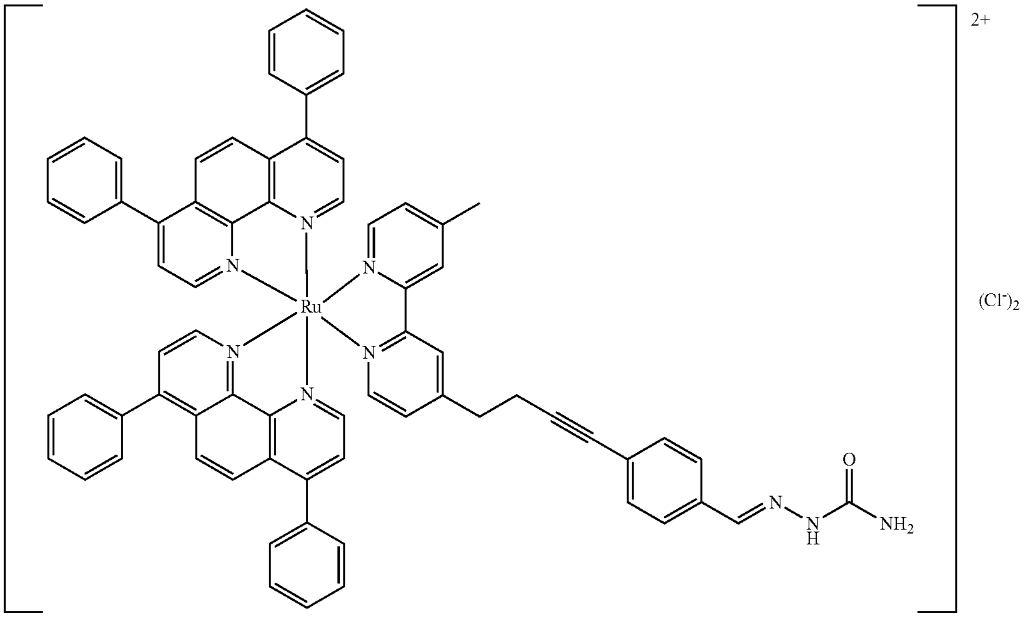
which is described in Lomzik, M. et al., 2017.
Preferably, said compound of formula (I) is also not:
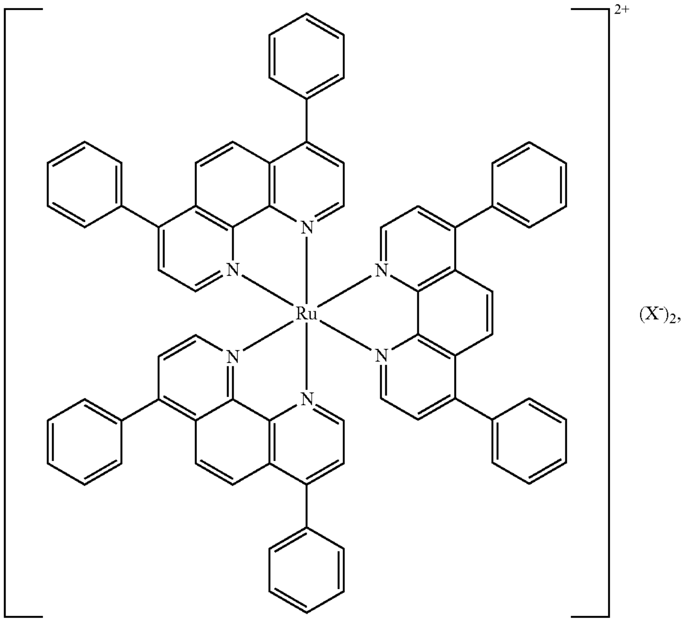

-continued
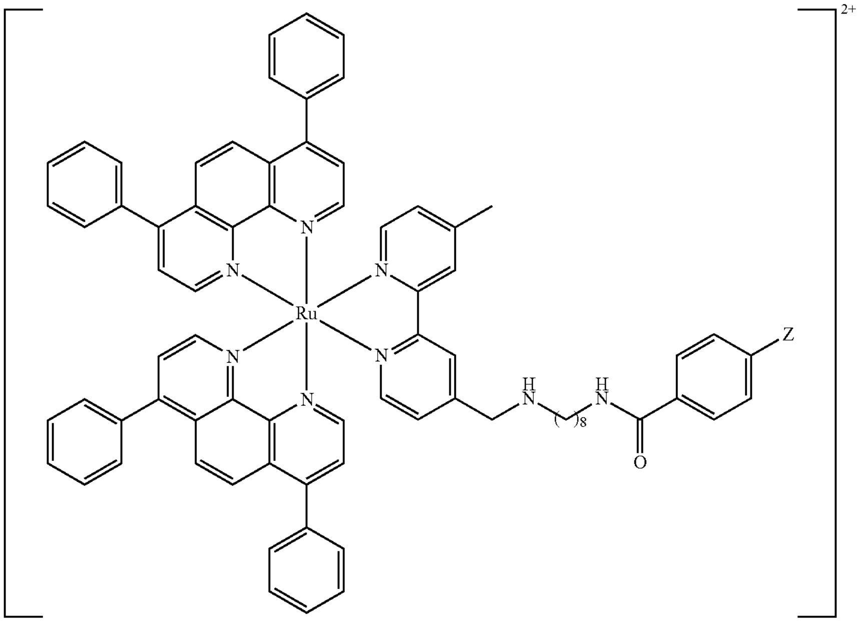
$(X^-)_2$ with
Z =
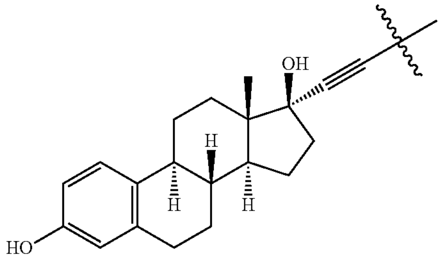
and
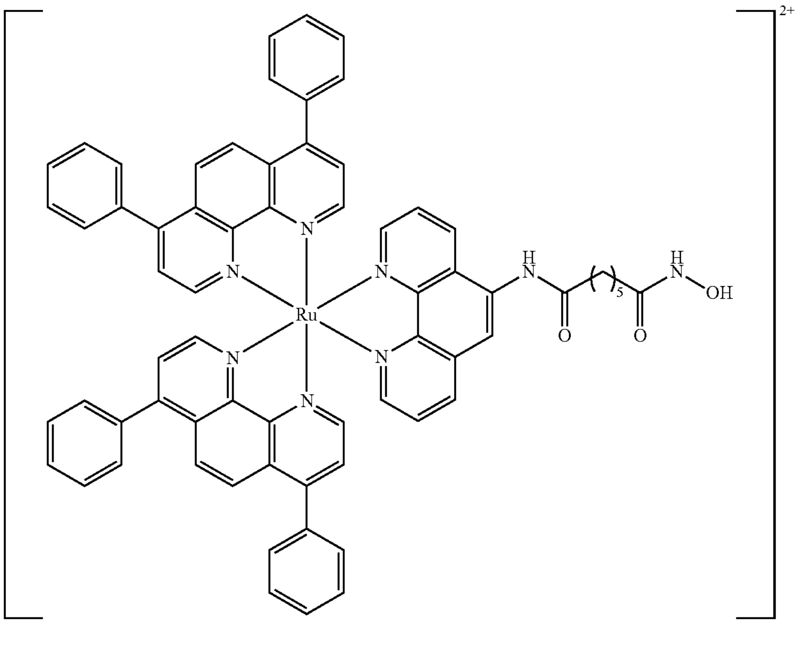
$(X^-)_2$
which is described in Poynton, F. et al., 2017.

Preferably, said compound of formula (I) is also not:
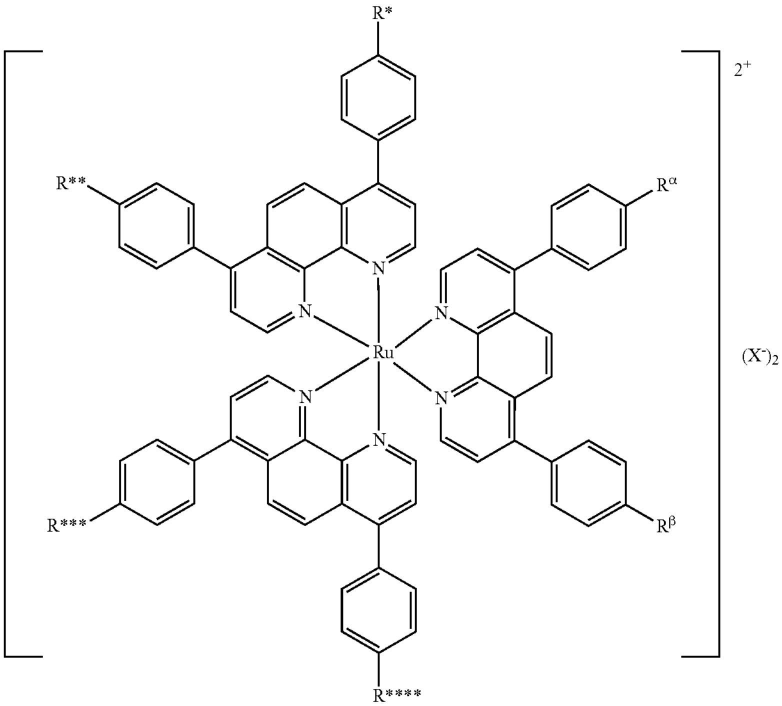
$(X^-)_2$ and
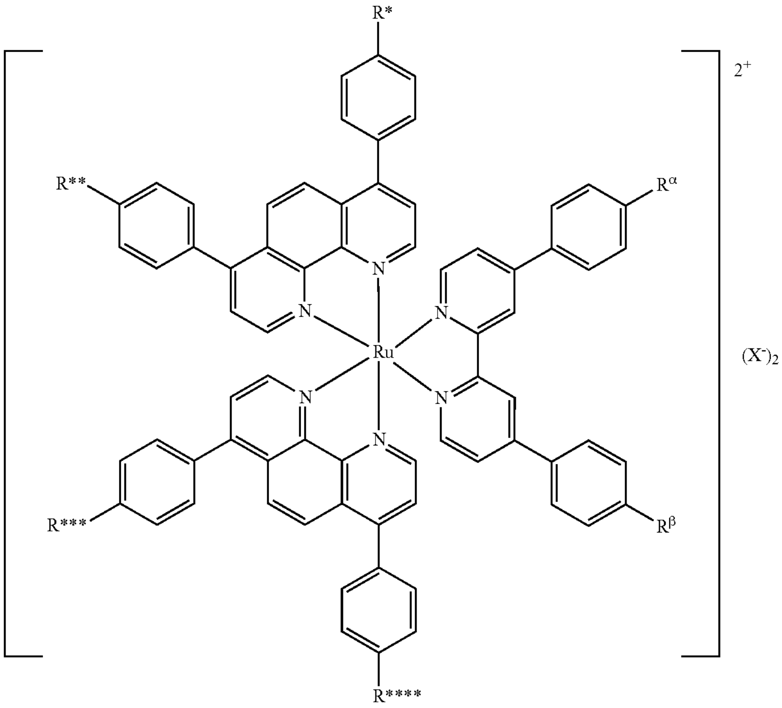
$(X^-)_2$
in which of $R^+$, $R^\beta$, R*, R, R* and R**** are each independently H, $CH_3$, COOH or $NH_2$, provided that at least one or two of $R^\alpha$ and $R^\beta$ is COOH or $NH_2$, said compounds being described in CN 109 233 547.

Preferably, said compound of formula (I) is also not:

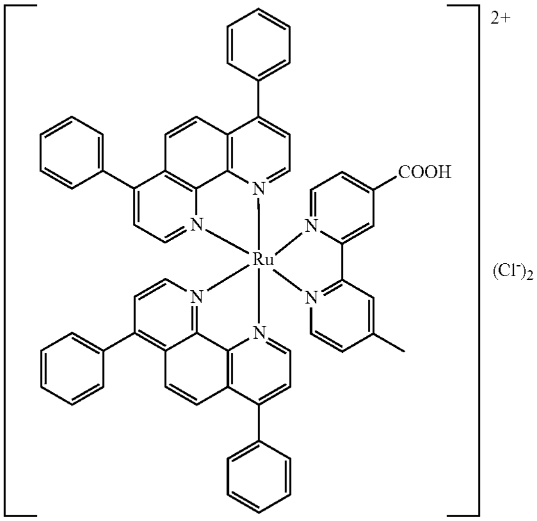

$(Cl^-)_2$ and

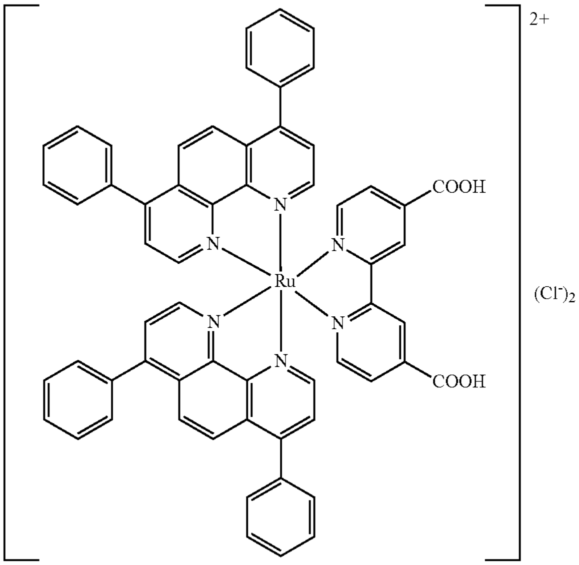

$(Cl^-)_2$ which are described in Caspar, R. et al., 2006.

Preferably, said compound of formula (I) is also not:

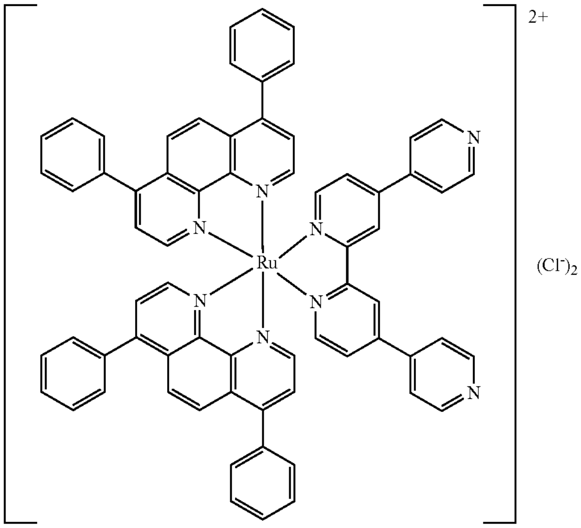

$(Cl^-)_2$ which is described in Brennan et al., 2006.

The present invention concerns a compound of formula (I) or a pharmaceutically acceptable salt and/or solvate thereof for use as a drug.

Preferably, said compound is not:

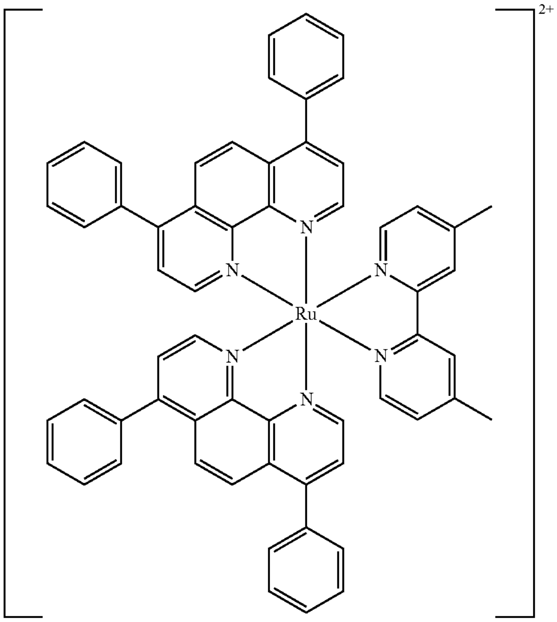

$(PF_6^-)_2$,

-continued
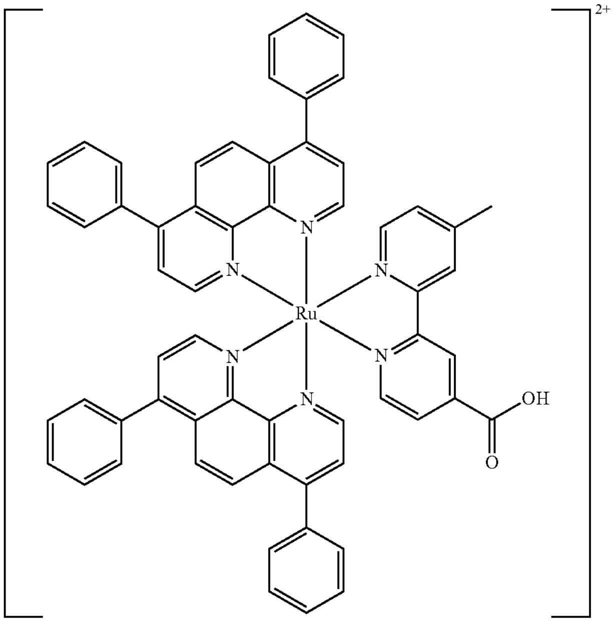
$(PF_6^-)_2$,
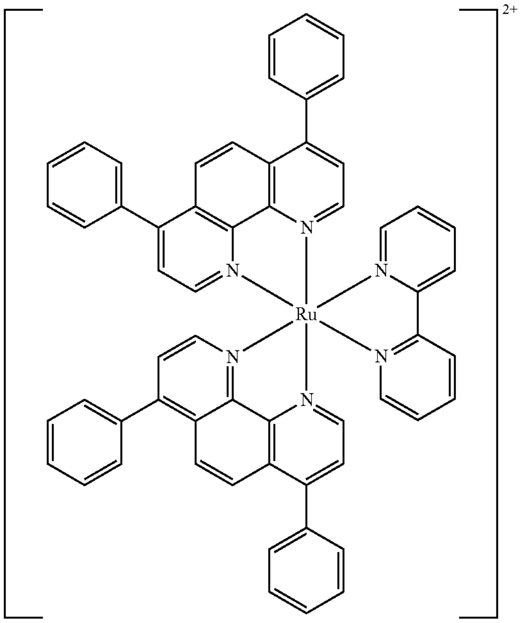
$(Cl^-)_2$,

-continued
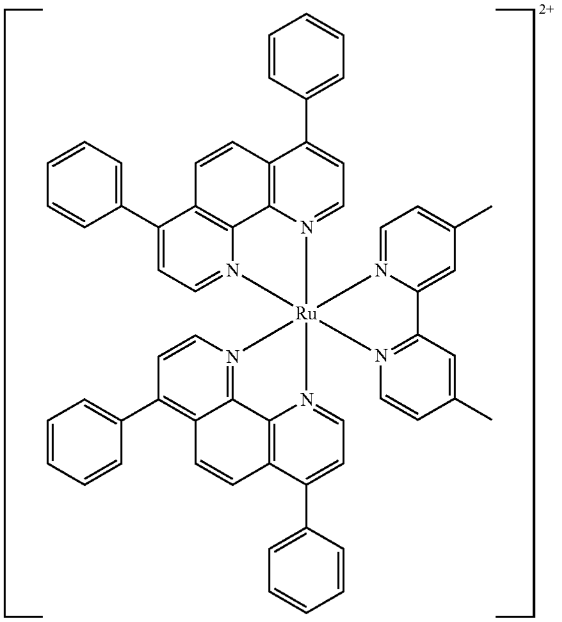
(Cl⁻)₂,
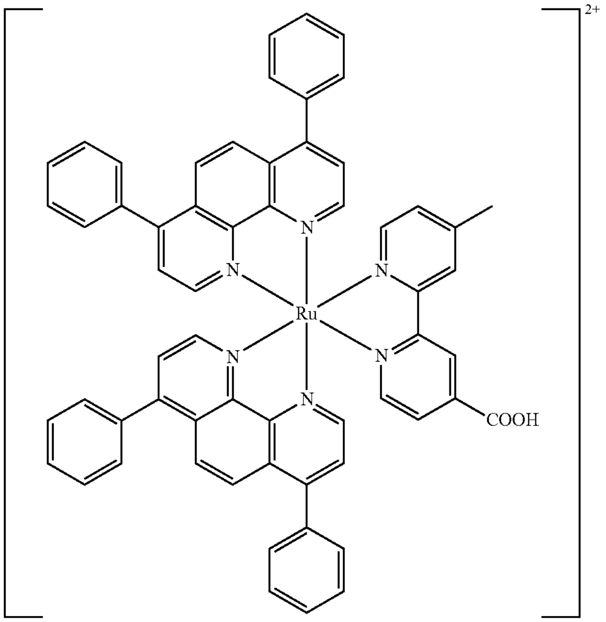
(Cl⁻)₂,

-continued
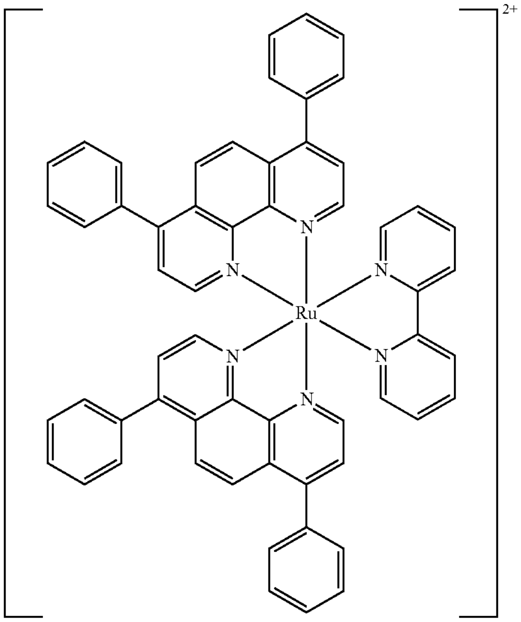
$(PF_6^-)_2$,
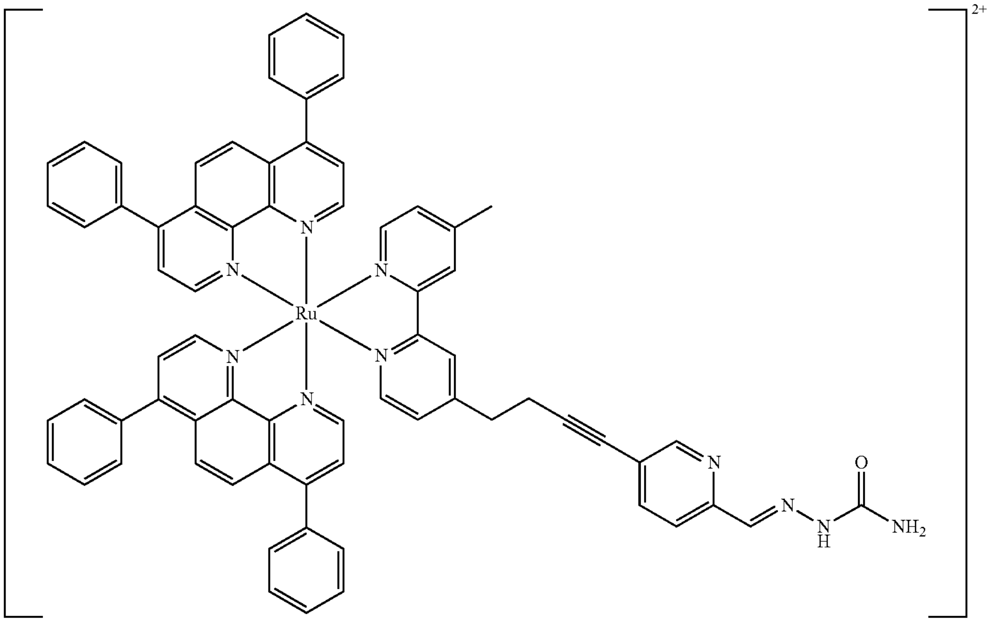
$(Cl^-)_2$,

-continued
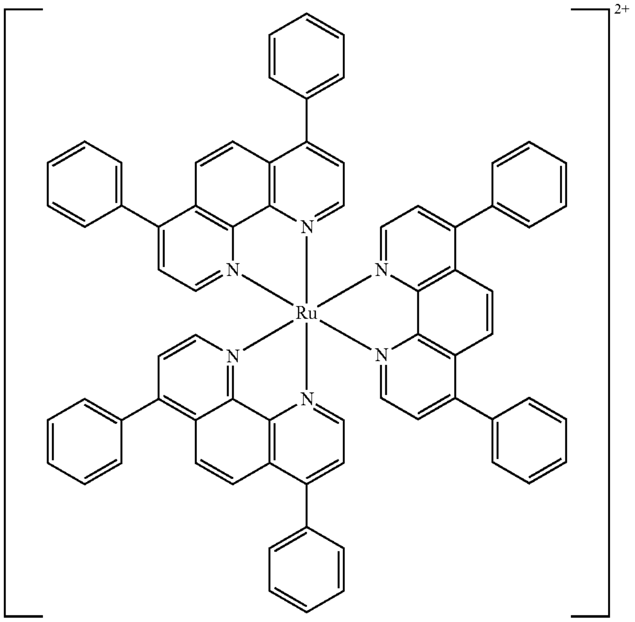
$(X^-)_2$
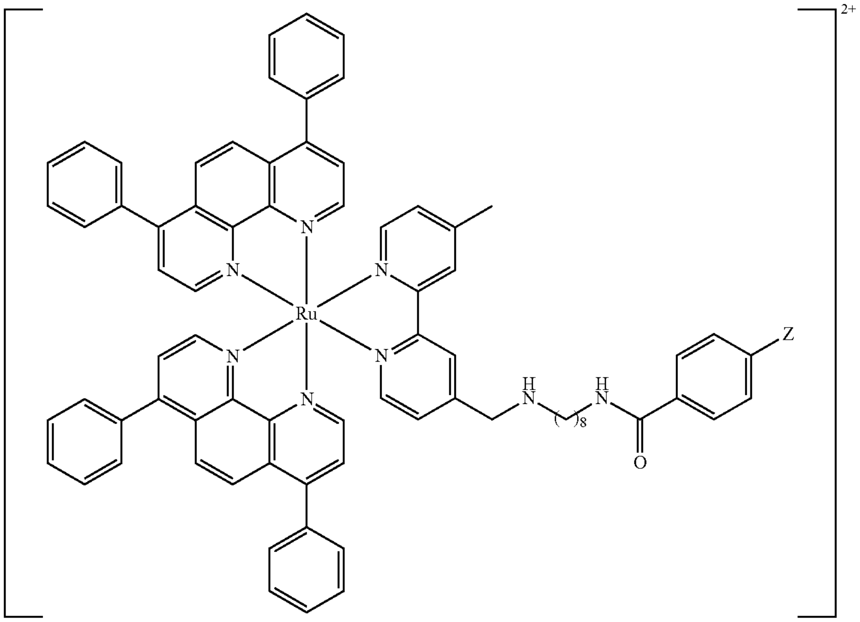
$(X^-)_2$ with
Z =
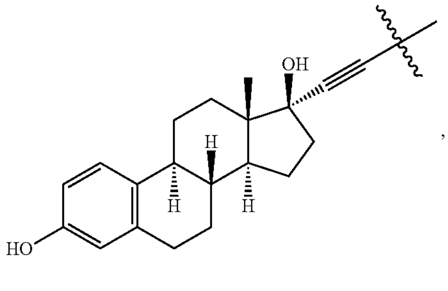
,

-continued
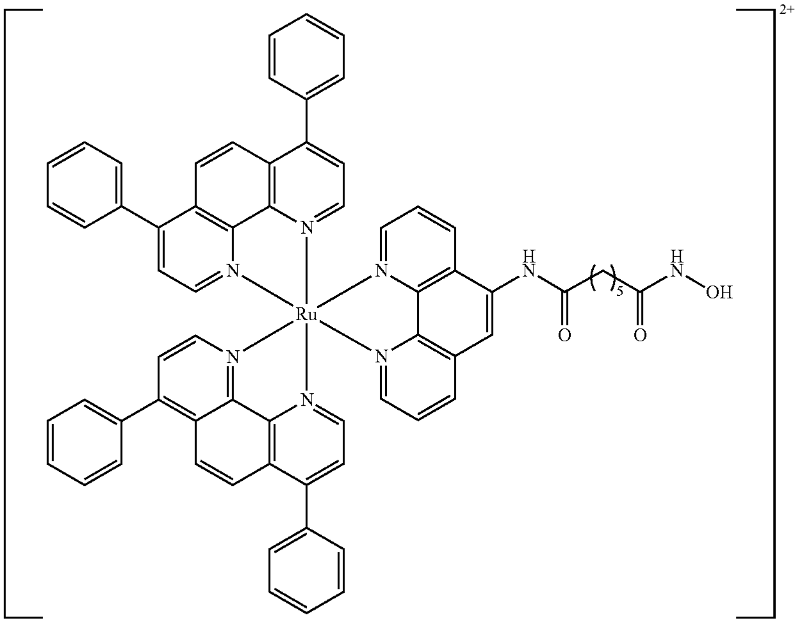
$(X^-)_2$,
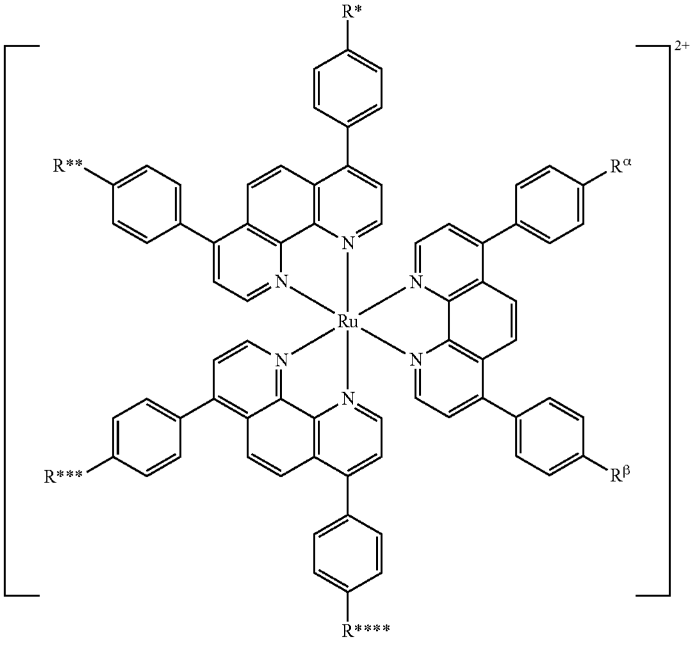
$(X^-)_2$,

-continued
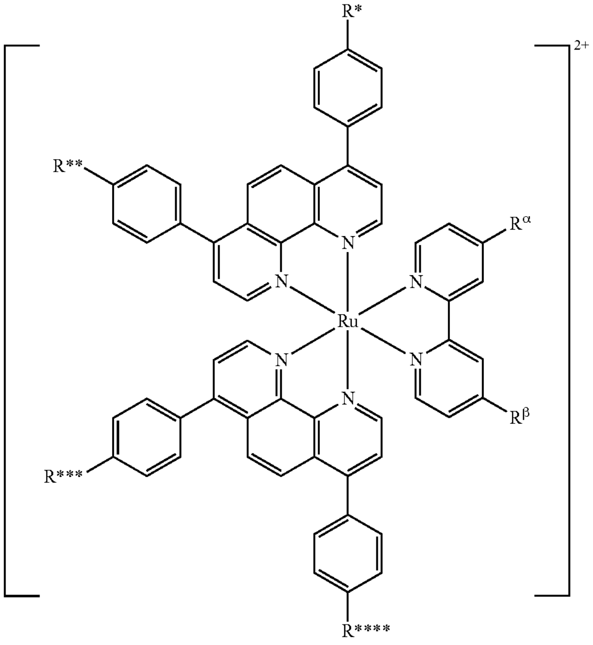
$(X^-)_2$
in which of $R^\alpha$, $R^\beta$, R*, R, R* and R**** are each independently H, $CH_3$, COOH or $NH_2$, provided that at least one or two of $R^\alpha$ and $R^\beta$ is COOH or $NH_2$,
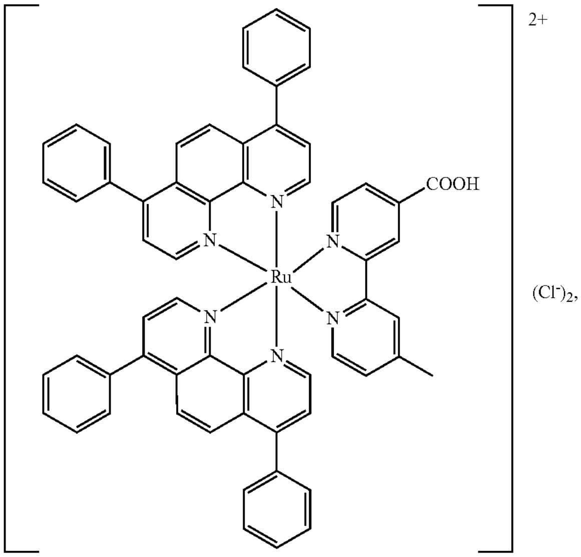
$(Cl^-)_2$,
-continued
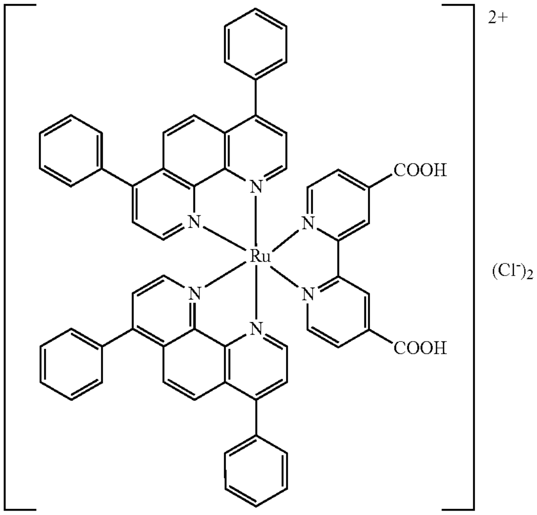
$(Cl^-)_2$ and -continued

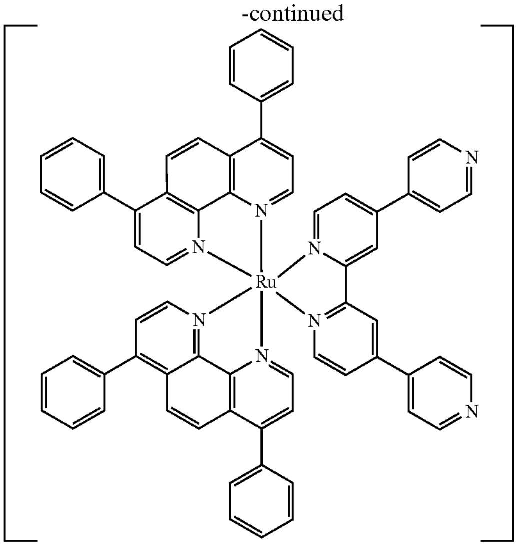

2+

$(Cl^-)_2$.

In a third aspect, the present invention concerns a method of preparation of compounds of formula (I) and pharmaceutically acceptable salts and/or solvates thereof as described above.

In a fourth aspect, the present invention relates to a conjugate comprising a compound of formula (I) linked to a biomolecule.

The present invention also relates to the conjugate as described above for use as a drug, notably as a photosensitizer agent in photodynamic therapy.

The present invention also relates to the use of the conjugate as described above for the manufacture of a drug, notably intended to be used as a photosensitizer agent in photodynamic therapy.

The present invention also relates to the use of the conjugate as described above as a drug, notably intended to be used as a photosensitizer agent in photodynamic therapy.

The present invention also relates to a method of treatment by photodynamic therapy comprising administering to an animal, in particular a mammal such as a human, in need thereof an effective amount of a conjugate as described above as a photosensitizer agent.

In a fifth aspect, the present invention relates to a pharmaceutical composition comprising at least one compound of formula (I) or a pharmaceutically acceptable salt and/or solvate thereof.

Preferably, said compound is not:

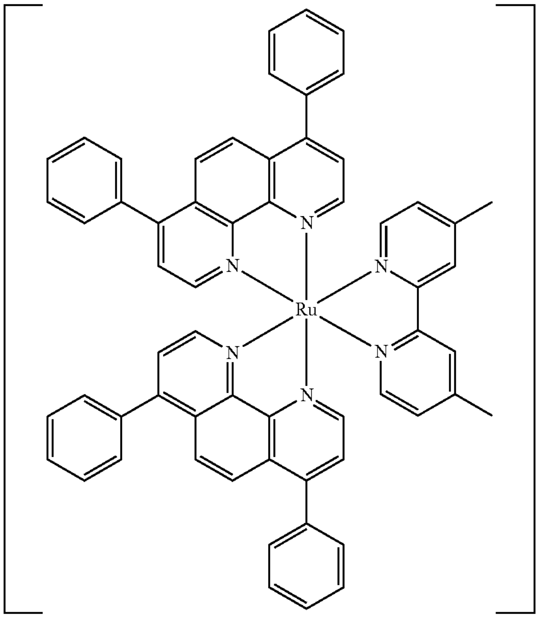

2+

$(PF_6^-)_2$,

-continued
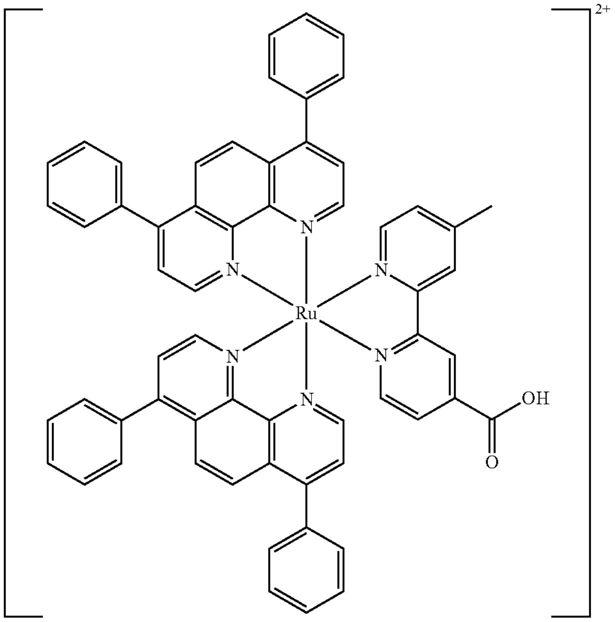
$(PF_6^-)_2$,
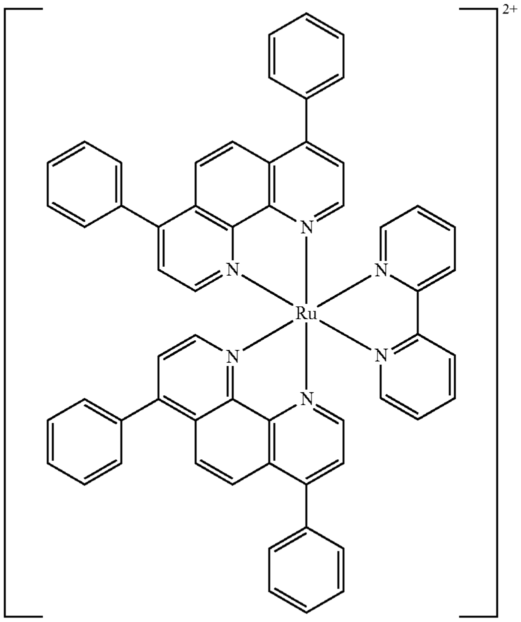
$(Cl^-)_2$,

-continued
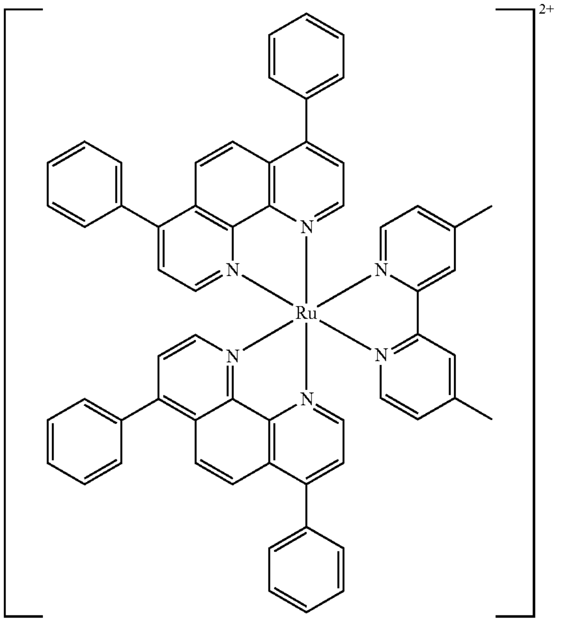
$(Cl^-)_2$,
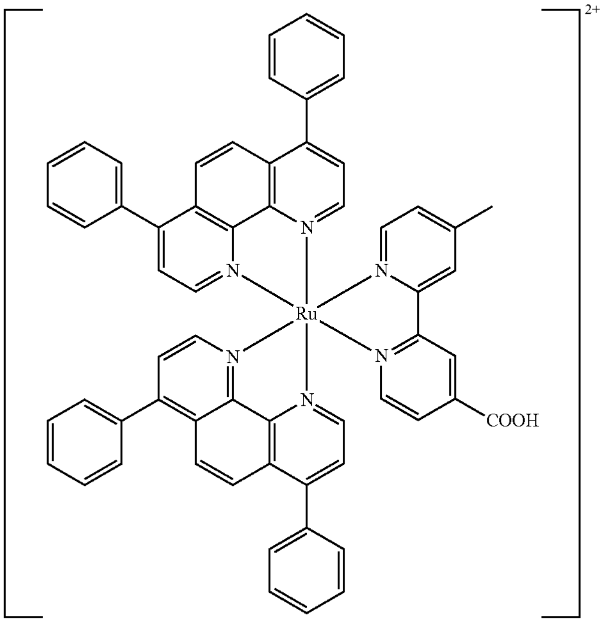
$(Cl^-)_2$,

-continued
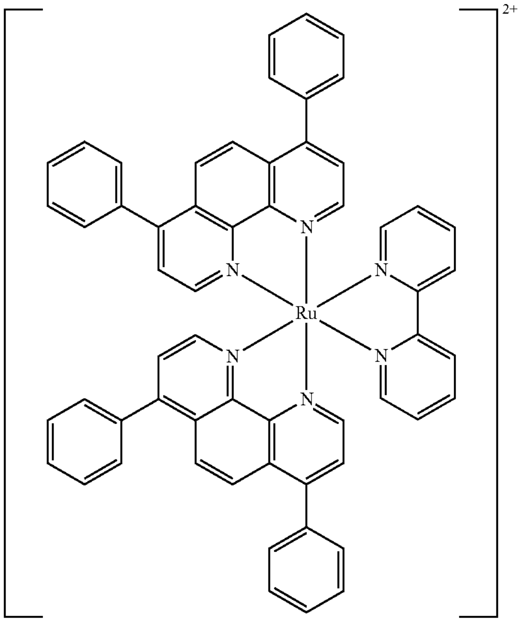
$(PF_6^-)_2$,
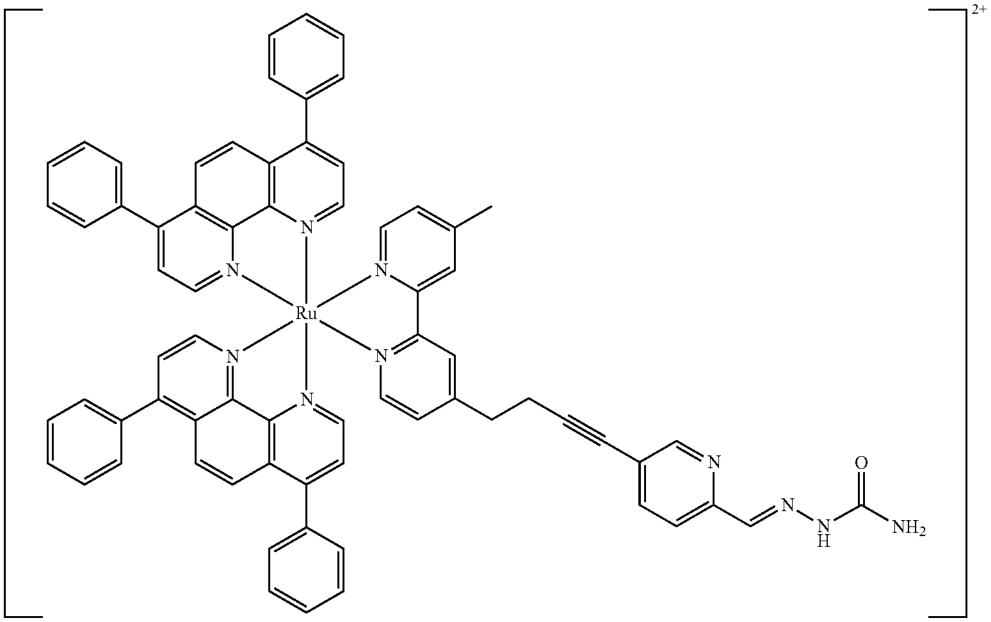
$(Cl^-)_2$,

-continued
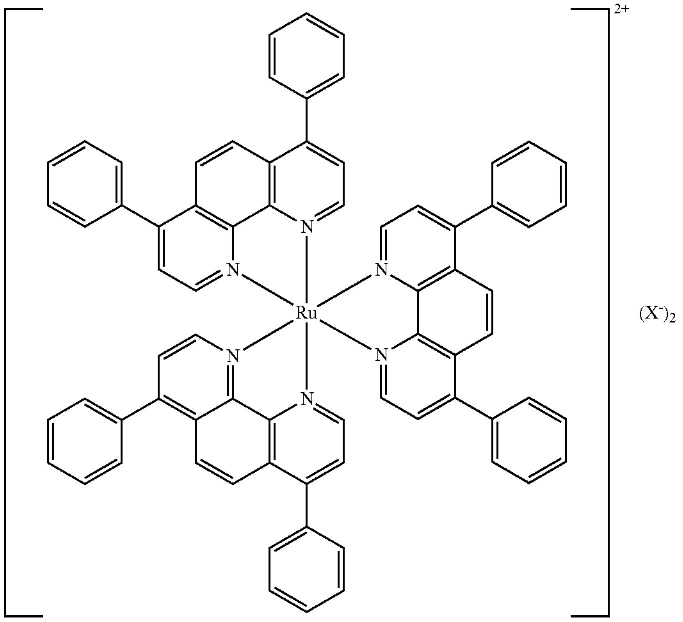
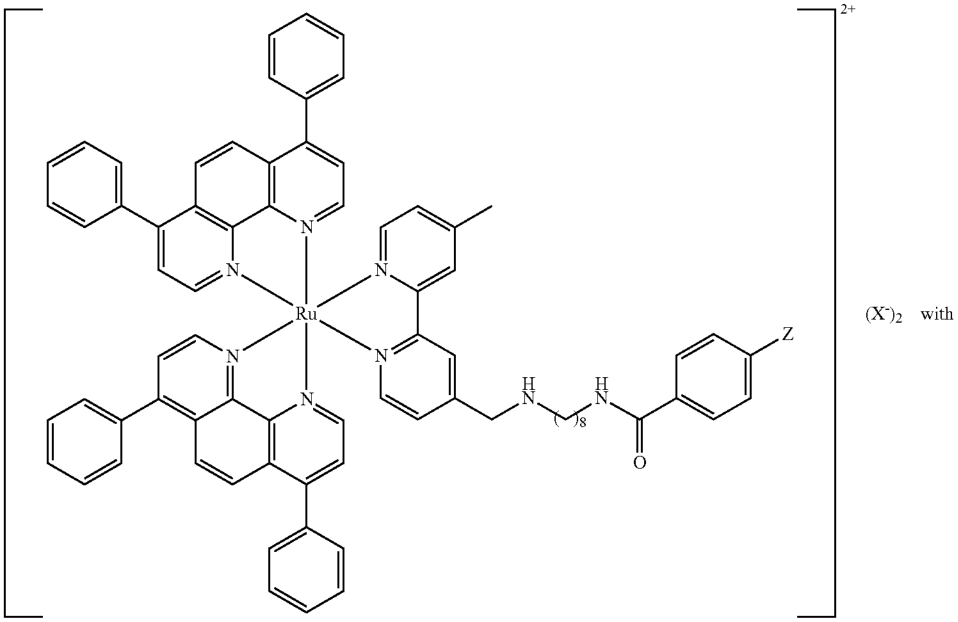
Z = 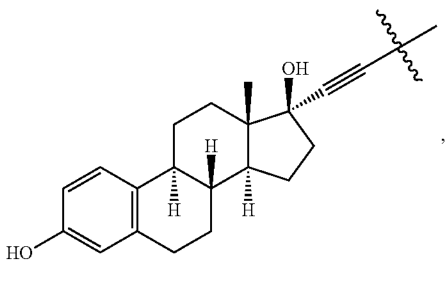,

-continued
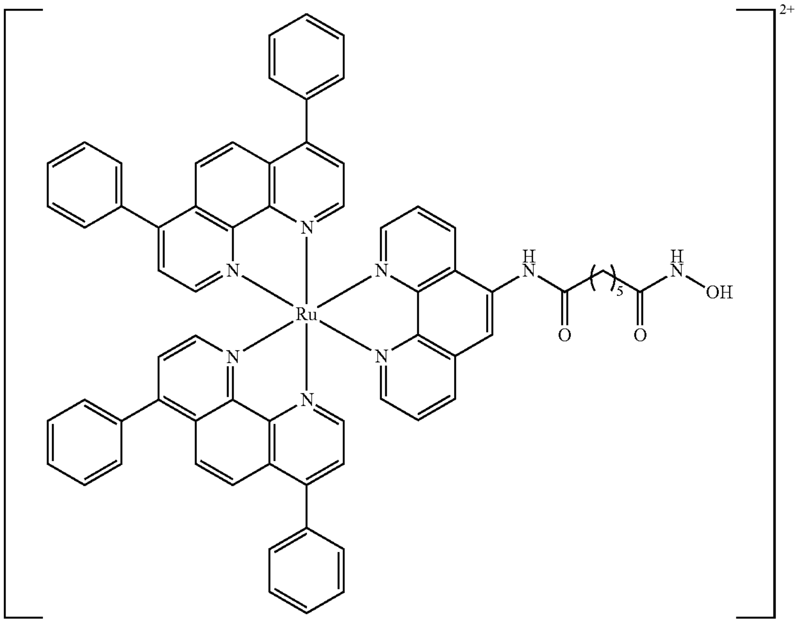
$(X^-)_2$,
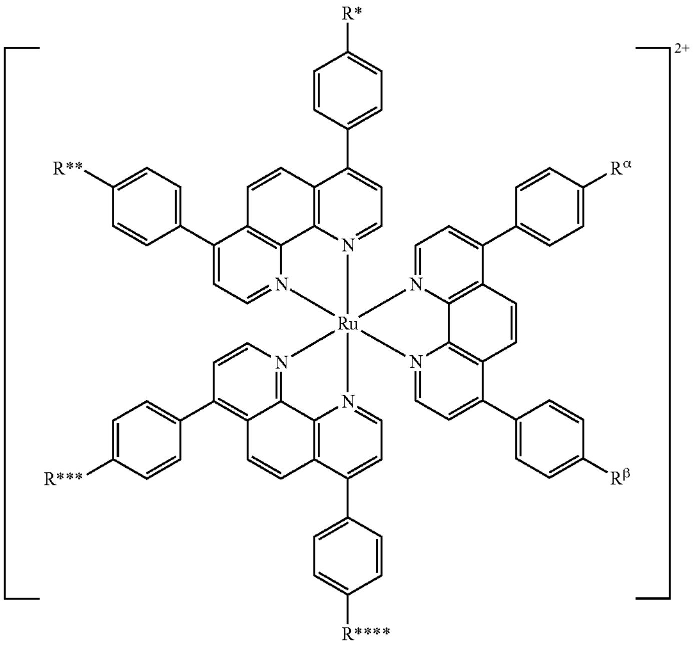
$(X^-)_2$,

-continued
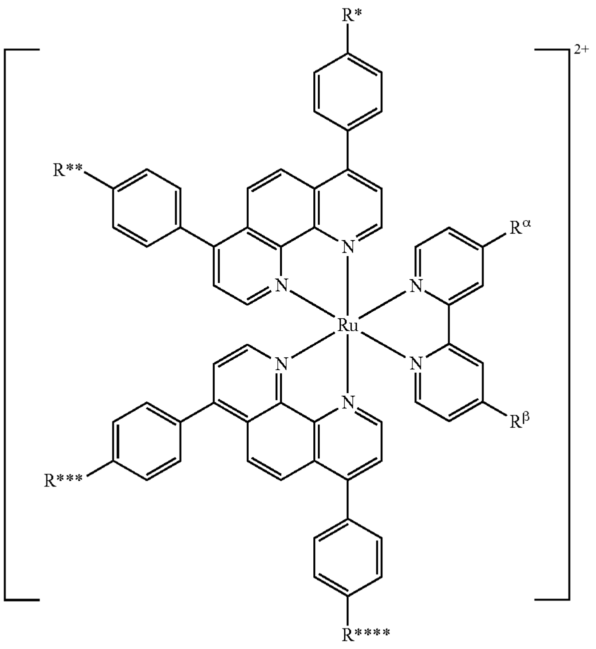
$(X^-)_2$
in which of $R^\alpha$, $R^\beta$, R*, R, R* and R**** are each independently H, $CH_3$, COOH or $NH_2$, provided that at least one or two of $R^\alpha$ and $R^\beta$ is COOH or $NH_2$,
-continued
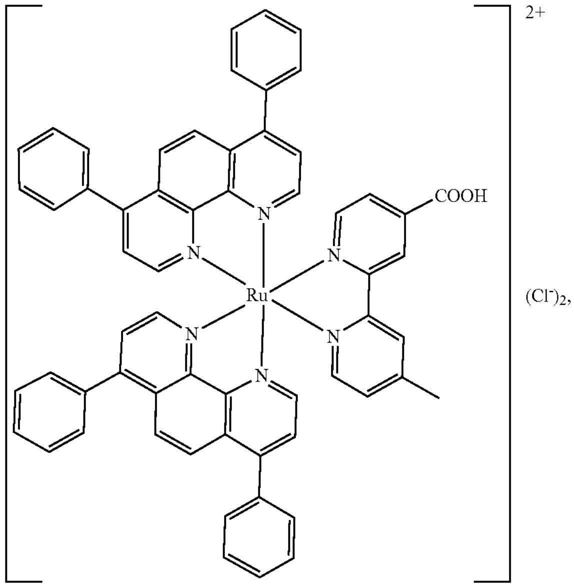
$(Cl^-)_2$,
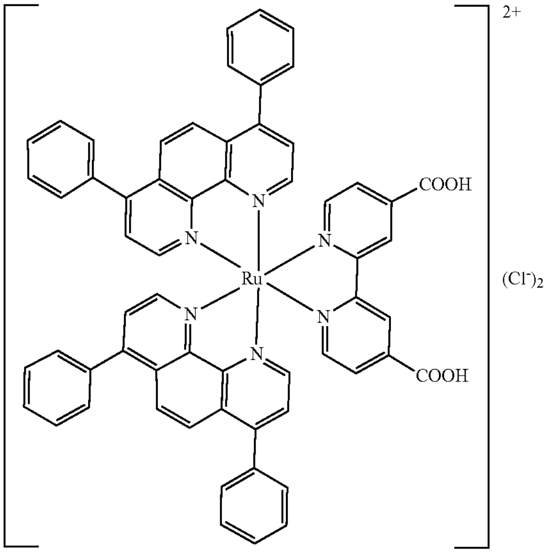
$(Cl^-)_2$ and -continued

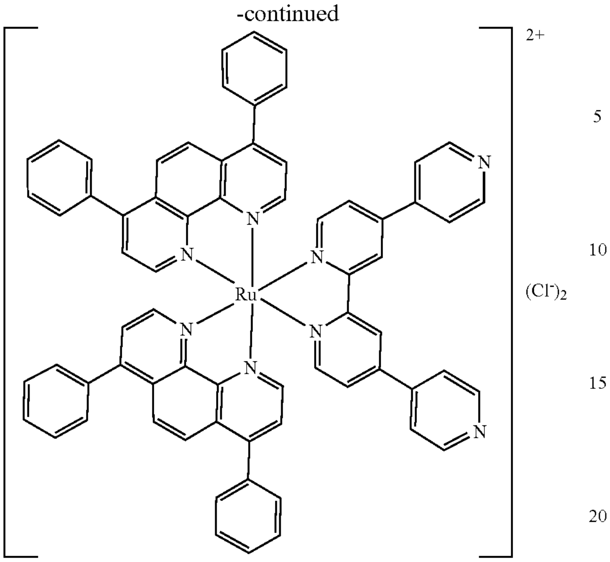

or a conjugate according to the invention and at least one pharmaceutically acceptable excipient.

The present invention also relates to the pharmaceutical composition as described above for use as a drug.

Definition

The term "stereoisomers" used in this invention refers to configurational stereoisomers and more particularly to optical isomers.

In the present invention, the optical isomers result in particular from the different position in space of the three bidentate ligands of the ruthenium. Ruthenium thus represents a chiral or asymmetric center. Optical isomers that are not mirror images of one another are thus designated as "diastereoisomers", and optical isomers, which are non-superimposable mirror images are designated as "enantiomers".

An equimolar mixture of two enantiomers of a chiral compound is designated as a racemic mixture or racemate.

For the purpose of the invention, the term "pharmaceutically acceptable" is intended to mean what is useful to the preparation of a pharmaceutical composition, and what is generally safe and non-toxic, for a pharmaceutical use.

The term "pharmaceutically acceptable salt and/or solvate" is intended to mean, in the framework of the present invention, a salt and/or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L25 tartaric, tartaric, p-toluenesulfonic, trimethylacetic, and trifluoroacetic acid and the like, and (2) base addition salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The term "halogen", as used in the present invention, refers to a fluorine, bromine, chlorine or iodine atom.

The term "$C_1$-$C_6$ alkyl", as used in the present invention, refers to a straight or branched monovalent saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "$C_2$-$C_6$ alkenyl", as used in the present invention, refers to a straight or branched monovalent unsaturated hydrocarbon chain containing from 2 to 6 carbon atoms and comprising at least one double bond including, but not limited to, ethenyl, propenyl, butenyl, pentenyl, hexenyl and the like.

The term "$C_2$-$C_6$ alkynyl", as used in the present invention, refers to a straight or branched monovalent unsaturated hydrocarbon chain containing from 2 to 6 carbon atoms and comprising at least one triple bond including, but not limited to, ethynyl, propynyl, propynyl, butynyl, pentynyl, hexynyl and the like.

The term "$C_1$-$C_6$ haloalkyl" refers to a $C_1$-$C_6$ alkyl chain as defined above wherein one or more hydrogen atoms are replaced by a halogen atom selected from fluorine, chlorine, bromine or iodine, preferably a fluorine atom. For example, it is a $CF_3$ group.

The term "carbocycle" refers to a non-aromatic hydrocarbon ring, saturated or unsaturated, typically comprising from 3 to 20 carbons and comprising one or more fused or bridged ring(s). For example, it is a saturated hydrocarbon cycle, especially a $C_3$-$C_2$ cycloalkyl. In particular, it is a unsaturated hydrocarbon cycle, especially a $C_3$-$C_8$ cycloalkene or cycloalkyne including, but not limited to, cyclopropene, cyclobutene, cyclopentene, cyclohexene, 1,4-cyclohexadiene, cycloheptene, cycloheptyne, cyclooctene, cyclooctyne and the like.

The term "$C_3$-$C_2$ cycloalkyl" refers to a saturated hydrocarbon ring comprising from 3 to 7 carbons, including cyclopropyl, cyclobutyl, cyclopentyl, cyclohexyl and cycloheptyl.

The term "heterocycle" as used in the present invention refers to a non-aromatic, saturated or unsaturated monocycle or polycycle (comprising fused, bridged or Spiro rings) comprising preferably 5 to 10, notably 5 or 6, atoms in the ring(s), in which the atoms of the ring(s) consist of carbon atoms and one or more, advantageously 1 to 4, and more advantageously 1 or 2, heteroatoms, such as a nitrogen, oxygen or sulphur atom, the remainder being carbon atoms. In particular, it can be an unsaturated ring, such as an unsaturated 5 or 6-membered monocycle. Preferably it comprises 1 or 2 nitrogen, in particular one. A heterocycle can be notably piperidinyl, piperizinyl, pyrrolidinyl, pyrazolidinyl, imidazolidinyl, azepanyl, thiazolidinyl, isothiazolidinyl, oxazocanyl, thiazepanyl, benzimidazolonyl.

When the heterocycle is substituted, it is advantageously substituted by a group selected in the group consisting of $C_1$-$C_6$ alkyl and oxo, in particular oxo. Preferably, a substituted heterocycle in the context of the present invention is a maleimidyl group of formula:

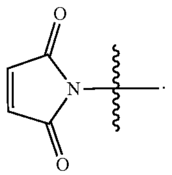 [SMILES: *N1C(=O)C=CC1=O]

The term "aryl" refers to an aromatic hydrocarbon group preferably comprising from 6 to 12 carbon atoms and comprising one or more fused rings, such as, for example, a phenyl or naphthyl group. Advantageously, it is a phenyl group.

The term "heteroaryl", as used in the present invention, refers to an aromatic group comprising one or several, notably one or two, fused hydrocarbon cycles in which one or several, notably one to four, advantageously one or two, carbon atoms each have been replaced with a heteroatom selected from a sulfur atom, an oxygen atom and a nitrogen atom, preferably selected from an oxygen atom and a nitrogen atom. It can be a furyl, thienyl, pyrrolyl, pyridyl, oxazolyl, isoxazolyl, thiazolyle, isothiazolyl, imidazolyl, pyrazolyl, oxadiazolyl, thiadiazolyl, triazolyl, tetrazolyl, pyridazinyl, pyrimidinyl, pyrazinyl, triazinyl, quinolyl, isoquinolyl, quinoxalyl or indyl.

In the context of the present invention, "unsaturated" means that the hydrocarbon chain may contain one or more unsaturation(s), i.e. a double bond C═C or a triple bond C≡C, advantageously one.

In the context of the present invention, "optionally substituted" means that the group in question is optionally substituted with one or more substituents which may be selected in particular from halogen, $C_1$-$C_6$ alkyl, $C_1$-$C_6$ haloalkyl, $C_2$-$C_6$ alkene, $C_2$-$C_6$ alkyne, aryl, $N_3$, oxo, $NR^aR^b$, $COR^c$, $CO_2R^d$, $CONR^eR^f$, $OR^g$, CN and $NO_2$ wherein $R^a$ to $R^g$ are, independently of one another, H, $C_1$-$C_6$ alkyl, $C_1$-$C_6$ haloalkyl or aryl, preferably H or $C_1$-$C_6$ alkyl. Advantageously, the one or more substituents are selected from halogen, $C_1$-$C_6$ haloalkyl, $C_2$-$C_6$ alkene, $C_2$-$C_6$ alkyne, aryl, $N_3$, oxo, $NR^aR^b$, $COR^c$, $CO_2R^d$, $CONR^eR^f$, $OR^g$, CN and $NO_2$ wherein $R^a$ to $R^g$ are as defined previously, in particular, when the "optionally substituted" group is an optionally substituted $C_1$-$C_6$ alkyl group.

The term "pharmaceutical composition" is meant in the framework of the present invention a composition having preventive and curative properties towards cancers.

The term "biomolecule" refers to molecule having biological properties. In the context of the present invention, it refers to a protein, a peptide, an aptamer, an antibody or an antigen binding fragment thereof, or an affibody.

The term "peptide" as used herein refers to a linear molecule of 50 amino acid residues or less which are combined with each other by a peptide bond (CO—NH). Peptide bonds are formed between the carboxyl group of one amino acid and the amino group of the next amino acid.

The terms "protein" and "polypeptide", as used herein, are synonyms and refer to polymers of more than 50 amino acids covalently linked through peptide bonds into a chain. Peptide bonds are formed between the carboxyl group of one amino acid and the amino group of the next amino acid.

The term "aptamer" refers to single stranded oligonucleotides that can naturally fold into different 3-dimensional structures, which have the capability of binding specifically to biosurfaces, a target compound or a moiety.

The term "antibody" is used herein in the broadest sense and specifically covers monoclonal antibodies (including full length monoclonal antibodies) of any isotype such as IgG, IgM, IgA, IgD, and IgE, polyclonal antibodies, multispecific antibodies, and chimeric antibodies. An antibody reactive with a specific antigen can be generated by recombinant methods such as selection of libraries of recombinant antibodies in phage or similar vectors, or by immunizing an animal with the antigen or an antigen-encoding nucleic acid. A typical antibody is comprised of two identical light chains and two identical heavy chains that are joined by disulfide bonds.

As used herein, the term "monoclonal antibody" refers to an antibody arising from a nearly homogeneous antibody population.

The term "antigen-binding fragments" of an antibody means a portion of an intact antibody which is capable of binding the antigen. Examples of antibody fragments include Fab, Fab', F(ab')2 and Fv fragments, CDR, antigen-binding site, heavy or light chain variable region, diabodies, triabodies single chain antibody molecules (scFv) and multispecific antibodies formed from at least two intact antibodies or fragments thereof or (poly) peptides that contain at least a fragment of an immunoglobin that is sufficient to confer antigen binding to the polypeptide.

Affibody® (hereinafter "affibody") molecules are small highly robust proteins with specific affinities to target proteins. They can be designed and used, for example, like aptamers.

The term "peptide coupling" refers to a chemical reaction between an amine function and a carboxylic acid function. The peptide coupling will be advantageously carried out in the presence of a coupling agent, such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), hexafluorophosphate 2-(1H-benzotriazole-1-yl)-1,1,3,3-tetramethyluronium (HBTU), tetrafluoroborate 2-(1H-benzotriazole-1-yl)-1,1,3,3-tetramethyluronium (TBTU), hexafluorophosphate O-(7-azobenzotriazol-1-yl)-1,1,3,3-tetramethyluronium (HATU), (benzotriazol-1-yloxy)tripyrrolodinophosphonium hexafluorophosphate (PyBOP) or propylphosphonic anhydride; optionally associated with an additive or a base, such as N-hydroxy-succinimide (NHS), N-hydroxy-benzotriazole (HOBt), 3,4-dihydro-3-hydroxy-4-oxo-1,2,3-benzotriazole (HOOBt), I-hydroxy-7-azabenzotriazole (HAt), N-hydroxysylfosuccinimide (sulfo NHS), dimethylaminopyridine (DMAP), diisopropylethylamine (DIEA) or N-methylmorpholine (NMM).

The term "click chemistry" refers to a chemical reaction between an azide function ($-N_3$) and an alkyne function (preferably a terminal alkyne function —C≡CH). Said reaction is also called azide-alkyne Huisgen cycloaddition. In the context of the present invention, the "click chemistry" typically enables to graft one or more compound of formula (I) to a biomolecule. For that, the compound of formula (I) is functionalized with an azide or alkyne function, whereas the biomolecule to be grafted is functionalized with the other function, i.e. respectively an alkyne or azide function. The azide and alkyne functions react together to form a 1,2,3-triazole by a 1,3-dipolar cycloaddition. Such a reaction is illustrated on the scheme below in the case where the azide function is carried by a compound of formula (I) whereas the biomolecule is functionalised with an alkyne function.

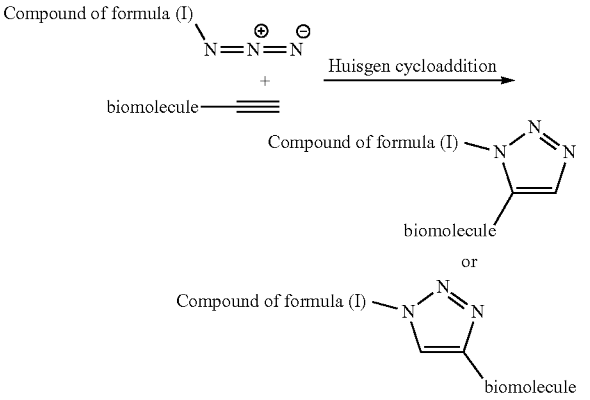

Such a cycloaddition reaction between an azide and an alkyne can be catalyzed by a copper (I) catalyst such as CuBr or CuI. However, the copper (I) catalyst can be formed in situ by reduction of a copper (II) species, in particular by reduction of a copper (II) salt such as $CuSO_4$ in the presence of a reducing agent such as ascorbic acid or a salt thereof. The cycloaddition can be performed in various solvents, such as alcohols (such as tert-butanol), dimethylsulfoxyde (DMSO), N,N-dimethylformamide (DMF), acetone, water or mixtures thereof.

The term "reductive amination" refers to a chemical reaction between a carbonyl group, such as an aldehyde or a ketone, preferably an aldehyde, and an amine to form substituted amines. A primary amine will thus form a secondary amine and a secondary amine will form a tertiary amine. A tertiary amine cannot be used as starting reagent. The amine to be substituted in the reductive amination has to comprise a N—H bond and preferably it is a primary amine $NH_2$.

In a first step the carbonyl group reacts with the amine to form an imine intermediate. Said imine is then reduced with a reducing agent to lead to the substituted amine. The reduction is advantageously achieved in situ. Reducing agent typically used in reductive amination are boranes or borohydride reagents like $NaBH_4$, $NaHB(OAc)_3$ or $NaH_3BCN$. The imine intermediate is advantageously protonated under acidic conditions to give iminium ion (its conjugate acid) before being reduced. Such acidic conditions allow increasing the rate of the reduction. Such a reaction is illustrated on the scheme below.

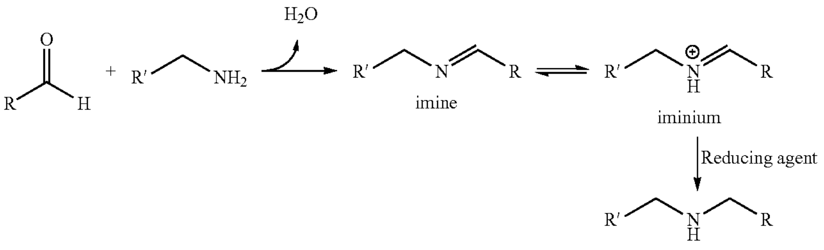

The term "photodynamic therapy" (PDT) refers to a non-invasive medical therapy which involves light and a photosensitizing chemical substance, called a photosensitizer (PS) used in conjunction with molecular oxygen to elicit cell death. The PDT is notably intended to treat a disease selected from cancer, bacterial infection, fungal infection, viral infection and skin disorders. A photosensitizer becomes highly toxic upon light irradiation, notably at wavelengths comprised between 450 nm and 595 nm.

During photodynamic therapy, the PS is administered either systemically or locally. The diseased area is then exposed to light. Upon light irradiation, the PS is able to create reactive oxygen species (ROS), such as singlet oxygen ($^1O_2$) or other radicals. Due to their high reactivity, these species can cause oxidative stress and damage in different surrounding cellular compartments (i.e. membrane, nucleus, endoplasmic reticulum, lysosome, mitochondria) leading to cell death.

DETAILED DESCRIPTION

Compound of Formula (I)

The compounds according to the present invention can be in the form of a stereoisomer or a mixture of stereoisomers, such as a mixture of enantiomers, notably a racemic mixture.

Preferably, the compound of formula (I) is a compound of following formula (I-A):

(I-A)

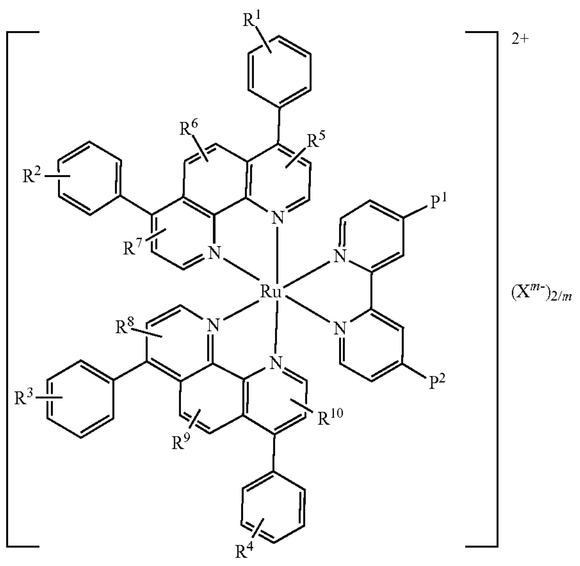

According to a preferred embodiment, $R^1$ to $R^{10}$ each independently represent one or several substituents selected in the group consisting of H, halogen, optionally substituted $C_1$-$C_6$ alkyl, optionally substituted $C_2$-$C_6$ alkenyl, optionally substituted $C_2$-$C_6$ alkynyl, optionally substituted aryl, $COR^{11}$, $OR^{12}$ and $NR^{13}R^{14}$. Preferably, $R^1$ to $R^{10}$ each independently represent one or several substituents selected in the group consisting of H, halogen, optionally substituted $C_1$-$C_6$ alkyl, optionally substituted aryl, $OR^{12}$ and $NR^{13}R^{14}$.

According to this embodiment, $R^{11}$ is preferably H, $C_1$-$C_6$ alkyl or $OR^{15}$ and $R^{12}$ to $R^{15}$ are preferably H or $C_1$-$C_6$ alkyl.

In particular $R^1$ to $R^{10}$ each independently represent one or several substituents selected in the group consisting of H, halogen and optionally substituted $C_1$-$C_6$ alkyl. More preferably, $R^1$ to $R^{10}$ represent H.

Advantageously, $P^1$ and $P^2$ each independently represent one or several substituents selected in the group consisting of H, halogen, optionally substituted $C_1$-$C_6$ alkyl, optionally substituted $C_2$-$C_6$ alkenyl, optionally substituted $C_2$-$C_6$ alkynyl, optionally substituted carbocycle, optionally substituted aryl, optionally substituted heteroaryl, optionally substituted heterocycle, CN, $NO_2$, $N_3$, $COR^{18}$, $OR^{19}$ and $NR^{20}R^{21}$, or $P^1$ and $P^2$ together with the pyridyl groups to which they are bonded represent

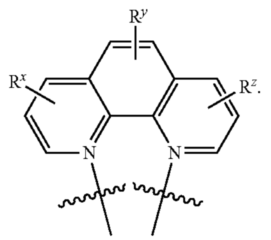

$R^x$, $R^y$ and $R^z$ are preferably selected in the group consisting of H, halogen, optionally substituted $C_1$-$C_6$ alkyl, optionally substituted $C_2$-$C_6$ alkenyl, optionally substituted $C_2$-$C_6$ alkynyl, optionally substituted aryl, optionally substituted heterocycle, $N_3$, $COR^{18}$, $OR^{19}$ and $NR^{20}R^{21}$. More preferably, $R^x$, $R^y$ and $R^z$ are selected in the group consisting of H, halogen, $C_1$-$C_6$ alkyl, $C_2$-$C_6$ alkenyl, $C_2$-$C_6$ alkynyl, aryl, heterocycle, $COR^{18}$, $OR^{19}$ and $NR^{20}R^{21}$.

In particular, $P^1$ and $P^2$ each independently represent one or several substituents selected in the group consisting of H, halogen, optionally substituted $C_1$-$C_6$ alkyl, optionally substituted $C_2$-$C_6$ alkenyl, optionally substituted $C_2$-$C_6$ alkynyl, optionally substituted carbocycle, optionally substituted aryl, optionally substituted heteroaryl, optionally substituted heterocycle, CN, $NO_2$, $N_3$, $COR^{18}$, $OR^{19}$ and $NR^{20}R^{21}$. Preferably, $P^1$ and $P^2$ each independently represent one or several substituents selected in the group consisting of H, halogen, optionally substituted $C_1$-$C_6$ alkyl, optionally substituted $C_2$-$C_6$ alkenyl, optionally substituted $C_2$-$C_6$ alkynyl, optionally substituted aryl, CN, $NO_2$, $N_3$ $COR^{18}$, $OR^{19}$ and $NR^{20}R^{21}$. According to this previous embodiment, $R^{18}$ is preferably H, optionally substituted $C_1$-$C_6$ alkyl or $OR^{22}$ and $R^{19}$ to $R^{22}$ are preferably H or $C_1$-$C_6$ alkyl.

Typically, $P^1$ and $P^2$ each independently represent one or several substituents selected in the group consisting of H, halogen, optionally substituted $C_1$-$C_6$ alkyl, optionally substituted $C_2$-$C_6$ alkenyl, $N_3$ and $COR^{18}$, $R^{18}$ being as defined above, in particular $R^{18}$ is selected among H, $C_1$-$C_6$ alkyl and $OR^{22}$, preferably H and $OR^{22}$, $R^{22}$ being preferably H or $C_1$-$C_6$ alkyl.

Preferably, $P^1$ and $P^2$ do not both represent H. In particular, $P^1$ and $P^2$ may each independently represent one or several substituents selected in the group consisting of halogen, optionally substituted $C_1$-$C_6$ alkyl, optionally substituted $C_2$-$C_6$ alkenyl, $N_3$ and $COR^{18}$, $R^{18}$ being as defined above, in particular $R^{18}$ is selected among H, $C_1$-$C_6$ alkyl and $OR^{22}$, preferably H and $OR^{22}$, $R^{22}$ being preferably H or $C_1$-$C_6$ alkyl.

According to a preferred embodiment, $P^1$ and $P^2$ each independently represent one or several substituents selected in the group consisting of:

- $C_1$-$C_6$ alkyl, preferably a methyl, optionally substituted with one or more substituents selected among halogen, $N_3$, COR', COOR', CONR'R", OR', NR'R" and heterocycle, wherein R' and R" are independently of each other H or $C_1$-$C_6$ alkyl, the heterocycle being optionally substituted by one or more substituents selected among halogen, $C_1$-$C_6$ alkyl and oxo group,
- $C_2$-$C_6$ alkenyl, in particular an ethenyl, optionally substituted with one or several, preferably one, substituents selected among halogen, $N_3$, COR', COOR', CONR'R", OR', NR'R" and heterocycle, wherein R' and R" are independently of each other H or $C_1$-$C_6$ alkyl, the heterocycle being optionally substituted by one or more substituents selected among halogen, $C_1$-$C_6$ alkyl and oxo group,
- $C_2$-$C_6$ alkynyl, optionally substituted with at least one substituent selected among halogen, COR', COOR', CONR'R", OR', NR'R" and heterocycle, wherein R' and R" are independently of each other H or $C_1$-$C_6$ alkyl, the heterocycle being optionally substituted by one or more substituents selected among halogen, $C_1$-$C_6$ alkyl and oxo group, the triple bond being preferably in terminal position,
- $N_3$, and
- $COR^{18}$, $R^{18}$ being preferably H or OH.

According to a more preferred embodiment, N and $P^2$ each independently represent one or several substituents selected in the group consisting of:

- $C_1$-$C_6$ alkyl, preferably a methyl, optionally substituted with one or more substituents selected among halogen, COR', COOR', CONR'R", OR', NR'R" and heterocycle, wherein R' and R" are independently of each other H or $C_1$-$C_6$ alkyl, the heterocycle being optionally substituted by one or more substituents selected among halogen, $C_1$-$C_6$ alkyl and oxo group,
- $C_2$-$C_6$ alkenyl, in particular an ethenyl, optionally substituted with one or several, preferably one, substituents selected among halogen, COR', COOR', CONR'R", OR', NR'R" and heterocycle, wherein R' and R" are independently of each other H or $C_1$-$C_6$ alkyl, the heterocycle being optionally substituted by one or more substituents selected among halogen, $C_1$-$C_6$ alkyl and oxo group, and
- $COR^{18}$, $R^{18}$ being preferably H or OH.

In the above-mentioned embodiments of $P^1$ and $P^2$, the heterocycle is preferably a 5 or 6-membered monocycle, notably unsaturated. Preferably it comprises 1 or 2 nitrogen, in particular one. Advantageously, the heterocycle is substituted by one or more substituents selected among halogen, $C_1$-$C_6$ alkyl and oxo group, in particular oxo group. More preferably, the heterocycle is a maleimidyl group.

Advantageously, one of $P^1$ and $P^2$ is selected so as to comprise a functional group which allows the coupling of the compound of formula (I) with a biomolecule. Thus, one of $P^1$ and $P^2$ advantageously comprises $N_3$, $C_2$-$C_6$ alkyne, COR', COOR', CONR'R", OR', NR'R" or unsaturated heterocycle, wherein R' and R" are independently of each other as defined above, preferably H or $C_1$-$C_6$ alkyl, the heterocycle being optionally substituted by one or more substituents selected among halogen, $C_1$-$C_6$ alkyl and oxo group.

Preferably, one of $P^1$ and $P^2$ comprises a functional group selected among CHO, COOH, $NH_2$ and a maleimidyl group. According to a particular embodiment, one of $P^1$ and $P^2$ represents CHO or COOH. According to another particular embodiment, one of $P^1$ and $P^2$ represents a maleimidyl group.

In a preferred embodiment, the compound of formula (I) is a compound of formula (I-A) wherein $R^1$ to $R^{10}$ are H and $P^1$ and $P^2$ are selected in the group consisting of:

$C_1$-$C_6$ alkyl, preferably a methyl, optionally substituted with one or more substituents selected among halogen, COR', COOR', CONR'R", OR', NR'R" and heterocycle, wherein R' and R" are independently of each other H or $C_1$-$C_6$ alkyl, the heterocycle being optionally substituted by one or more substituents selected among halogen, $C_1$-$C_6$ alkyl and oxo group, $C_2$-$C_6$ alkenyl, in particular an ethenyl, optionally substituted with one or several, preferably one, substituents selected among halogen, COR', COOR', CONR'R", OR', NR'R" and heterocycle, wherein R' and R" are independently of each other H or $C_1$-$C_6$ alkyl, the heterocycle being optionally substituted by one or more substituents selected among halogen, $C_1$-$C_6$ alkyl and oxo group, and $COR^{18}$, $R^{18}$ being preferably H or OH.

In this embodiment, the heterocycle is preferably a 5 or 6-membered monocycle, notably unsaturated. Preferably it comprises 1 or 2 nitrogen, in particular one. Advantageously, the heterocycle is substituted by one or more substituents selected among halogen, $C_1$-$C_6$ alkyl and oxo group, in particular oxo group. More preferably, the heterocycle is a maleimidyl group.

According to a preferred embodiment, the compound of formula (I) is selected among:

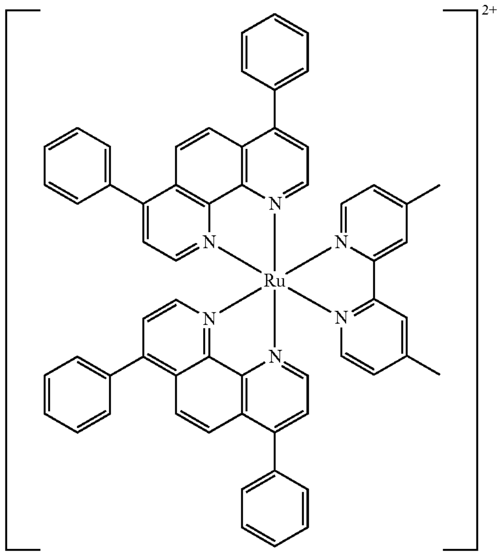

$(PF_6^-)_2$,

-continued

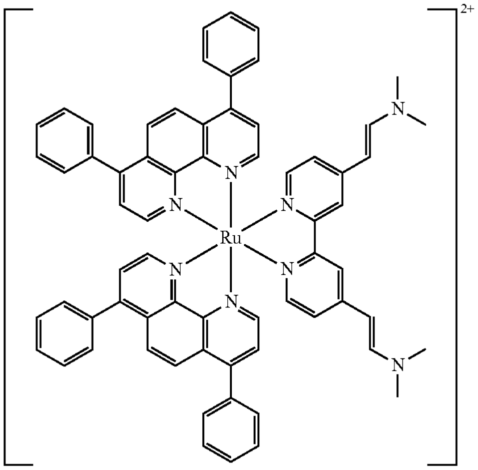

$(PF_6^-)_2$,

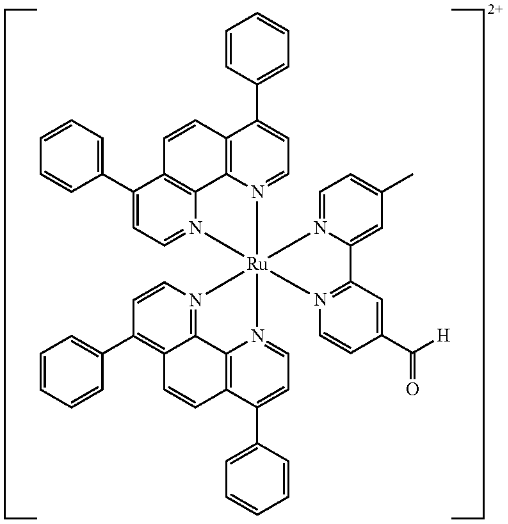

$(PF_6^-)_2$,

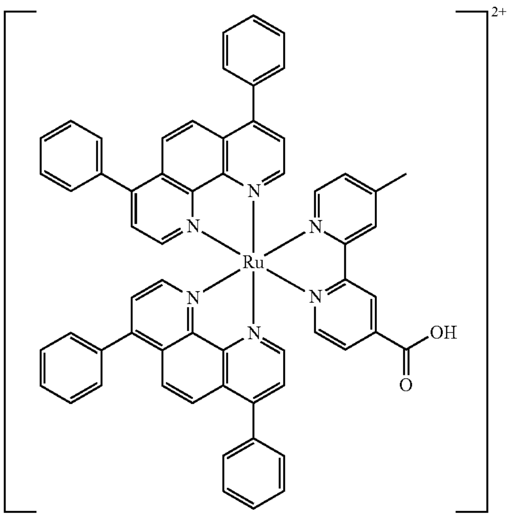

$(PF_6^-)_2$,

-continued
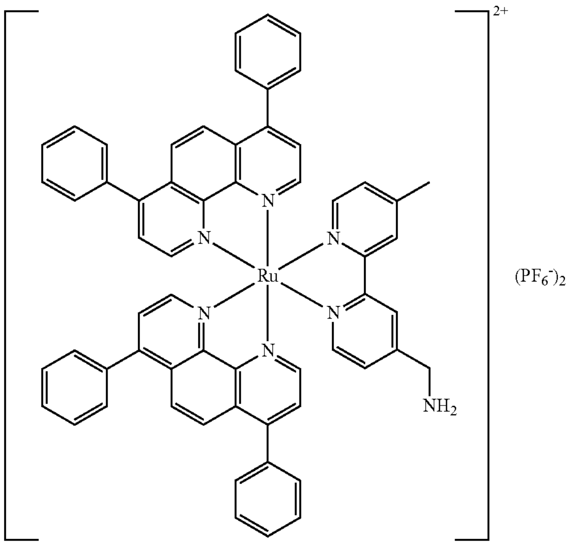
and
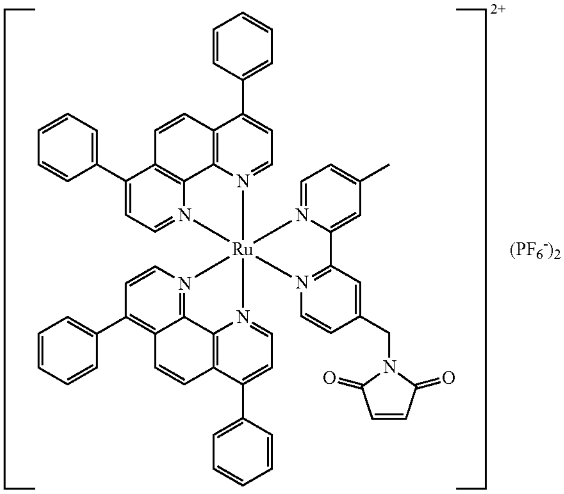
and the pharmaceutically acceptable salts and/or solvates thereof.
According to a particular embodiment, the compound of formula (I) is selected among:
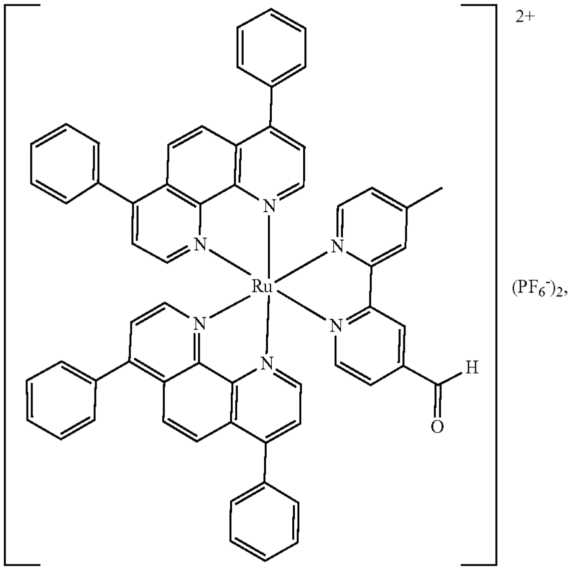
,
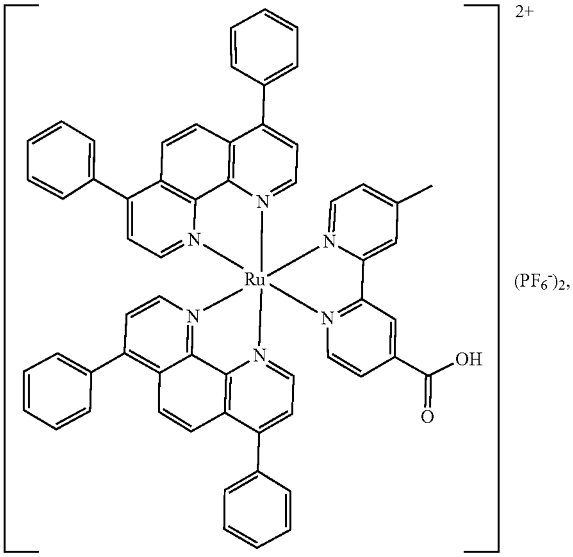
,
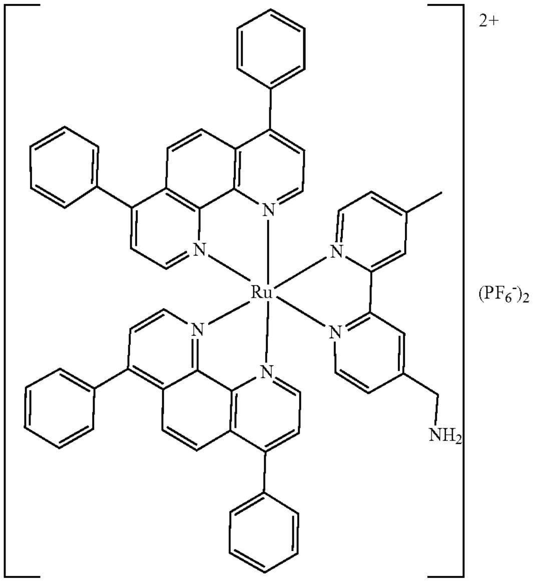
and -continued

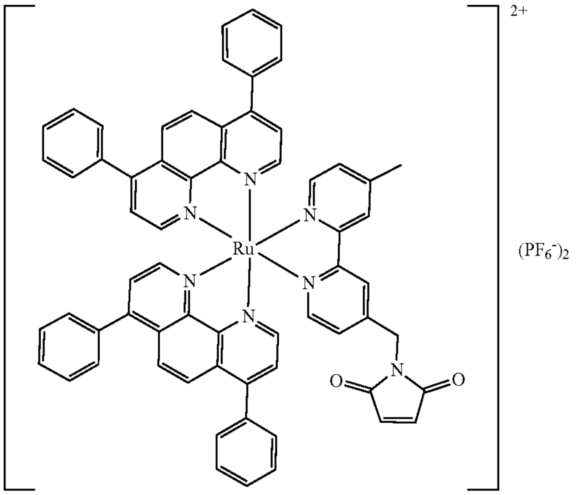

and the pharmaceutically acceptable salts and/or solvates thereof, said compounds carrying a functional group which enables the coupling with a biomolecule.

Method of Preparation of a Compound of Formula (I)

The present invention relates to a method of preparation of a compound of formula (I) as described above, or a pharmaceutically acceptable salt and/or solvate thereof, said method comprising the following steps:

(i) reacting a compound of the following formula (II)

(II)

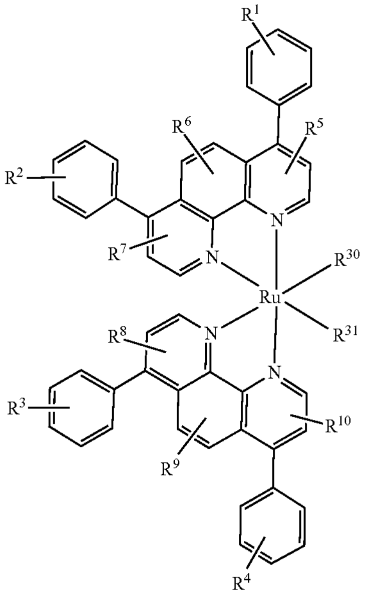

in which $R^1$ to $R^{10}$ are as defined above, $R^{30}$ and $R^{31}$ each independently represent halogen, $OR^{32}$ or $S(O)(C_1\text{-}C_6\ alkyl)_2$, such as $S(O)(CH_3)_2$, $R^{32}$ is H or $C_1$-$C_6$ alkyl, with a compound of formula (III)

(III)

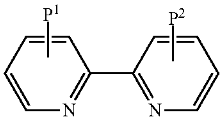

in which $P^1$ and $P^2$ are as defined above, (ii) reacting the product resulting from step (i) with a salt $A^{m+}X^{m-}$, wherein $X^{m-}$ is as defined above and $A^{m+}$ is a counter cation.

Step (i)

In the compound of formula (II), $R^{30}$ and $R^{31}$ are preferably identical and/or both represent a halogen, such as Cl. Compound of formula (II) advantageously corresponds to the following compound (II-A):

(II-A)

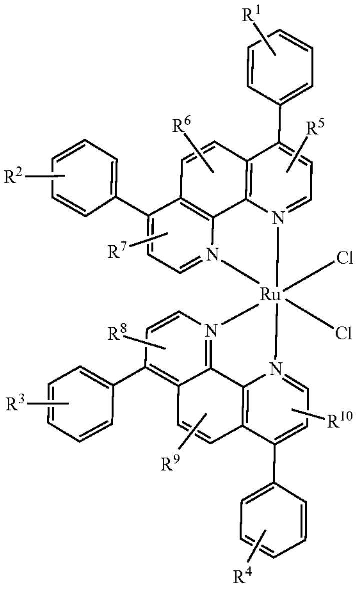

Compound of formula (II) can be obtained using suitable ligands according to methods described in the literature. For example, compound of formula (II-A) can be obtained according to methods described in Sullivan, B. et al., 1978.

Compound of formula (III) is commercially available or it can be obtained by functionalization reactions well-known from the skilled person in the art.

Step (i) corresponds to a ligand exchange wherein substituents $R^{30}$ and $R^{31}$ are replaced by the ligand

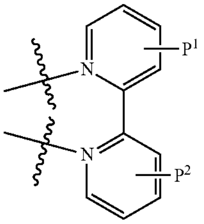

as described in compound of formula (I).

Optionally, additional steps of protection/deprotection and/or of functionalization well-known from the skilled person in the art may occur between steps (i) and (ii) to afford compound of formula (I) with substituents $P^1$ and $P^2$ as described above.

The reaction is preferably carried out in a polar solvent, preferably selected among water, alcohols, such as methanol, ethanol, propanol, butanol, and mixtures thereof. Preferably, the solvent is a mixture of water/alcohol, in particular water/ethanol.

The reaction is preferably carried out under inert atmosphere such as nitrogen ($N_2$) or argon (Ar) atmosphere.

The reaction is preferably carried out at a temperature corresponding to the boiling temperature of the solvent.

Step (ii)

$X^{m-}$ is a pharmaceutically acceptable anion, preferably selected in the group consisting of $PF_6^-$, $Cl^-$, $Br^-$, $I^-$, $BF_4^-$, ($C_1$-$C_6$ alkyl)-C(O)$O^-$, ($C_1$-$C_6$ haloalkyl)-C(O)$O^-$, ($C_1$-$C_6$-haloalkyl)-$SO_3^-$, $SO_4^{2-}$ and $PO_4^{3-}$. As described above, $X^{m-}$ is preferably selected among of $PF_6^-$, $Cl^-$, $Br^-$, $BF_4^-$, ($C_1$-$C_6$ alkyl)-C(O)$O^-$, ($C_1$-$C_6$ haloalkyl)-C(O)$O^-$, ($C_1$-$C_6$ alkyl)-$SO_3^-$ and ($C_1$-$C_6$ haloalkyl)-$SO_3^-$, $SO_4^{2-}$ and $PO_4^{3-}$, in particular $PF_6^-$, $Cl^-$, $Br^-$, $BF_4^-$, $CH_3C(O)O^-$, $CF_3C(O)O^-$ and $CF_3SO_3^-$, more preferably $X^{m-}$ is $PF_6^-$.

$A^{m+}$ is a counter cation preferably selected among $(N^+R^aR^bR^cR^d)_m$ (e.g. $(NH_4^+)_m$, $(NBu_4^+)_m$), $(H^+)_m$, $(Na^+)_m$, $(K^+)_m$ and $(Li^+)_m$, wherein $R^a$, $R^b$, $R^c$ and $R^d$ are each independently H or $C_1$-$C_6$ alkyl and m is 1, 2 or 3.

The salt $A^{m+}X^{m-}$ is thus preferably selected among the salts, but not limited to, $NH_4PF_6$, $NBu_4PF_6$, KCl, KBr, LiCl, LiBr, $HBF_4$, $NaOC(O)CH_3$, $KOC(O)CH_3$, $NH_4OCOCH_3$, $Na_2SO_4$, $H_3PO_4$. Preferably, the salt used in step (iii) is $NH_4PF_6$.

The compound obtained can be separated from the reaction medium by methods well known to the person skilled in the art, such as by extraction, evaporation of the solvent or by precipitation or crystallization (followed by filtration).

The compound can be also purified if necessary by methods well known to the person skilled in the art, such as by recrystallisation, by distillation, by chromatography on a column of silica gel or by high performance liquid chromatography (HPLC).

Conjugate Comprising a Compound of Formula (I) Linked to a Biomolecule

The present invention also relates to a conjugate comprising a compound of formula (I) as described above linked to a biomolecule such as a peptide, a protein, an aptamer, an antibody or antigen binding fragment thereof.

According to a particular embodiment, the conjugate according to the present invention has the following formula (IV):

$$\text{Ab-(L-D)}_n \quad \text{(IV)}$$

or a pharmaceutically acceptable salt and/or solvate thereof, wherein

Ab is a biomolecule such as a peptide, a protein, an aptamer, an antibody such as a monoclonal antibody, an antigen binding fragment thereof such as a nanobody, an affibody or combinations thereof, L is a linker of formula:

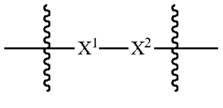

$X^1$ being linked to Ab and representing one of the following fragments:

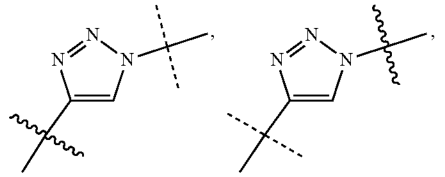

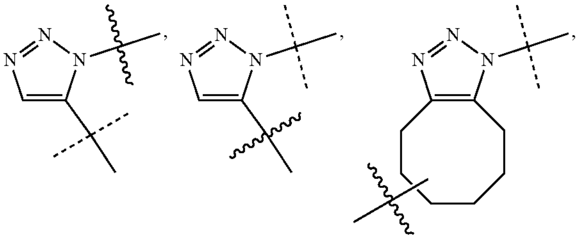

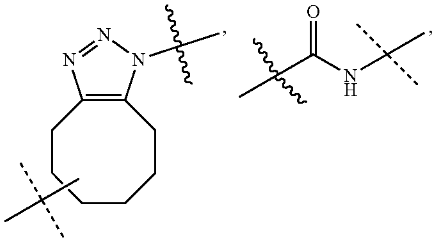

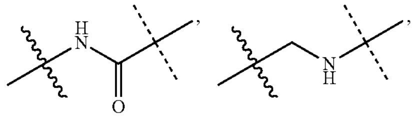

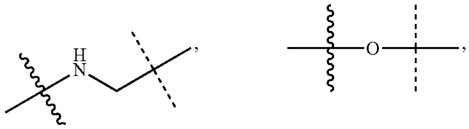

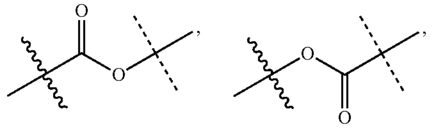

or

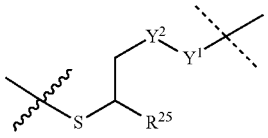

in which $Y^1$ is selected among a single bond, $CR^{26}R^{27}$, O and $NR^{28}$, $Y^2$ is selected among C═O and C═$NR^{29}$, $R^{25}$ to $R^{29}$ are independently selected among H and $C_1$-$C_6$alkyl or $R^{28}$ and $R^{25}$ form together a divalent hydrocarbon chain, advantageously comprising 1 or 2 carbon atoms, optionally substituted with one or more groups selected among oxo and $C_1$-$C_6$ alkyl, such as a group C═O, the wavy line indicates the point of attachment to Ab, and the dash line indicates the point of attachment to $X^2$, $X^2$ being linked to D and representing a single bond or a ($C_1$-$C_{20}$)-alkyl chain, preferably ($C_1$-$C_6$)-alkyl, optionally broken up and/or followed and/or replaced by one or more groups, notably one to three, selected from —O—, —O—, aryl, heteroaryl, carbocyclic, heterocyclic, —C≡C—, —C($R^a$)═C($R^b$)—, —$NR^a$—, —C(O)—, —C(S)—, —C═N—, —N═C—, —OC(O)—, —C(O)O—, —SC(O)—, —C(O)S—, —N($R^a$)C(O)— and —C(O)N($R^a$)—, the aryl, heteroaryl and heterocyclic rings being optionally substituted, $R^a$ an $R^b$ being independently H or $C_1$-$C_6$ alkyl, n is an integer between 1 and 12, D has one of the following formulas:

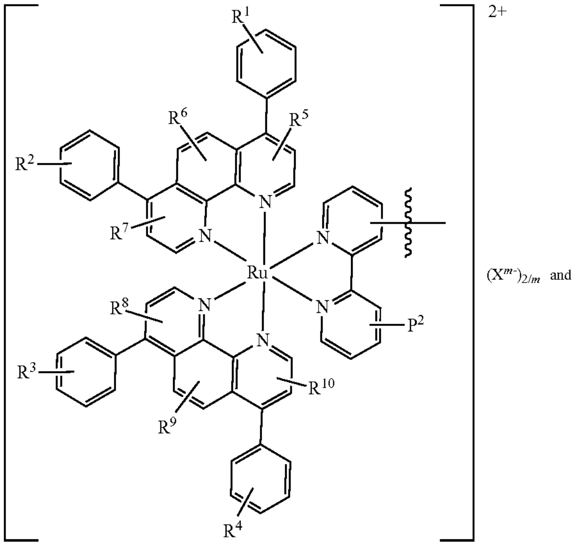

and

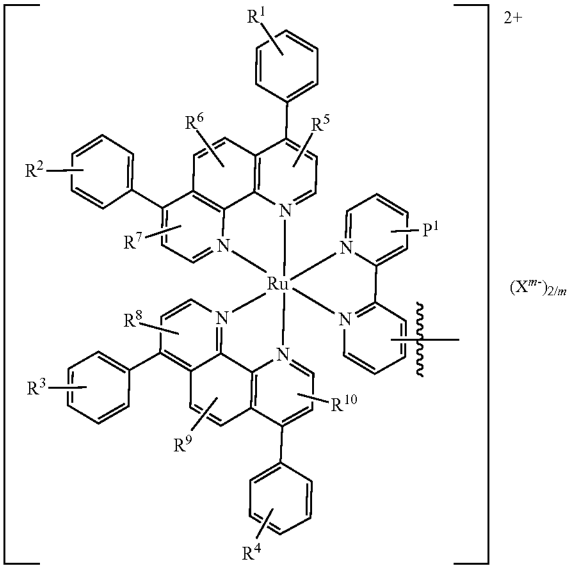

wherein $R^1$ to $R^{10}$ and $P^1$ or $P^2$ are as defined above.

According to the previous embodiment, the substituent $X^1$ in the linker corresponds to the linking moiety obtained by reaction of a binding fragment carried by Ab and a binding fragment carried by the compound of formula (I).

For example, $X^1$ can be the result of a reaction of click chemistry and thus corresponds to

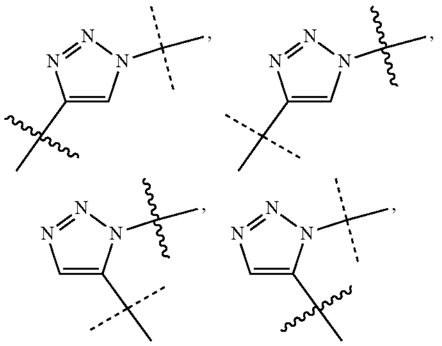

or optionally

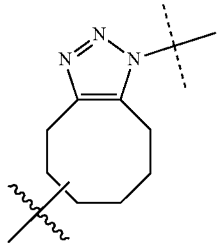

or

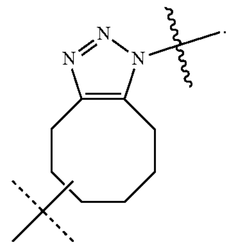

In this case, the binding fragment carried by Ab is an azide group $N_3$ and the binding fragment carried by the compound of formula (I) is a group comprising a triple bond, such as acetylene or cyclooctyne or inversely, the binding fragment carried by Ab is a group comprising a triple bond, such as acetylene or cyclooctyne, and the binding fragment carried by the compound of formula (I) is an azide group $N_3$.

$X^1$ can also results from a peptide coupling and thus corresponds to

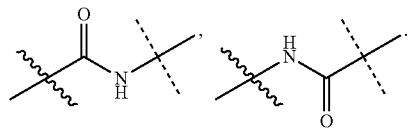

In this case, the binding fragment carried by Ab is an amine $NH_2$ and the binding fragment carried by the compound of formula (I) is a C(O)OH or a C(O)-halogen, or inversely, the binding fragment carried by Ab is a COOH or a C(O)-halogen group, and the binding fragment carried by the compound of formula (I) is a $NH_2$ group.

$X^1$ can also results from an esterification reaction and thus corresponds to

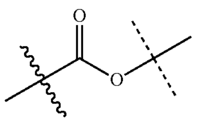

or

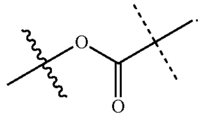

In this case, the binding fragment carried by Ab is typically an OH group and the binding fragment carried by the compound of formula (I) is a C(O)OH or a C(O)-halogen group, or inversely, the binding fragment carried by Ab is a C(O)OH or a C(O)-halogen group, and the binding fragment carried by the compound of formula (I) is a OH group.

$X^1$ can also results from an etherification and thus corresponds to

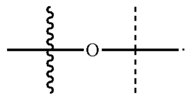

In this case, the binding fragment carried by Ab is typically an OH group and the binding fragment carried by the compound of formula (I) is a leaving group such as halogen, or inversely, the binding fragment carried by Ab is a leaving group such as halogen, and the binding fragment carried by the compound of formula (I) is an OH group.

$X^1$ can also results from a reductive amination and thus corresponds to

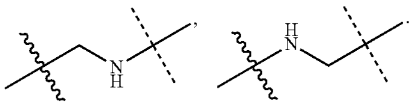

In this case, the binding fragment carried by Ab is an amine $NH_2$ and the binding fragment carried by the compound of formula (I) is a CHO group, or inversely, the binding fragment carried by Ab is a CHO group, and the binding fragment carried by the compound of formula (I) is a $NH_2$ group.

$X^1$ may also results from a reaction between a thiol group carried by Ab and a group of the following formula:

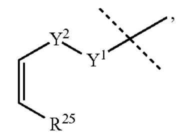

i.e. a Michael acceptor, carried by the compound of formula (I) wherein $Y^1$, $Y^2$ and $R^{25}$ are as described above. In particular, the group carried by the compound of formula (I) is a maleimidyl group of formula:

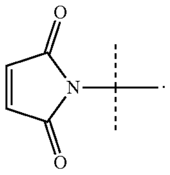

In a preferred embodiment, in the conjugate of formula (IV), Ab is an antibody.

Advantageously, in the conjugate of formula (IV), $X^1$ represent the following group:

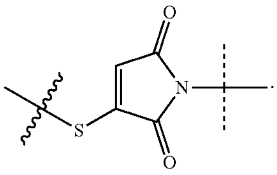

In particular, $X^2$ represents a single bond or $(C_1\text{-}C_6)$-alkyl.

n is preferably an integer 1, 2, 3, 4, 5 or 6, such as 1.

Ab is preferably selected among an antibody (e.g. a monoclonal antibody), an antigen binding fragment thereof (e.g. a nanobody) or an affibody, wherein said antibody, antigen or affibody may be grafted with a peptide chain.

Pharmaceutical Composition

The present invention also relates to a pharmaceutical composition comprising at least one pharmaceutically acceptable excipient and at least one compound of formula (I) as described above or a pharmaceutically acceptable salt and/or solvate thereof.

Preferably, said compound is not:

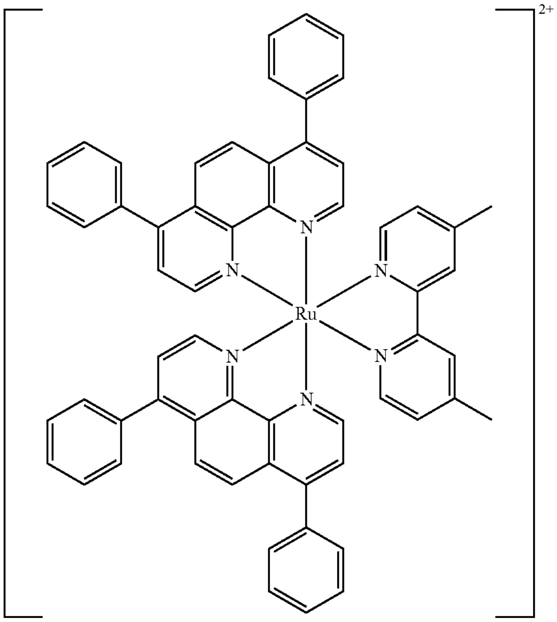

$(PF_6^-)_2$,

-continued
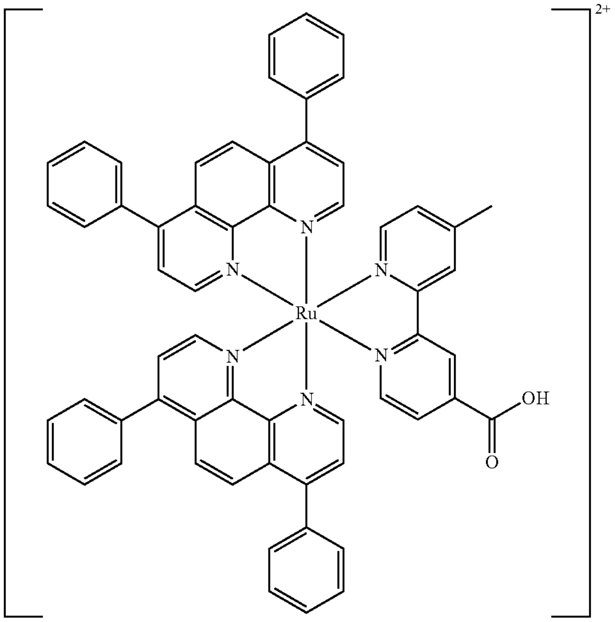
$(PF_6^-)_2$,
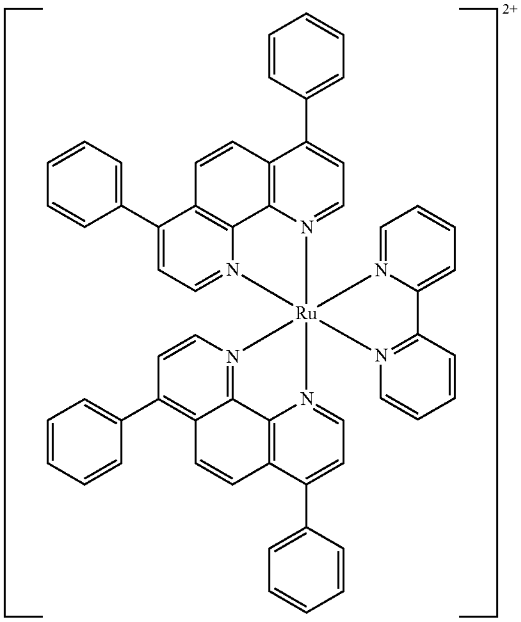
$(Cl^-)_2$,

-continued
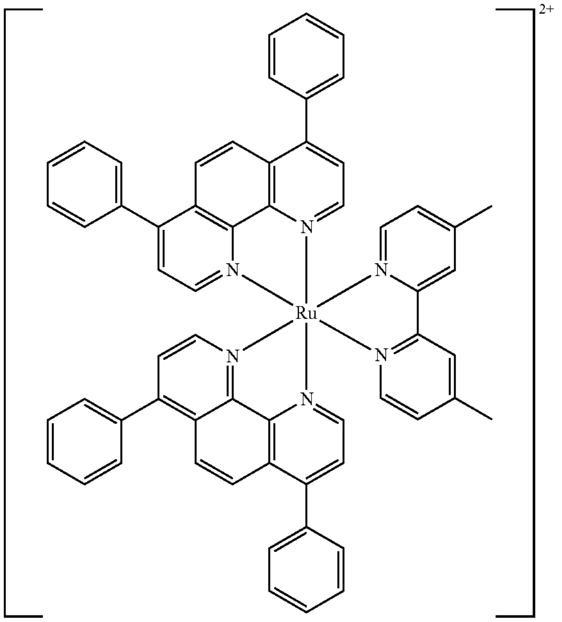
(Cl⁻)₂,
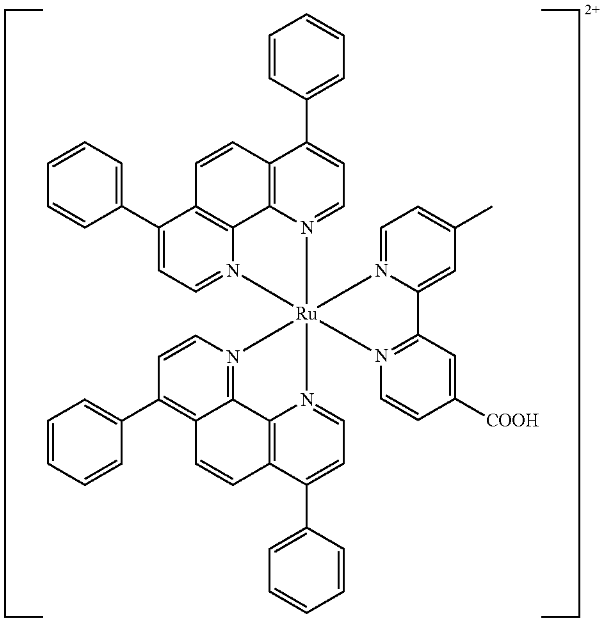
(Cl⁻)₂,

-continued
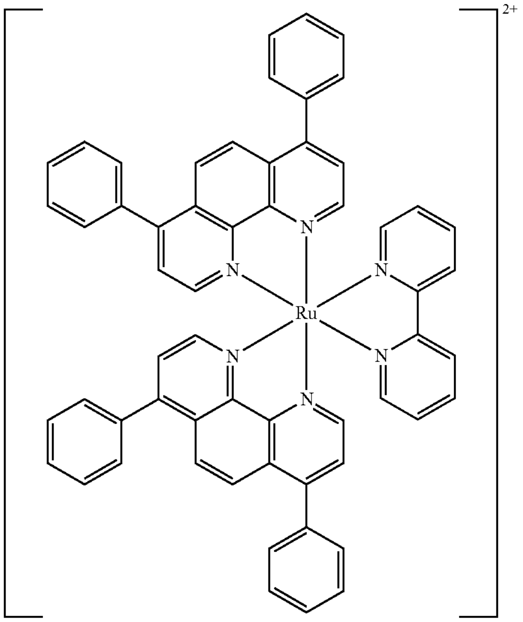
$(PF_6^-)_2$,
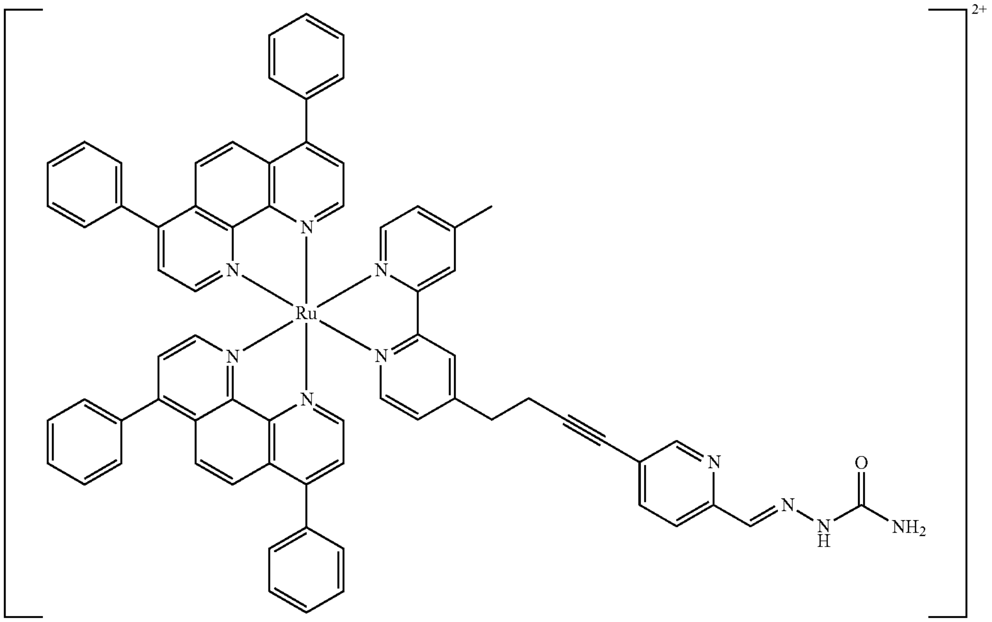
$(Cl^-)_2$,

-continued
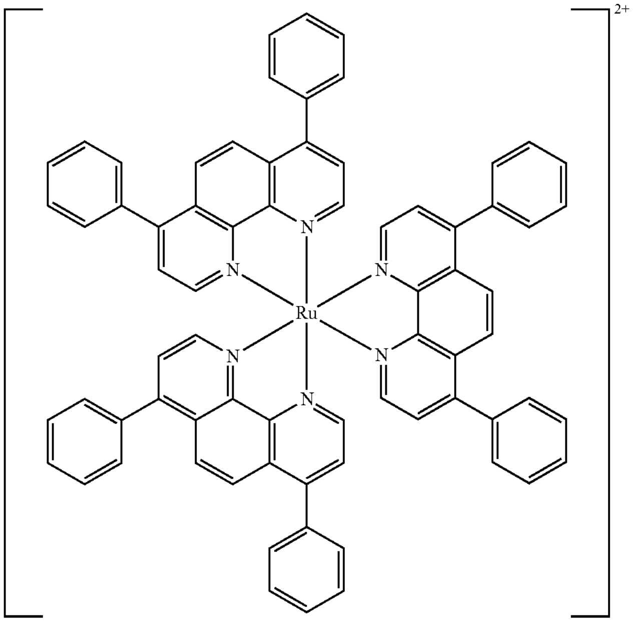
$(X^-)_2$
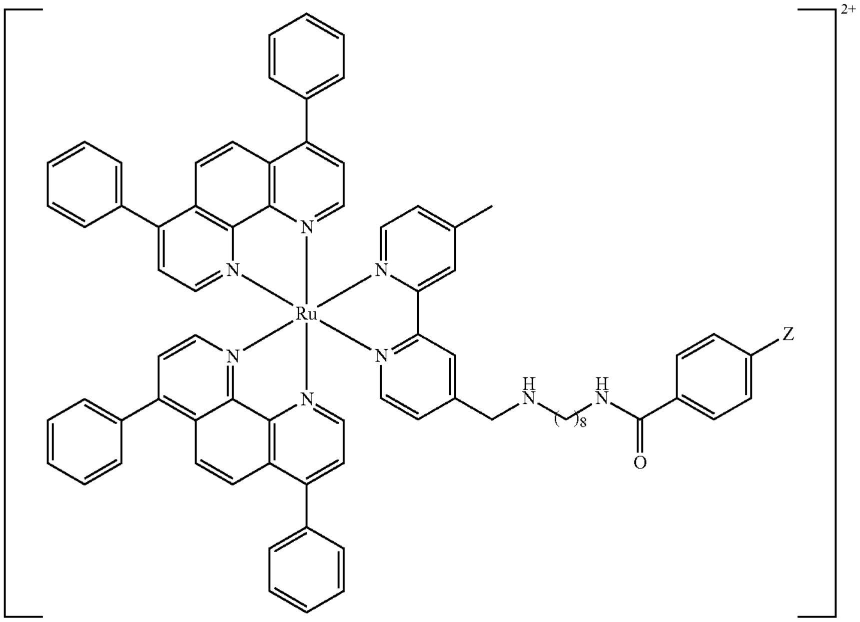
$(X^-)_2$ with
Z = 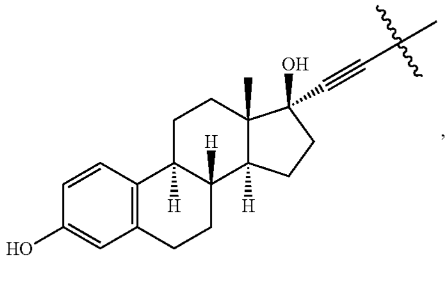 ,

-continued
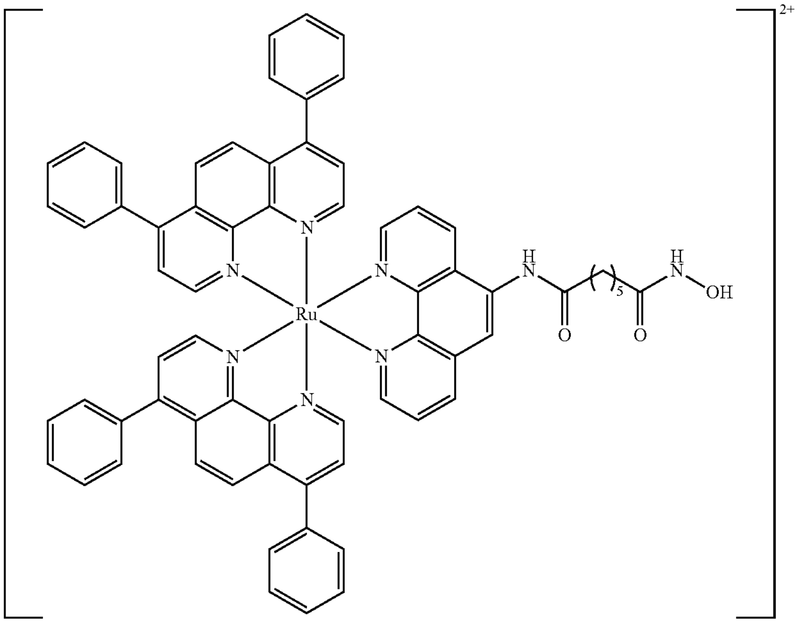
$(X^{-})_2$,
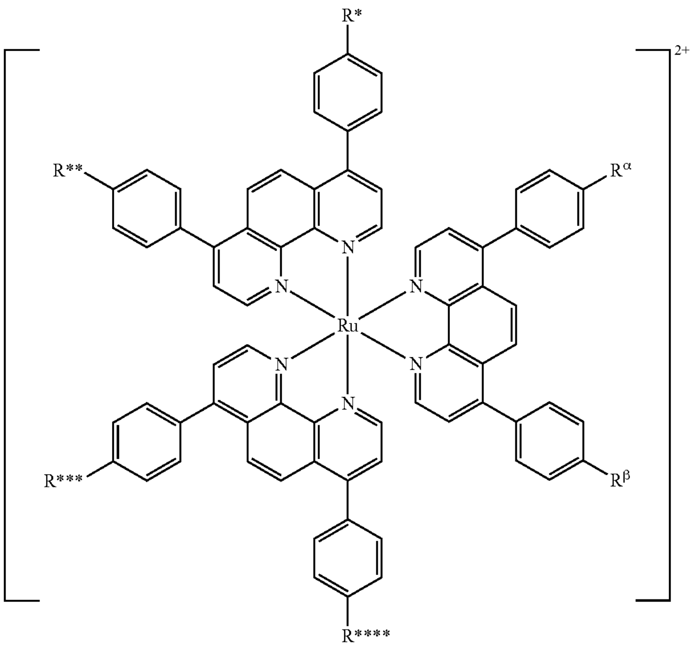
$(X^{-})_2$,

-continued
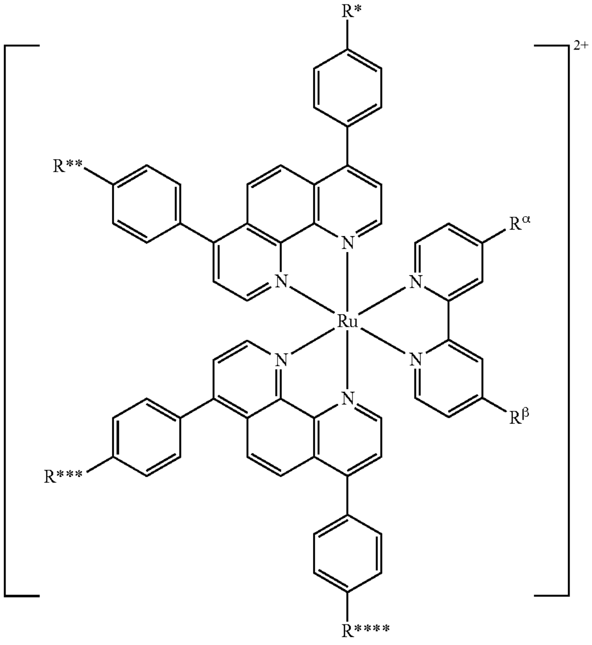
$(X^-)_2$,
in which of $R^\alpha$, $R^\beta$, R*, R, R* and R**** are each independently H, $CH_3$, COOH or $NH_2$, provided that at least one or two of $R^\alpha$ and $R^\beta$ is COOH or $NH_2$,
-continued
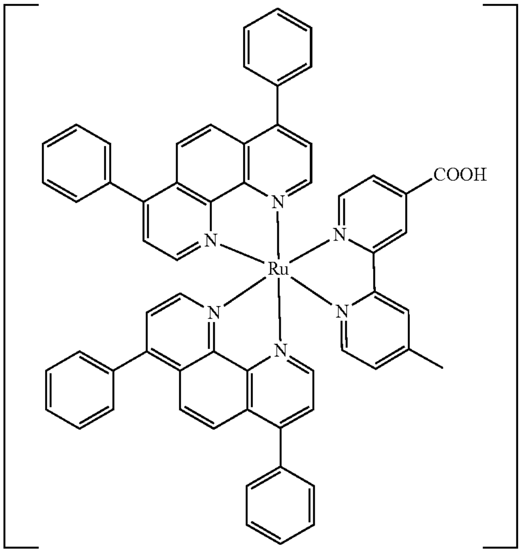
$(Cl^-)_2$
,
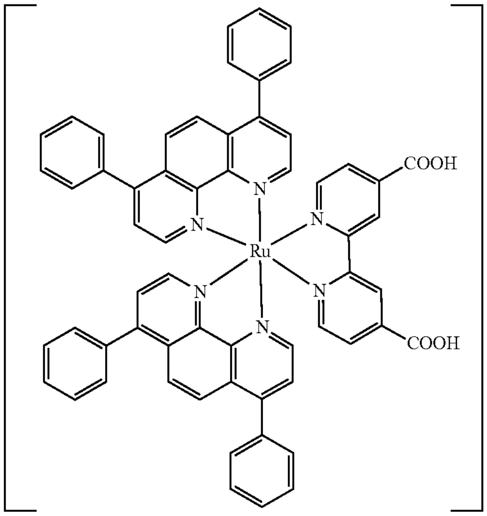
$(Cl^-)_2$, and -continued

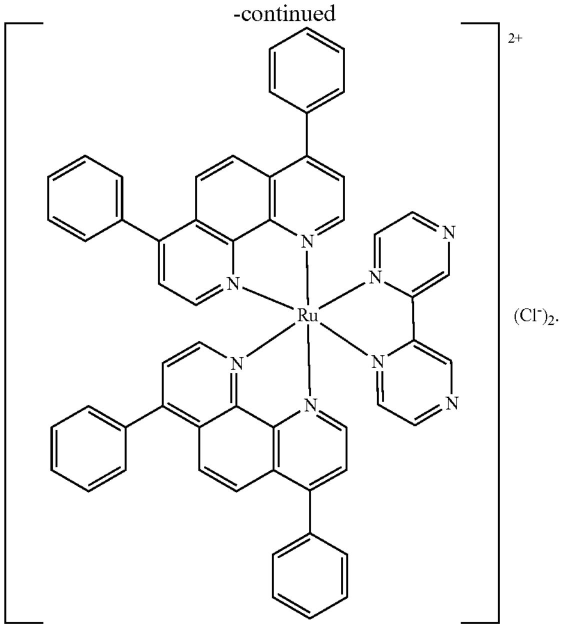

$(Cl^-)_2$.

The present invention also relates to a pharmaceutical composition comprising at least one conjugate as described above, such as a conjugate of formula (IV), or a pharmaceutically acceptable salt and/or solvate thereof, and at least one pharmaceutically acceptable excipient.

The pharmaceutical compositions of the invention can be intended to oral or parenteral (e.g. subcutaneous, intramuscular, intravenous) administration, preferably oral or intravenous administration. The active ingredient can be administered in unit forms for administration, mixed with conventional pharmaceutical carriers, to animals, preferably mammals including humans.

For oral administration, the pharmaceutical composition can be in a solid or liquid (solution or suspension) form.

A solid composition can be in the form of tablets, gelatin capsules, powders, granules and the like. In tablets, the active ingredient can be mixed with pharmaceutical vehicle(s) such as gelatin, starch, lactose, magnesium stearate, talc, gum arabic and the like before being compressed. The tablets may be further coated, notably with sucrose or with other suitable materials, or they may be treated in such a way that they have a prolonged or delayed activity. In powders or granules, the active ingredient can be mixed or granulated with dispersing agents, wetting agents or suspending agents and with flavor correctors or sweeteners. In gelatin capsules, the active ingredient can be introduced into soft or hard gelatin capsules in the form of a powder or granules such as mentioned previously or in the form of a liquid composition such as mentioned below.

A liquid composition can contain the active ingredient together with a sweetener, a taste enhancer or a suitable coloring agent in a solvent such as water. The liquid composition can also be obtained by suspending or dissolving a powder or granules, as mentioned above, in a liquid such as water, juice, milk, etc. It can be for example a syrup or an elixir.

For parenteral administration, the composition can be in the form of an aqueous suspension or solution which may contain suspending agents and/or wetting agents. The composition is advantageously sterile. It can be in the form of an isotonic solution (in particular in comparison to blood).

The compounds of the invention can be used in a pharmaceutical composition at a dose ranging from 0.01 mg to 1000 mg a day, administered in only one dose once a day or in several doses along the day, for example twice a day in equal doses. The daily administered dose is advantageously comprised between 5 mg and 500 mg, and more advantageously between 10 mg and 200 mg. However, it can be necessary to use doses out of these ranges, which could be noticed by the person skilled in the art.

Treatment

The compound of formula (I), or a pharmaceutically acceptable salt and/or solvate thereof, is useful as a photosensitizer agent in photodynamic therapy. It is particularly intended to treat by photodynamic therapy a disease selected from cancer, such as lung cancer, bladder cancer, oesophageal cancer, colon cancer, stomach cancer, liver cancer, skin cancer, ovarian cancer, pancreatic cancer, head and neck cancer, or brain cancer; bacterial infection, such as sinusitis, diabetic feet, burned wounds; fungal infection, such as mycoses; viral infection such as herpes; and skin disorders, such as acne, port wine stains.

The pharmaceutical compositions according to the present invention are advantageously useful as a photosensitizer agent in photodynamic therapy, notably intended to treat a disease selected from cancer, such as lung cancer, bladder cancer, oesophageal cancer, colon cancer, stomach cancer, liver cancer, skin cancer, ovarian cancer, pancreatic cancer, head and neck cancer, or brain cancer; bacterial infection, such as sinusitis, diabetic feet, burned wounds; fungal infection, such as mycoses; viral infection such as herpes; and skin disorders, such as acne, port wine stains.

EXAMPLES

1) Synthesis

Materials

Figure 1:
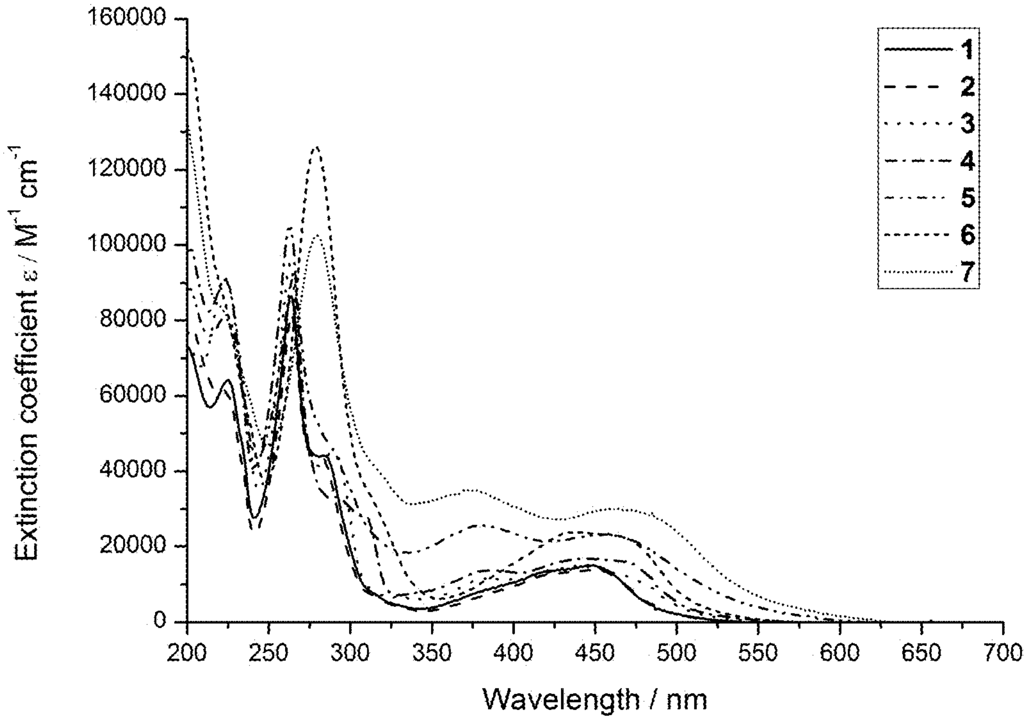
FIG. 1. Measured UV/Vis spectra of the complexes 1-7 in $CH_3CN$.

All chemicals were obtained from commercial sources and were used without further purification. Solvents were dried over molecular sieves if necessary. The Ru(II) complexes Dichlorobis(1,10-phenanthroline)ruthenium(II) $[RuCl_2(phen)_2]$ and Dichlorobis(4,7-Diphenyl-1,10-phenanthroline)ruthenium(II) $[RuCl_2(bphen)_2]$ were synthesised as previously published using the respective ligands (Sullivan, B. et al., 1978). The substituted bipyridine ligands 2,2'-Bipyridine-4,4'-dicarbonitrile, (E,E')-4,4'-Bis(N,N-dimethylaminovinyl)-2,2'-bipyridine and 2,2'-Bipyridine-4,4'-dicarboxaldehyde were synthesised as reported (Wuest, J. D. 2011 and Le Bozec, H., 2001). The Ru(II) complexes $[Ru(phen)_2(dppz\text{-}7\text{-}aminomethyl)](PF_6)_2$ was synthesized as previously reported (Gasser, G. et al., 2015).

Instrumentation and Methods $^1H$ and $^{13}C$ NMR spectra were recorded on a Bruker 400 MHz NMR spectrometer. ESI-MS experiments were carried out using a LTQ-Orbitrap XL from Thermo Scientific (Thermo Fisher Scientific, Courtaboeuf, France) and operated in positive ionization mode, with a spray voltage at 3.6 kV. No Sheath and auxiliary gas was used. Applied voltages were 40 and 100 V for the ion transfer capillary and the tube lens, respectively. The ion transfer capillary was held at 275° C. Detection was achieved in the Orbitrap with a resolution set to 100,000 (at m/z 400) and a m/z range between 150-2000 in profile mode. Spectrum was analyzed using the acquisition software XCalibur 2.1 (Thermo Fisher Scientific, Courtaboeuf, France). The automatic gain control (AGC) allowed accumulation of up to $2*10^5$ ions for FTMS scans, Maximum injection time was set to 300 ms and 1 µscan was acquired. 10 µL was injected using a Thermo Finnigan Surveyor HPLC system (Thermo Fisher Scientific, Courtaboeuf, France) with a continuous infusion of methanol at 100 $\mu L \cdot min^{-1}$. For analytic and preparative HPLC the following system has been used: 2× Agilent G1361 1260 Prep Pump system with Agilent G7115A 1260 DAD WR Detector equipped with an Agilent Pursuit XRs 5C18 (Analytic: 100 Å, C18 5 µm 250×4.6 mm, Preparative: 100 Å, C18 5 µm 250×300 mm) Column and an Agilent G1364B 1260-FC fraction collector. The solvents (HPLC grade) were Millipore water (0.1% TFA, solvent A) and acetonitrile (0.1% TFA, solvent B). The sample was dissolved in 1:1 (v/v) $CH_3CN/H_2O$ 0.1% TFA solution and filtered through a 0.2 µm membrane filter. Gradient: 0-3 minutes: isocratic 95% A (5% B); 3-17 minutes: linear gradient from 95% A (5% B) to 0% A (100% B); 17-25 minutes: isocratic 0% A (100% B). The flow rate was 1 mL/min (for preparative purposes: 20 mL/min) and the chromatogram was detected at 250 nm, 350 nm, 450 nm.

Synthesis of Ruthenium Complexes (Bipyridine)bis(1,10-phenanthroline)ruthenium(II) hexafluorophosphate $[Ru(bpy)(phen)_2](PF_6)_2$ (1) (Comparative)

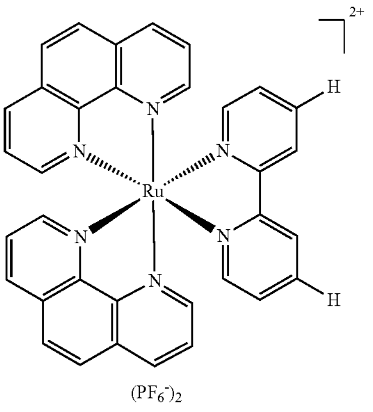

The synthesis of $[Ru(bpy)(phen)_2](PF_6)_2$ is already published in Crosby, G. et al., 1976.

(4,4'-Dimethyl-2,2'-bipyridine)bis(1,10-phenanthroline)ruthenium(II)hexafluorophosphate $[Ru(Me\text{-}bpy)(phen)_2](PF_6)_2$ (2) (Comparative)

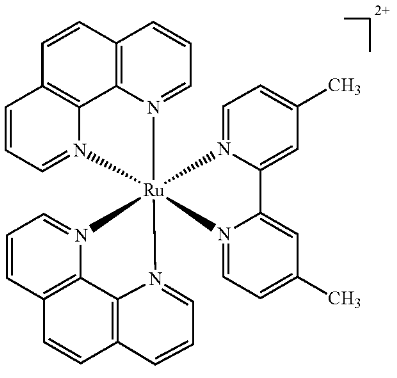

The synthesis of $[Ru(Me\text{-}bpy)(phen)_2](PF_6)_2$ is already published in Jones Jr, W. E. et al., 1989.

(4,4'-Dibromo-2,2'-bipyridine)bis(1,10-phenanthroline)ruthenium(II) hexafluorophosphate$[Ru(Br\text{-}bpy)(phen)_2](PF_6)_2$ (3) (Comparative)

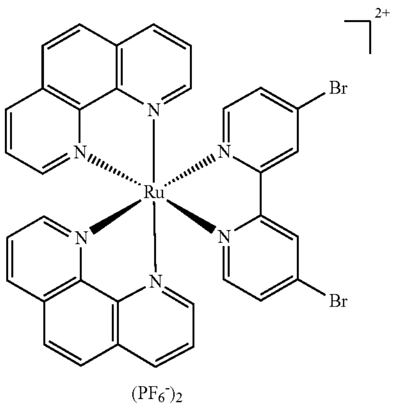

$RuCl_2(phen)_2$ (150 mg, 0.28 mmol, 1.0 equiv.) and 4,4'-Dibromo-2,2'-bipyridine (105 mg, 0.34 mmol, 1.2 equiv.) were dissolved in a 1:1 mixture of $H_2O$/EtOH (40 mL) and were refluxed for 18 h under $N_2$ atmosphere. The solvent was evaporated and the residue redissolved in 5 mL of $H_2O$. A saturated, aq. $NH_4PF_6$ solution was added and the resulting precipitate was collected by vacuum filtration. The solid was washed with $H_2O$ (50 mL) and $Et_2O$ (50 mL). The product was isolated by column chromatography on silica gel with an $CH_3CN$/aq. $KNO_3$ (0.4 M) solution (10:1). The fractions containing the product were united and the solvent was removed. The residue was dissolved in $CH_3CN$ and undissolved $KNO_3$ was removed by filtration. The solvent was removed again and the product was dissolved in $H_2O$ (50 mL). Upon addition of $NH_4PF_6$ the product precipitated as a $PF_6$ salt. The solid was obtained by filtration and was washed with $H_2O$ (50 mL) and $Et_2O$ (50 mL). The product was dried in high vacuum. Yield: 78%. $^1H$ NMR (500 MHz, $CD_3CN$) δ=8.76 (2H, d, $^4J$=2.0 Hz), 8.68 (2H, dd, $^3J$=8.3 Hz, $^4J$=1.3 Hz), 8.55 (2H, dd, $^3J$=8.3 Hz, $^4J$=1.3 Hz), 8.27 (2H, d, $^3J$=8.9 Hz), 8.25 (2H, dd, $^3J$=5.3 Hz, $^4J$=1.3 Hz), 8.22 (2H, d, $^3J$=8.9 Hz), 7.84 (2H, dd, $^3J$=5.3 Hz, $^4J$=1.3 Hz), 7.81 (2H, dd, $^3J$=8.3 Hz, $^3J$=5.2 Hz), 7.55 (2H, dd, $^3J$=8.3 Hz, $^3J$=5.3 Hz), 7.50 (2H, d, $^3J$=6.1 Hz), 7.47 (2H, dd, $^3J$=6.1 Hz, $^4J$=2.0 Hz). $^{13}C$ NMR (125 MHz, $CD_3CN$) δ=158.3, 154.0, 153.9, 153.6, 148.7, 148.4, 138.0, 137.9, 134.7, 132.0, 132.0, 131.7, 129.1, 129.0, 129.0, 127.0, 126.9. HR-MS (ESI+m/z): Calcd. [M-2PF 6] 2+: 386.96526; found: 386.96576. EA (%): Calcd. for ($C_{34}H_{22}Br_2F_{12}N_6P_2Ru$): C, 38.33; H, 2.08; N, 7.89; found. C, 38.62; H, 2.01; N, 7.78.

(2,2'-bipyridine-4,4'-carboxamide)bis(1,10-phenanthroline)ruthenium(II) hexafluorophosphate [Ru(CONH2-bpy)(phen)$_2$]($PF_6$)$_2$ (4) (Comparative)

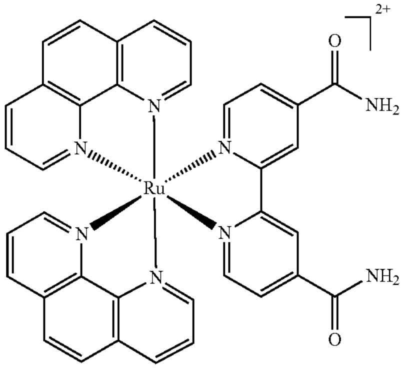

$(PF_6^-)_2$ $RuCl_2$(phen)$_2$ (150 mg, 0.28 mmol, 1.0 equiv.) and 2,2'-Bipyridine-4,4'-dicarbonitrile (64 mg, 0.31 mmol, 1.1 equiv.) were dissolved in a 1:1 mixture of $H_2O$/EtOH (30 mL) and were refluxed for 18 h under $N_2$ atmosphere. The solvent was evaporated and the residue redissolved in 5 mL of $H_2O$. A saturated, aq. $NH_4PF_6$ solution was added and the resulting precipitate was collected by vacuum filtration. The solid was washed with $H_2O$ (50 mL) and $Et_2O$ (50 mL). The product was purified by column chromatography on silica gel with an $CH_3CN$/aq. $KNO_3$ (0.4 M) solution (10:1). The fractions containing the product were united and the solvent was removed. The residue was dissolved in $CH_3CN$ and undissolved $KNO_3$ was removed by filtration. The solvent was removed again and the product was dissolved in $H_2O$ (50 mL). Upon addition of $NH_4PF_6$ the product precipitated as a $PF_6$ salt. The solid was obtained by filtration and was washed with $H_2O$ (50 mL) and $Et_2O$ (50 mL). The product was dried in high vacuum. Yield: 16%. $^1H$ NMR (400 MHz, $CD_3CN$) δ=8.97 (2H, s), 8.67 (2H, d, $^3J$=8.3 Hz), 8.58 (2H, d, $^3J$=8.3 Hz), 8.30-8.22 (4H, m), 8.18 (2H, d, $^3J$=5.2 Hz), 7.87-7.84 (4H, m), 7.79 (2H, dd, $^3J$=8.3 Hz, $^3J$=5.2 Hz), 7.61-7.57 (4H, m), 7.25 (2H, s), 6.48 (2H, s). $^{13}C$ NMR (100 MHz, $CD_3CN$) δ=165.7, 158.8, 154.0, 153.9, 153.5, 148.6, 148.3, 143.0, 138.2, 138.0, 132.1, 132.0, 129.1, 129.0, 127.0, 127.0, 126.0, 123.1. HR-MS (ESI+m/z): Calcd. [M-2PF 6] 2+: 352.06056; found: 352.06063. EA (%): Calcd. for ($C_{36}H_{26}F_{12}N_8O_2P_2Ru$): C, 43.52; H, 2.64; N, 11.28; found. C, 43.33; H, 2.47; N, 11.15.

((E,E')-4,4'-Bis(N,N'-dimethylaminovinyl)-2,2'-bi-pyridine)bis(1,10-phenanthroline)ruthenium(II) hexafluorophosphate [Ru($Me_2$Nvin-bpy)(phen)$_2$]($PF_6$)$_2$ (5) (Comparative)

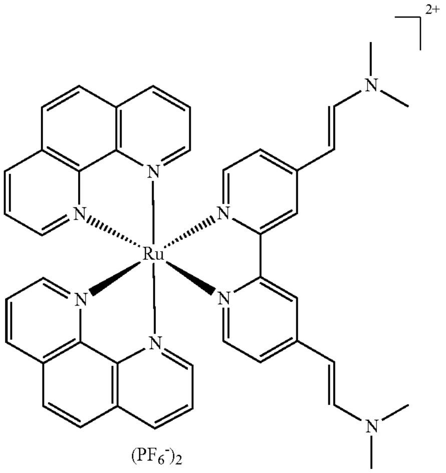

$(PF_6^-)_2$

[Ru(Me-bpy)(phen)$_2$]($PF_6$)$_2$ (2) (100 mg, 0.11 mmol, 1.0 equiv.) was dissolved in dry DMF (1.5 mL) and Cert-Butoxy bis(dimethylamino)methane (0.2 mL, 0.97 mmol, 8.8 equiv.) was added. The mixture was heated at 140° C. for 16 h under $N_2$ atmosphere. The solution was cooled down and an aq. solution of $NH_4PF_6$ was added. The resulting precipitate was collected by vacuum filtration and the solid was washed with $H_2O$ (50 mL) and $Et_2O$ (50 mL). The product was isolated via fractionated precipitation from $CH_3CN$ by adding dropwise $Et_2O$ and afterwards dried in high vacuum. Yield: 41%. $^1H$ NMR (400 MHz, $CD_3CN$) δ=8.61 (2H, dd, $^3J$=8.3 Hz, $^4J$=1.3 Hz), 8.48 (2H, dd, $^3J$=8.3 Hz, $^4J$=1.3 Hz), 8.38 (2H, dd, $^3J$=5.3 Hz, $^4J$=1.3 Hz), 8.25-8.18 (4H, m), 8.07 (2H, d, $^4J$=2.2 Hz), 7.87 (2H, dd, $^3J$=5.3 Hz, $^4J$=1.3 Hz), 7.82 (2H, dd, $^3J$=8.2 Hz, $^3J$=5.3 Hz), 7.52-7.48 (4H, m), 6.99 (2H, d, $^3J$=6.2 Hz), 6.77 (2H, dd, $^3J$=6.2 Hz, $^4J$=2.1 Hz), 5.08 (2H, d, $^3J$=13.4 Hz), 2.94 (12H, s). $^{13}C$ NMR (100 MHz, $CD_3CN$) δ=157.6, 153.5, 153.5, 151.6, 150.6, 149.2, 149.1, 147.8, 137.0, 137.0, 131.9, 131.9, 129.0, 129.0, 126.9, 126.7, 120.3, 117.1, 92.9, 40.1. HR-MS (ESI+m/z): Calcd. [M-2PF 6] 2+: 378.11260; found: 378.11289. EA (%): Calcd. for ($C_{42}H_{38}F_{12}N_8P_2Ru$): C, 48.24; H, 3.66; N, 10.71; found: C, 47.97; H, 3.59; N, 10.76.

(4,4'-Dimethyl-2,2'-bipyridine)bis(4,7-diphenyl-1,10-phenanthroline)ruthenium(II) hexafluorophosphate [Ru(Me-bpy)(bphen)$_2$](PF$_6$)$_2$ (6)

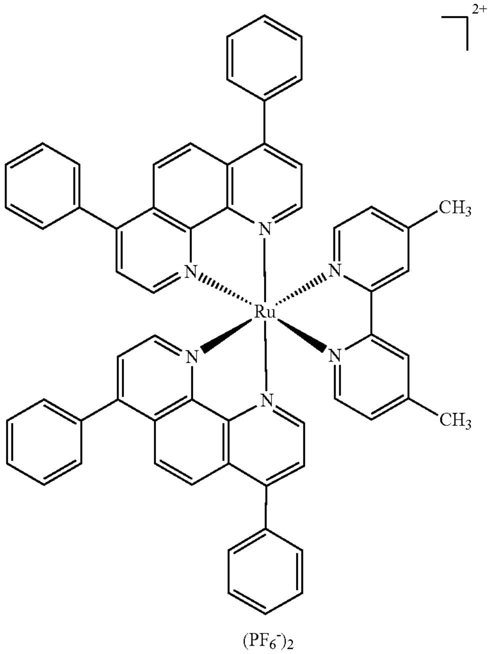

The synthesis of [Ru(Me-bpy)(bphen)$_2$](PF$_6$)$_2$ is already published (Mazuryk, O. et al., 2014) but in this study another synthetic route was employed. RuCl$_2$(bphen)$_2$ (200 mg, 0.24 mmol, 1.0 equiv.) and 4,4'-Dimethyl-2,2'-bipyridine (53 mg, 0.29 mmol, 1.2 equiv.) were dissolved in a 1:1 mixture of $H_2O$/EtOH (10 mL) and were refluxed for 18 h under $N_2$ atmosphere. The solvent was evaporated and the residue redissolved in 10 mL of $H_2O$. A saturated, aq. $NH_4PF_6$ solution was added and the suspension was sonicated. 60 mL of $H_2O$ were added and the resulting precipitate was collected by vacuum filtration. The solid was washed with $H_2O$ (50 mL) and $Et_2O$ (50 mL). The product was dried in high vacuum. Yield: 93%. $^1$H NMR (400 MHz, $CD_3CN$) δ=8.44 (2H, s), 8.29 (2H, d, $^3$J=5.5 Hz), 8.22-8.16 (m, 4H), 8.10 (2H, d, $^3$J=5.5 Hz), 7.75 (2H, d, $^3$J=5.5 Hz), 7.72-7.53 (24H, m), 7.21 (2H, d, $^3$J=5.8, $^4$J=1.7 Hz), 2.56 (6H, s). $^{13}$C NMR (125 MHz, $CD_3CN$) δ=157.7, 153.1, 152.9, 152.2, 151.4, 149.9, 149.8, 149.5, 149.4, 136.7, 136.7, 130.8, 130.7, 130.7, 130.6, 130.6, 130.1, 130.1, 130.1, 129.9, 129.9, 129.1, 127.1, 127.0, 127.0, 126.9, 125.8, 21.3. HR-MS (ESI+m/z): Calcd. [M-2PF 6] 2+: 475.13300; found: 475.13388. EA (%): Calcd. ($C_{60}H_{44}F_{12}N_6P_2Ru$)×($H_2O$)$_2$: C, 56.47; H, 3.79; N, 6.59; found: C, 56.46; H, 3.85; N, 6.11.

((E,E')-4,4'-Bis(N,N'-dimethylaminovinyl)-2,2'-bipyridine)bis(4,7-diphenyl-1,10-phenanthroline)ruthenium(II) hexafluorophosphate [Ru(Me$_2$Nvin-bpy)(bphen)$_2$](PF$_6$)$_2$ (7)

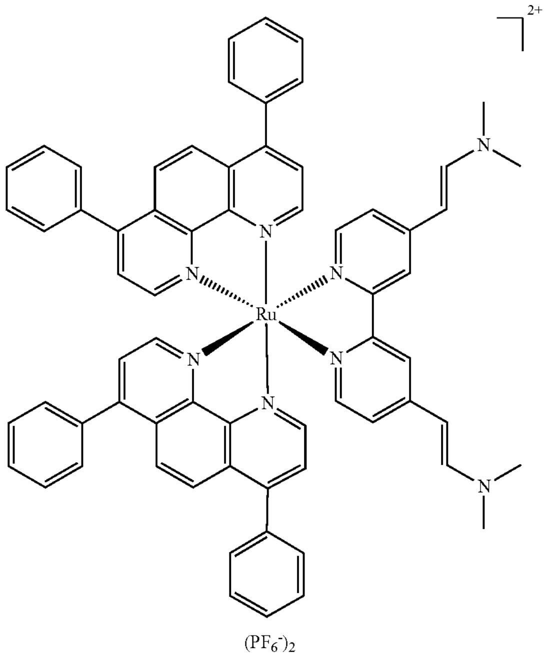

[Ru(Me-bpy)(bphen)$_2$](PF$_6$)$_2$ (7) (150 mg, 0.12 mmol, 1.0 equiv.) was dissolved in dry DMF (1.5 mL) and tert-Butoxy bis(dimethylamino)methane (0.3 mL, 1.45 mmol, 12.1 equiv.) was added. The mixture was heated at 140° C. for 18 h under $N_2$ atmosphere. After this time, more tert-Butoxy bis(dimethylamino)methane (0.4 mL, 1.94 mmol, 16.2 equiv.) was added the mixture was heated at 145° C. for 72 h under $N_2$ atmosphere. The solution was cooled down and an aq. solution of $NH_4PF_6$ was added. The resulting precipitate was collected by vacuum filtration and the solid was washed with $H_2O$ (50 mL) and $Et_2O$ (50 mL). The product was isolated via fractionated precipitation from $CH_3CN$ by adding dropwise $Et_2O$ and afterwards dried in high vacuum. Yield: 67%. $^1$H NMR (500 MHz, $CD_3CN$) δ=8.47 (2H, d, $^3$J=5.5 Hz), 8.22-8.13 (8H, m), 8.09 (2H, d, $^3$J=5.5 Hz), 7.80 (2H, d, $^3$J=5.5 Hz), 7.69-7.52 (22H, m), 7.21 (2H, d, $^3$J=6.3 Hz), 6.87 (2H, dd, $^3$J=6.3 Hz, $^4$J=2.0 Hz), 5.13 (2H, d, $^3$J=13.3 Hz), 2.96 (12H, s). $^{13}$C NMR (125 MHz, $CD_3CN$) δ=157.4, 152.9, 152.7, 151.5, 150.6, 149.7, 149.6, 149.2, 149.2, 149.2, 149.2, 149.2, 147.7, 136.9, 136.8, 130.8, 130.7, 130.7, 130.5, 130.5, 130.1, 130.0, 130.0, 129.7, 129.7, 127.1, 126.9, 126.8, 126.8, 120.2, 117.0, 92.7, 40.7. HR-MS (ESI+m/z): Calcd. [M-2PF 6] 2+: 530.17520; found: 530.17584. EA (%): Calcd. for ($C_{66}H_{64}F_{12}N_8P_2Ru$)×($H_2O$) 0.5: C, 58.32; H, 4.08; N, 8.24; found: C, 58.17; H, 3.83; N, 8.66.

(4'-Methyl-2,2'-bipyridinyl-4-aldehyde)bis(4,7-diphenyl-1,10-phenanthroline)ruthenium(II) hexafluorophosphate (8)

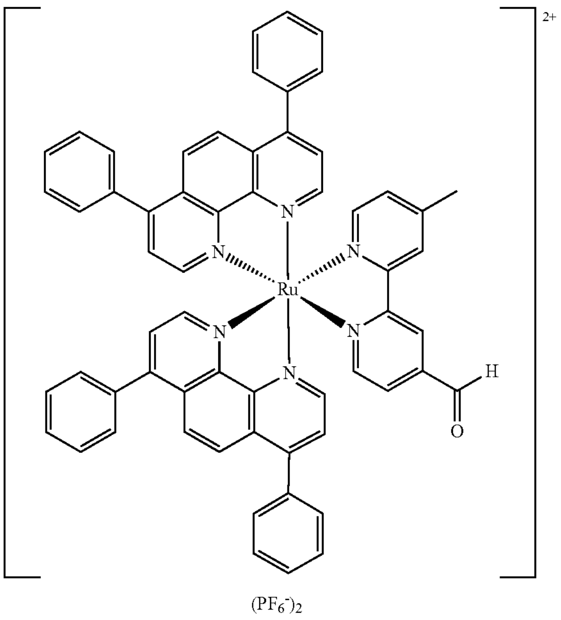

Ru(bphen)$_2$Cl$_2$ (200 mg, 1.0 equiv.) and 4'-Methyl-2,2'-bipyridinyl-4-aldehyde (57 mg, 1.2 equiv.) were dissolved in a 1:1 mixture of $H_2O$/EtOH (10 mL) and were refluxed overnight under $N_2$ atmosphere. The solvent was evaporated and the residue redissolved in 10 mL of $H_2O$. A saturated, aq. $NH_4PF_6$ solution was added and the resulting precipitate was collected by vacuum filtration. The solid was washed with $H_2O$ (50 mL) and $Et_2O$ (50 mL). The product was dried in high vacuum. Yield: 79%. $^1$H NMR (400 MHz, $CD_3CN$) δ=10.18 (s, 1H), 8.93 (s, 1H), 8.64 (s, 1H), 8.29 (1H, d, J=5.5 Hz), 8.27 (1H, d, J=5.5 Hz), 8.20 (4H, d, J=2.2 Hz), 8.15 (1H, d, J=5.8 Hz), 8.11 (1H, d, J=3.2 Hz), 8.10 (1H, d, J=3.2 Hz), 7.78-7.69 (m, 4H), 7.67-7.57 (m, 22H), 7.29-7.27 (m, 1H), 2.60 (s, 3H). $^{13}$C NMR (100 MHz, $CD_3CN$) δ=191.5, 160.3, 157.0, 154.9, 153.2, 153.1, 152.9, 152.3, 151.8, 150.4, 150.3, 150.2, 149.4, 149.3, 149.2, 148.9, 142.8, 136.6, 136.6, 130.8, 130.7, 130.7, 130.6, 130.1, 130.1, 130.0, 129.9, 129.8, 127.2, 127.0, 126.7, 126.2, 122.9, 21.2. ESI-HRMS (pos. detection mode): calcd for C60H42N6O1Ru m/z $[M]^{2+}$ 482.1236; found: 482.1226. Elemental analysis calcd for C60H42F12N6O1P2Ru (%): C, 57.47; H, 3.38; N, 6.70; found: C, 57.56; H, 3.32; N, 6.64.

(4'-Methyl-2,2'-bipyridinyl-4-carboxylic acid)bis(4,7-diphenyl-1,10-phenanthroline) ruthenium(II) hexafluorophosphate (9)

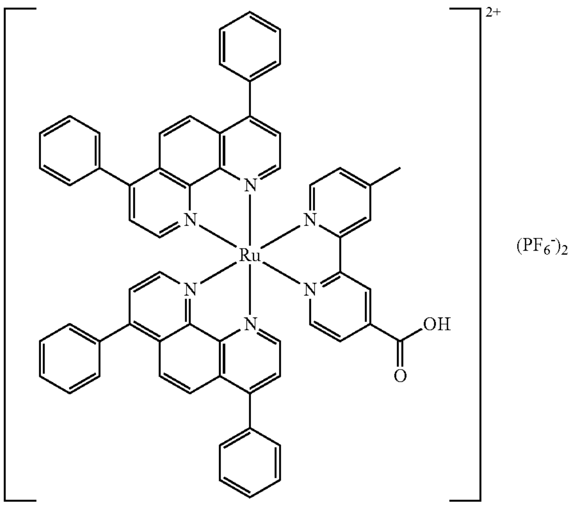

Ru(bphen)$_2$Cl$_2$ (200 mg, 1.0 equiv.) and 4'-Methyl-2,2'-bipyridinyl-4-carboxylic acid (57 mg, 1.2 equiv.) were dissolved in a 1:1 mixture of $H_2O$/EtOH (10 mL) and were refluxed overnight under $N_2$ atmosphere. The solvent was evaporated and the residue redissolved in 10 mL of $H_2O$. A saturated, aq. $NH_4PF_6$ solution was added and the resulting precipitate was collected by vacuum filtration. The solid was washed with $H_2O$ (50 mL) and $Et_2O$ (50 mL). The product was dried in high vacuum. Yield: 83%. $^1$H NMR (400 MHz, $CD_3CN$) δ=9.09 (s, 1H), 8.67 (s, 1H), 8.35 (1H, d, J=5.5 Hz), 8.32 (1H, d, J=5.5 Hz), 8.23 (2H, d, J=1.5 Hz), 8.22 (2H, d, J=2.0 Hz), 8.16 (2H, d, J=5.5 Hz), 8.03 (1H, d, J=5.8 Hz), 7.82-7.74 (m, 4H), 7.67-7.62 (m, 22H), 7.28 (1H, d, J=5.5 Hz), 2.58 (s, 3H). $^{13}$C NMR (100 MHz, $CD_3CN$) δ=166.5, 159.2, 157.3, 153.8, 153.1, 153.0, 152.2, 151.7, 150.1, 150.1, 150.0, 150.0, 149.4, 149.3, 149.3, 149.1, 142.9, 136.7, 136.7, 136.6, 130.8, 130.7, 130.6, 130.6, 130.1, 130.1, 129.9, 129.9, 129.9, 129.5, 127.2, 127.2, 127.1, 127.0, 126.5, 124.1, 21.1. ESI-HRMS (pos. detection mode): calcd for C60H42N6O2Ru m/z $[M]^{2+}$ 490.1215; found: 490.1201. Elemental analysis calcd for C60H42F12N6O2P2Ru (%): C, 56.74; H, 3.33; N, 6.62; found: C, 56.80; H, 3.24; N, 6.59.

[Ru(bphen)$_2$(Me-aminomethyl)](PF$_6$)$_2$ (10)

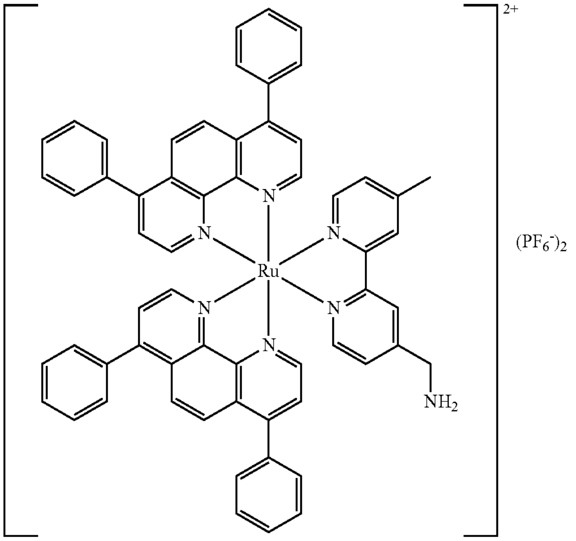

Ru(bphen)$_2$Cl$_2$ (200 mg, 1.0 equiv.) and 5-(aminomethyl)-2,2'-bipyridine (57 mg, 1.2 equiv.) were dissolved in a 1:1 mixture of $H_2O$/EtOH (10 mL) and were refluxed overnight under $N_2$ atmosphere. The solvent was evaporated and the residue redissolved in 10 mL of $H_2O$. A saturated, aq. $NH_4PF_6$ solution was added and the resulting precipitate was collected by vacuum filtration. The solid was washed with $H_2O$ (50 mL) and $Et_2O$ (50 mL). The product was dried in high vacuum. Yield: 88%. $^1$H-NMR ($CD_3CN$, 400 MHz): 8.59 (1H, d, J=1.3 Hz), 8.44 (1H, s), 8.29 (1H, d, J=5.5 Hz), 8.26 (1H, d, J=5.5 Hz), 8.15-8.07 (6H, m), 7.93 (1H, d, J=5.9 Hz), 7.74-7.70 (3H, m), 7.62-7.47 (22H, m), 7.39 (1H, dd, J=5.9, 1.7 Hz), 7.24 (1H, d, J=5.7 Hz), 4.38 (2H, s), 2.53 (3H, s). $^{13}$C-NMR ($CD_3CN$, 100 MHz): 158.4, 156.6, 152.9, 152.6, 152.5, 152.3, 151.8, 151.3, 149.5, 149.4, 149.4, 148.9, 148.7, 148.6, 142.9, 136.3, 136.2, 130.3, 130.2, 130.1, 123.0, 129.6, 129.5, 129.4, 129.4, 129.3, 127.4, 126.8, 126.7, 126.7, 126.4, 125.6, 124.5, 42.9, 20.8.

[Ru(bphen)$_2$(Me-maleimidemethyl)](PF$_6$)$_2$ (11)

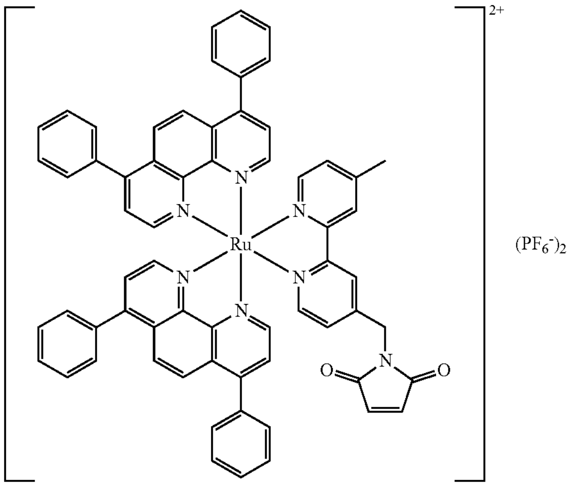

[Ru(bphen)$_2$(Me-aminomethyl)](PF$_6$)$_2$ (30 mg, 1.0 equiv.) and maleic anhydride (47 mg, 20.0 equiv.) were suspended in acetic acid (10 mL) under a nitrogen atmosphere. The mixture was refluxed for 10 h. The solution was then cooled down and a sat. aqueous solution of $NH_4PF_6$ was added. The crude product, which precipitated as a $PF_6$ salt, was collected by filtration and washed three times with $H_2O$ and $Et_2O$. The product was purified by column chromatography on silica gel with a $CH_3CN$/aq. $KNO_3$ (0.4 M) solution (10:1). The fractions containing the product were united and the solvent was removed. The residue was dissolved in $CH_3CN$ and undissolved $KNO_3$ was removed by filtration. The solvent was removed and the product was dissolved in $H_2O$. Upon addition of $NH_4PF_6$ the product precipitated as a $PF_6$ salt. The solid was obtained by centrifugation and was washed with $H_2O$ and $Et_2O$. Yield: 78%. $^1$H-NMR ($CD_3CN$, 400 MHz): 8.65 (1H, s), 8.57 (1H, d, J=1.3 Hz), 8.32 (1H, d, J=5.5 Hz), 8.29 (1H, d, J=5.5 Hz), 8.21-8.15 (6H, m), 8.11 (1H, d, J=5.5 Hz), 7.79-7.75 (3H, m), 7.69-7.56 (22H, m), 7.23 (2H, dd, J=5.8, 1.4 Hz), 6.90 (2H, s), 4.84 (2H, s), 2.57 (3H, s). $^{13}$C-NMR ($CD_3CN$, 100 MHz): 171.6, 158.5, 157.3, 153.0, 153.0, 152.9, 152.2, 151.5, 149.9, 149.9, 149.8, 149.4, 149.3, 149.2, 149.2, 149.1, 136.7, 136.6, 135.7, 130.7, 130.7, 130.5, 130.5, 130.0, 123.0, 129.8, 129.4, 127.1, 127.0, 126.9, 126.5, 126.2, 123.0, 40.6, 21.1. ESI-HRMS (pos. detection mode): calcd for $C_{64}H_{45}N_7O_2Ru$ [M-2PF$_6$]$^{2+}$ m/z 522.6334; found: 522.6347.

[Ru(bphen)$_2$(Me-maleimidemethyl)](Cl)$_2$ (12)

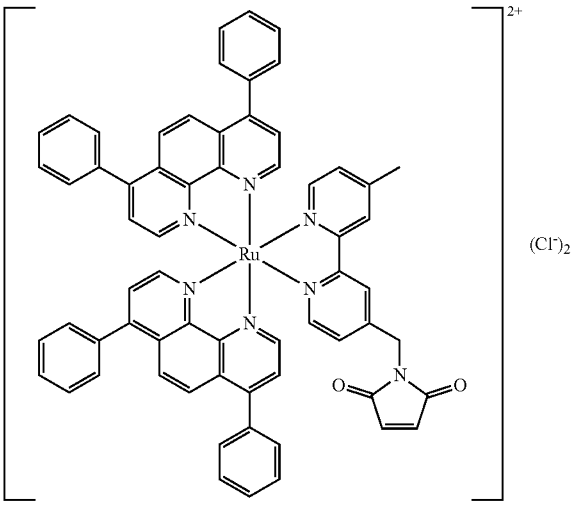

The counter ion $PF_6^-$ of compound 11 was exchanged to $Cl^-$ by elution with MeOH from the ion exchange resin Amberlite IRA-410 to afford compound 12.

Elemental analysis calcd for $C_{64}H_{46}Cl_2N_7O_2Ru$+$H_2O$ (%): C, 67.78; H, 4.18; N, 8.65; found: C, 67.73; H, 3.94; N, 8.36.

(4,4'-Dimethyl-2,2'-bipyridine)bis(4,7-diphenyl-1,10-phenanthroline)ruthenium(II) dichlorine [Ru(Me-bpy)(bphen)$_2$](Cl)$_2$ (13)

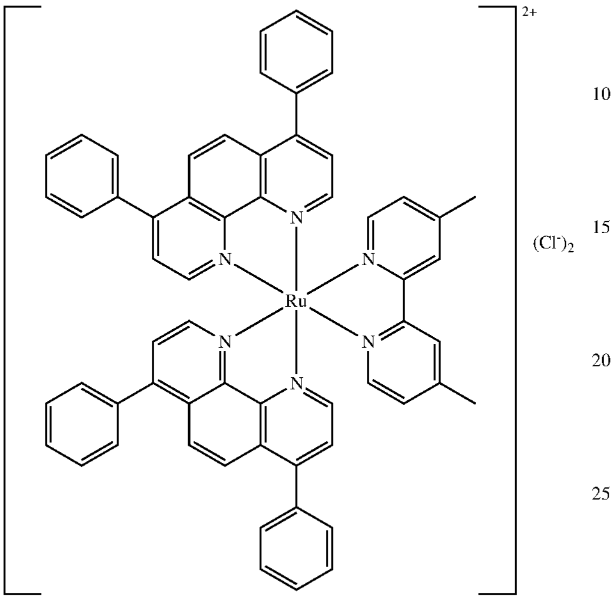

The synthesis of compound 13 is described in Mazuryk et al., 2014.

2) Photophysical Properties

Photophysical measurements were performed to evaluate the potential of the complexes of the invention 6 and 7 and the comparative examples as photosensitizers in PDT therapies.

Spectroscopic Measurements

The absorption of the samples in cuvettes has been measured with a Lambda 800 UV/VIS Spectrometer (PerkinElmer Instruments) and in 96 well plates with a SpectraMax M2 Spectrometer (Molecular Devices). The emission was measured by irradiation of the sample in fluorescence quartz cuvettes (width 1 cm) using a NT342B Nd-YAG pumped optical parametric oscillator (Ekspla) at 355 nm. Luminescence was focused and collected at right angle to the excitation pathway and directed to a Princeton Instruments Acton SP-2300i monochromator equipped with 1200 g/mm grating blazed at 500 nm. As a detector a XPI-Max 4 CCD camera (Princeton Instruments) has been used.

Results

At first, the absorption of the complexes in $CH_3CN$ was measured since the wavelengths used in PDT has a direct influence on the light penetration depth into the tissue and therefore influence the success of a treatment. All investigated complexes have a transition at about 263 nm for the phenanthroline-based complexes 1-5 and about 279 nm for the 4,7-diphenyl-1,10-phenanthroline-based complexes 6-7. Smaller bands varying from 280-320 nm (FIG. 1) were assigned to ligand centered (LC) transitions. Furthermore, these complexes have as the lowest energy absorption band a metal-to-ligand charge transfer (MLCT) transition. For the prototype complex, $[Ru(bipy)_3]^{2+}$, this band occurs at 450 nm, whereas this transition occurs for the complexes investigated in this study between 441 to 480 nm. Importantly, the compounds 5-7 have a long absorption tail towards the therapeutic spectral window.

Upon excitation at 355 nm, the emission of the complexes in $CH_3CN$ was determined. The maximum of the emission signal was measured between 600-710 nm (Table 1). Worthy of note, complexes 5 and 7 which showed the highest red shift of the MLCT transition, have also the highest emission maximum at 694-710 nm. This leads for all investigated complexes to a large Stokes shift implying minimal inference between excitation and luminescence.

TABLE 1

Spectroscopic properties of characterised complexes 1-7 in $CH_3CN$ at room temperature.

| Compound | UV/Vis λ / nm (ε / $M^{-1}$ $cm^{-1}$ * $10^{-3}$) | Emission $\lambda_{em}$ / nm |
|---|---|---|
| 1 | 200 (73.2), 225 (64.3), 264 (86.5), 284 (44.1), 446 (15.0) | 600 |
| 2 | 202 (77.9), 222 (61.5), 264 (81.7), 280 (43.9), 421 (12.8), 449 (13.9) | 606 |
| 3 | 201 (72.9), 223 (91.0), 263 (95.2), 289 (45.1), 388 (11.5), 441 (14.8) | 645 |
| 4 | 201 (100.1), 223 (91.3), 263 (105.8), 308 (28.2), 386 (13.8), 438 (16.7), 441 (16.8) | 654 |
| 5 | 201 (89.3), 224 (81.2), 265 (91.1), 379 (25.6), 458 (23.1) | 703 |
| 6 | 192 (183.4), 279 (126.3), 441 (23.2), 457 (23.2) | 623 |
| 7 | 192 (168.8), 280 (102.5), 371 (35.0), 465 (30.1) | 694 |

3) Singlet Oxygen Generation

Singlet Oxygen Measurements

Direct Evaluation

The samples were prepared in an air saturated $CH_3CN$ or $D_2O$ solution with an absorbance of 0.2 at 450 nm. This solution was irradiated in fluorescence quartz cuvettes (width 1 cm) using a mounted M450LP1 LED (Thorlabs) whose irradiation, centered at 450 nm, has been focused with aspheric condenser lenses. The intensity of the irradiation has been varied using a T-Cube LED Driver (Thorlabs) and measured with an optical power and energy meter. The emission signal was focused and collected at right angle to the excitation pathway and directed to a Princeton Instruments Acton SP-2300i monochromator equipped with 600 g/mm grating blazed at 1200 nm. A longpass glass filter was placed in front of the monochromator entrance slit to cut off light at wavelengths shorter than 850 nm. The slits for detection were fully open. As a detector an EO-817L IR-sensitive liquid nitrogen cooled germanium diode detector (North Coast Scientific Corp.) has been used. The singlet oxygen luminesce at 1270 nm was measured by recording spectra from 1100 to 1400 nm. For the data analysis, the singlet oxygen luminescence peaks at different irradiation intensities were integrated. The resulting areas were plotted against the percentage of the irradiation intensity and the slope of the linear regression calculated. The absorbance of the sample was corrected with an absorbance correction factor. As reference for the measurement in an $CH_3CN$ solution phenalenone ($\Phi_{phenaleone}$=0.95)[33] and for the measurement in a D2O solution $[Ru(bipy)_3]Cl_2$ ($\Phi_{Ru(bipy)3Cl2}$=0.22)[31] was used and the singlet oxygen quantum yields were calculated using the following formula:

$$\Phi_{sample} = \Phi_{reference} * \frac{S_{sample}}{S_{reference}} * \frac{I_{reference}}{I_{sample}}$$

-continued $$I = I_0 * (1 - 10^{-A})$$

Φ = singlet oxygen quantum yeild, $S$ = slope of the linear regression of the plot of the areas of the sign let oxyen luminescence peaks against their radiation intensity, $I$ = absorbance correction factor, $I0$ = light intensity of their radtion source, $A$ = absorbance of the sample at irradiation wavelength.

Indirect Evaluation

For the measurement in $CH_3CN$: The samples were prepared in an air-saturated $CH_3CN$ solution containing the complex with an absorbance of 0.1 at the irradiation wavelength, N,N-dimethyl-4-nitrosoaniline aniline (RNO, 24 μM) and imidazole (12 mM). For the measurement in PBS buffer: The samples were prepared in an air-saturated PBS solution containing the complex with an absorbance of 0.1 at the irradiation wavelength, N,N-dimethyl-4-nitrosoaniline aniline (RNO, 20 μM) and histidine (10 mM). The samples were irradiated on 96 well plates with an Atlas Photonics LUMOS BIO irradiator for different times. The absorbance of the samples was measured during these time intervals with a SpectraMax M2 Microplate Reader (Molecular Devices). The difference in absorbance (A0-A) at 420 nm for the $CH_3CN$ solution or at 440 nm a PBS buffer solution was calculated and plotted against the irradiation times. From the plot the slope of the linear regression was calculated as well as the absorbance correction factor determined. The singlet oxygen quantum yields were calculated using the same formulas as used for the direct evaluation.

Results

The investigation of the luminescence lifetimes of the complexes 1-7 in comparison between a degassed and air-saturated $CH_3CN$ solution showed that the excited state was able to interact with $^3O_2$. Additionally, the DFT calculations were able to characterize the lowest energy absorption band as a MLCT transition with a triplet state. With this in hand, a quantitative evaluation of singlet oxygen ($^1O_2$) was performed to assess the potential of the PSs in PDT, by two methods: 1) direct by measurement of the luminescence of $^1O_2$, 2) indirect by measurement of the variation in absorbance of a reporter molecule, as described above. In the first method, the efficiency of the production of $^1O_2$ was assessed by measuring its phosphorescence at 1270 nm. Worthy of note, the possibility of detection in this experiment is affected by its environment as well as the used setup. With the setup used in this study, we could only detect $\Phi(^1O_2)$ larger than 0.20 based on a low peak-to-noise ratio. In the second method (indirect method), $^1O_2$ is reacting with imidazole (in $CH_3CN$) and histidine (in PBS buffer) to a trans-annular peroxide adduct. This can further quench the absorbance of the reporter molecule p-nitrosodimethyl aniline (RNO), which has been monitored by UV/VIS spectroscopy. In both methods, the $^1O_2$ production has been compared with a reference molecule, namely a solution of phenalenone in $CH_3CN$ ($\Phi(^1O_2)_{phenaleone}$=0.95)[33] and a solution of $[Ru(bipy)_3]Cl_2$ in water $\Phi(^1O_2)_{Ru(bipy)3Cl2}$= 0.22)[31]. The results (Table 2) obtained show that the substitution of the bipyridine has an influence on the ability of the complexes to act as a photocatalyst. The $\Phi(^1O_2)$ in $CH_3CN$ using the direct and indirect method were found to be in the same range for complexes 1-4 and 6, namely between 0.53-0.69. In comparison, the values changed drastically in an aqueous solution. As an example, the $\Phi(^1O_2)$ for compound 3 and 6 in an aqueous environment was not detectable by the direct method and were determined to be 0.16 and 0.03, respectively by the indirect method. However, compounds 1-2 and 4 still showed a good singlet production with values between 0.23-0.46, as determined by direct and indirect method. These values are comparable with those previously reported for related compounds.[31-32] Additionally, the (E,E)-4,4'-bis(N,N'-dimethylaminovinyl)-2,2'-bipyridine substituted complexes 5 and 7 were investigated. As previously described in their excited state behaviour (emission, luminescence, lifetime) and anticipated by DFT calculations, these complexes showed different photophysical properties in comparison to the other complexes investigated in this work. They have untypically low $\Phi(^1O_2)$ values in $CH_3CN$ (0.22-0.35) for Ru(II) polypyridyl complexes. Subsequently, the $^1O_2$ production was also quite low in an aqueous environment.

TABLE 2

Singlet oxygen quantum yields ($\Phi(^1O_2)$) in $CH_3CN$ and aqueous solution determined by direct and indirect methods by excitation at 450 nm. Average of three independent measurements, +−10%.

| Compound | $CH_3CN$ Direct | $CH_3CN$ Indirect | $D_2O$ Direct | PBS indirect |
|---|---|---|---|---|
| 1 | 0.57 | 0.54 | 0.27 | 0.46 |
| 2 | 0.69 | 0.53 | 0.31 | 0.34 |
| 3 | 0.55 | 0.56 | n.d. | 0.16 |
| 4 | 0.62 | 0.59 | 0.25 | 0.26 |
| 5 | 0.24 | 0.30 | n.d. | 0.21 |
| 6 | 0.61 | 0.63 | n.d. | 0.03 |
| 7 | 0.22 | 0.35 | n.d. | 0.07 |

n.d. = not determinable, $\Phi(^1O_2) < 0.20$

4) Dark Cytotoxicity and (Photo-)Toxicity

Material and Methods

Cell Culture

HeLa and CT-26 cell lines were cultured in DMEM media (Gibco, Life Technologies, USA) supplemented with 10% of fetal calf serum (Gibco). U87 and U373 cell lines were cultured in MEM media with addition of 1% of MEM NEAA (non-essential aminoacids) (Gibco) and 10% of fetal calf serum. RPE-1 cells were cultured in DMEM/F-12 (Gibco) supplemented with 10% of fetal calf serum. RPE-1 stable cells lines were cultured as RPE-1 cells with addition of geneticin (0.5 mg/ml) (Gibco). All cell lines were complemented with 100 U/ml penicillin-streptomycin mixture (Gibco), and maintained in humidified atmosphere at 37° C. and 5% of $CO_2$.

Dark Cytotoxicity and (Photo-)Toxicity

Dark and light cytotoxicity of the Ru(II) complexes was assessed by fluorometric cell viability assay using resazurin (ACROS Organics). For dark and light cytotoxicity, cells were seeded in triplicates in 96 well plates at a density of 4000 cells per well in 100 μl, 24 h prior to treatment. The medium was then replaced with increasing concentration of the tested complexes and cells were incubated for 4 h. Medium was then replaced for fresh complete medium. Cells used for light cytotoxicity experiment were exposed to: 480 nm light for 10 min, 510 nm for 40 min, 540 for 60 min or 595 nm for 120 min in a 96-well plate using a LUMOS-BIO photoreactor (Atlas Photonics). Each well was individually illuminated with a LED at constant current. After irradiation cells were kept for another 44 h in the incubator and the medium was replaced by fresh complete medium containing resazurin (0.2 mg $ml^{-1}$ final concentration). After 4 h incubation at 37° C., the fluorescence signal of the resorufin product was read by SpectraMax M5 microplate reader (ex: 540 nm em: 590 nm). $IC_{50}$ values were calculated using GraphPad Prism software.

Having assessed that complexes 1-7 were producing $^1O_2$, the inventors then investigated their cytotoxicity in the dark and upon light irradiation. The potential of the complexes to act as PDT PSs was determined on mouse colon carcinoma cells (CT-26), human glioblastoma cells (U87 and U373), human cervical carcinoma cells (HeLa) as well as non-cancerous retina pigmented epithelial cell line (RPE-1) according to the method described above. The obtained results along with the calculated phototoxic index (PI) ($IC_{50}$ in the dark/$IC_{50}$ upon light irradiation) are gathered in Table 3. Ideally, a PDT PS should be non-toxic in the dark and highly toxic upon light activation. Promisingly, complexes 1-5 and 7 were found to be non-cytotoxic in all chosen cell lines in the dark ($IC_{50}$>100 μM). Compound 6 showed a slight cytotoxicity ($IC_{50}$ range from 3.09 to 28.77 μM) which is not detrimental for its use as photosensitizer. The toxicity of the compounds upon light irradiation (480 nm, 10 min, 3.21 J $cm^{-2}$) was then investigated. No or only poor toxicity was observed for comparative complexes 1-5 ($IC_{50}$ range from >100 to 52.54 μM). In contrast, complexes of the invention (6 and 7) showed a notable phototoxicity upon light irradiation (PI values range from 6.5 to 42.5). More importantly, both complexes showed potency in the treatment of the human glioblastomas (U87 and U373 cell lines). It is known that glioblastomas are difficult to treat and current therapies are not significantly improving the survival of patients (Lim, M., 2018).

To determine if complex 6 was efficiently killing cells when irradiated with longer wavelengths than 480 nm (i.e. closer to the biological window: 600-900 nm), we tested its ability to kill CT-26 mouse colon carcinoma cells at 510, 540 and 595 nm. Light irradiation of the treated cells at 510 nm (40 min) or 540 nm (60 min) caused phototoxic effect (PI values of 20.6 and 9.6, respectively). Even irradiation at 595 nm (2 h) generated toxicity in cells (PI value of 23.47). It has to be noted that the lack of $CO_2$ atmosphere during the 2 h irradiation also contributed to the obtained results (Table 4). Nevertheless, obtained PI value is reliable, dark control cells were also incubated for 2 h at 37° C. in non-$CO_2$ atmosphere. Overall, these results make compound 6 an impressive candidate as PDT PS.

TABLE 4

$IC_{50}$ values on CT-26 mouse colon carcinoma cells for complex 6 in the dark and upon light irradiation with wavelengths longer than 480 nm.

| | CT-26 | | |
|---|---|---|---|
| $IC_{50}$ [μM] | Dark | Light | PI |
| 510 nm 40 min | 4.18 ± 0.56 | 0.20 ± c0.005 | 20.6 |
| 540 nm 60 min | 3.27 ± 0.64 | 0.34 ± 0.005 | 9.6 |
| 595 nm 2 h | 1.408 ± 0.003 | 0.06 ± 0.004 | 23.47 |

5) In Vivo Biodistribution of Complex 6

Due to the very encouraging in vitro results obtained for compound 6, we have then tested its behavior in vivo.

Material and Methods

Twenty four, 8 week old healthy BALB/c female mice were used in this study. 0.015 mg/ml solution of complex 6 was prepared in Milli-Q water and filtrated (0.2 μm cellulose acetate membrane, VWR). For the introduction of solution of complex 6, IV injection was used (300 μl per mouse). Organ samples, including brain, liver, spleen, kidneys and lung, were collected from treated mice after 2 h, 6 h and 24 h post-injection. Each time six mice were sacrificed. Remaining six animals were used as a control.

Figure 2:
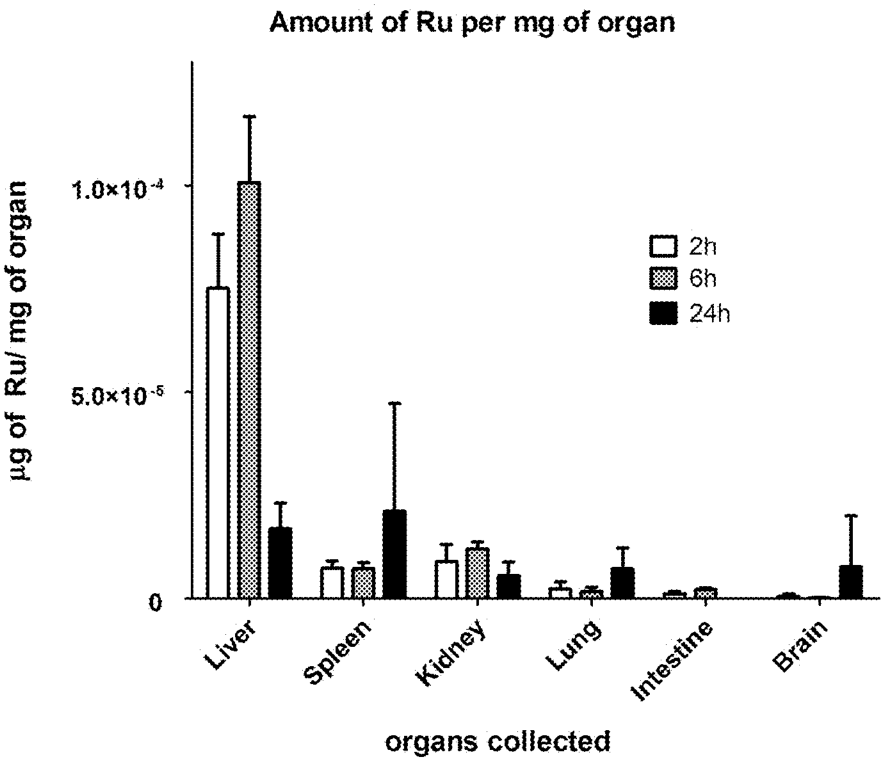
FIG. 2. Time-dependent biodistribution of complex 6 in organs of healthy BALB/c mice.

For these experiments, we have decided to use the chloride salt of the complex 6 to improve its solubility. The time-dependent biodistribution of this compound in different organs was determined in healthy 8-week-old BALB/c mice according to the above-described method. The amount of ruthenium in the tested samples was assessed using Inductive Coupled Plasma Mass-Spectrometry (ICP-MS). Worthy of note, the animals treated with compound 6 behave normally, without signs of pain, stress or discomfort. Blood analysis after 24 h treatment showed no sign of immune response compared to untreated control. As shown in FIG. 2, from all harvested organs, only liver had clearly increased levels of Ru after 6 h post IV injection. After 24 h, the amount of ruthenium in the liver decreased. This is a very promising result that could indicate that complex 6 is metabolized by the liver in living organisms.

6) Binding of Compounds 12 and 13 to Albumin

The following experiments have been carried out in order to demonstrate that compound 12, which bears a maleimide unit, is able to covalently bound to albumin and thus to form a conjugate.

TABLE 3

$IC_{50}$ values for the complexes 1-7 incubated with cell lines in the dark and upon light irradiation (480 nm, 10 min; 3.21 J $cm^{-2}$).

| | | Comparative complexes | | | | | Complexes of the invention | |
|---|---|---|---|---|---|---|---|---|
| $IC_{50}$/μM | | 1 | 2 | 3 | 4 | 5 | 6 | 7 |
| CT-26 | Dark | >100 | >100 | >100 | >100 | >100 | 3.09 ± 0.30 | 94.47 ± 7.38 |
| | Light | >100 | 91.24 ± 7.54 | 85.71 ± 9.47 | 72.59 ± 7.44 | 52.54 ± 6.04 | 0.19 ± 0.04 | 6.62 ± 0.70 |
| | PI | — | >1 | >1 | >1 | >2 | 16.3 | 14.3 |
| U87 | Dark | >100 | >100 | >100 | >100 | >100 | 28.45 ± 1.97 | >100 |
| | Light | 93.68 ± 2.50 | 71.40 ± 7.54 | >100 | >100 | >100 | 0.67 ± 0.13 | 7.90 ± 0.54 |
| | PI | >1 | >1 | — | — | — | 42.5 | >12.7 |
| U373 | Dark | >100 | >100 | >100 | >100 | >100 | 23.37 ± 0.53 | >100 |
| | Light | >100 | >100 | >100 | >100 | >100 | 1.89 ± 0.07 | 14.85 ± 0.81 |
| | PI | — | — | — | — | — | 12.37 | >6.7 |
| HeLa | Dark | >100 | >100 | >100 | >100 | >100 | 13.57 ± 1.30 | >100 |
| | Light | >100 | >100 | >100 | >100 | >100 | 0.61 ± 0.06 | 15.21 ± 1.29 |
| | PI | — | — | — | — | — | 22.2 | >6.5 |
| RPE-1 | Dark | >100 | >100 | >100 | >100 | >100 | 28.77 ± 0.94 | >100 |
| | Light | >100 | >100 | >100 | >100 | >100 | 0.825 ± 0.03 | 8.95 ± 0.50 |
| | PI | — | — | — | — | — | 34.9 | >11.2 |

Material and Method

UV-visible (UV-Vis) spectrophotometry was monitored on an Agilent Cary 8454 diode array spectrophotometer in the wavelength range between 190 and 1100 nm.

Figure 3:
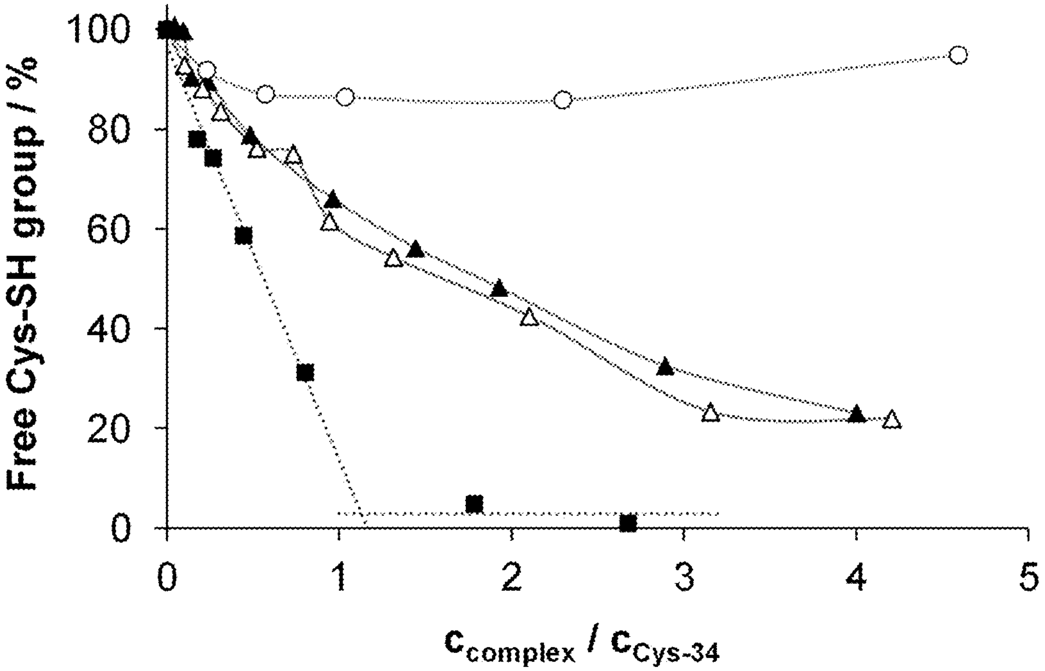
FIG. 3. Free Cys-34 SH content of HSA at various complex 12-HSA ratios (closed triangle, open triangle, closed square) and various conditions: 3 h incubation (open triangle), 0.5 h incubation (closed triangle) and 0.5 h incubation in the presence of 0.5% SDS (closed square). The effect of a ruthenium complex without a maleimide function (complex 13) was also tested as negative control (open circle).

Interaction of complex 12 at the Cys-34 residue of HSA was investigated spectrophotometrically via the dithiodipyridine (DTDP) method described previously (Pichler et al., 2013). The available Cys-thiol content in HSA was determined to be 22%. Complex binding was tested in the following setup: 133 μM HSA (29 μM free thiol) and various amounts of complex (0-120 μM) were incubated for 3 h or 30 min at pH=7.00 (PBS). A first series of UV-Vis spectra (a) were recorded before addition of 110 μM DTDP and a second series of UV-Vis spectra (b) were recorded after addition of 110 μM DTDP and after another 40 min waiting. Cys-34 residues of HSA which are not conjugated to complex 12 react with DTDP to form the UV active compound 2-thiopyridone. Blank experiment with compound 13 was carried out as well as a control experiment. The effect of protein unfolding on the thiol binding of complex 12 was studied by the addition of 0.5% (m/m) SDS to the protein prior to its reaction with the complex. This experiment allows to determine the amount of free Cys-34 residue of HSA as a function of the added equivalent of the complexes. The results of this experiment are presented on FIG. 3).

Results

Complex 13 applied as negative control, affects barely the quantity of free thiol groups. Complex 12, on the other hand, interacts in a significant extent with Cys-34. Incubation of the complex with HSA for 3 h (open triangle) or 30 min (closed triangle) did not result in remarkable differences, at the same time the interaction with the native protein does not show quantitative binding at this site. Measurements implemented with the unfolded protein using 0.5% SDS as denaturing agent revealed nearly quantitative interaction between 12 and the Cys-34 thiol group of HSA. Two scenarios are possible regarding the interaction with native protein: (i) concurrent binding at other sites in HSA reduces the effective concentration of 12, or (ii) structural heterogeneity applies in the HSA stock, i.e. the availability of thiol groups for 12 is different. First interpretation does not fit to thermodynamic considerations (irreversible binding at Cys-34 should be preferred over intermolecular interactions), while the second assumption can explain the elevated saturation phase of the curves, but not their relatively low slope.

All in all, complex 12 was found to interact with the Cys-34 thiol group of HSA, although the interaction is not quantitative.

REFERENCES

S. Monro, K. L. Colón, H. Yin, J. Roque, P. Konda, S. Gujar, R. P. Thummel, L. Lilge, C. G. Cameron, S. A. McFarland, *Chem. Rev.* 2019, 119, 797-828.

F. W. Heinemann, J. Karges, G. Gasser Acc. *Chem. Res.* 2017, 50, 2727-2736.

F. E. Poynton, S. A. Bright, S. Blasco, D. C. Williams, J. M. Kelly, T. Gunnlaugsson, *Chem. Soc. Rev.* 2017, 46, 7706-7756.

G. Shi, S. Monro, H. R., J. Colpitts, J. Fong, K. Kasimova, H. Yin, R. DeCoste, C. Spencer, L. Chamberlain, A. Mandel, L. Lilge, S. A. McFarland, *Coord. Chem. Rev.* 2014, 282-283, 127-138.

Sullivan, B.; Salmon, D.; Meyer, T., *Inorg. Chem.* 1978, 17 (12), 3334-3341.

Duong, A.; Maris, T.; Lebel, O.; Wuest, J. D., *The Journal of organic chemistry* 2011, 76 (5), 1333-1341.

Maury, O.; Guégan, J.-P.; Renouard, T.; Hilton, A.; Dupau, P.; Sandon, N.; Toupet, L.; Le Bozec, H. *New J. Chem.* 2001, 25 (12), 1553-1566.

Mari, C.; Pierroz, V.; Leonidova, A.; Ferrari, S.; Gasser, G. *Eur. J. Inorg. Chem.* 2015, 2015 (23), 3879-3891.

Crosby, G.; Elfring Jr, W., *The Journal of Physical Chemistry* 1976, 80 (20), 2206-2211.

Jones Jr, W. E.; Smith, R. A.; Abramo, M. T.; Williams, M. D.; Van Houten, *J. Inorg. Chem.* 1989, 28 (12), 2281-2285.

Mazuryk, O.; Magiera, K.; Rys, B.; Suzenet, F.; Kieda, C.; Brindell, M., *JBIC Journal of Biological Inorganic Chemistry* 2014, 19 (8), 1305-1316.

Nakamaru, K., *Bull. Chem. Soc. Jpn.* 1982, 55 (5), 1639-1640.

Ishida, H.; Tobita, S.; Hasegawa, Y.; Katoh, R.; Nozaki, K., *Coord. Chem. Rev.* 2010, 254 (21-22), 2449-2458.

Nakamaru, K., *Bull. Chem. Soc. Jpn.* 1982, 55 (9), 2697-2705.

Lim, M.; Xia, Y.; Bettegowda, C.; Weller, M., *Nature Reviews Clinical Oncology* 2018, 15 (7), 422-442.

Poynton, F. et al. *Chem. Soc. Rev.,* 2017, 46, p. 7706-7756.

CN 109 233 547.

CN 109 535 066.

Lomzik, M. et al., *Journal of Inorganic Biochemistry* 2017, 175, 80-91.

Caspar, R. et al., *Inorganic chemistry,* 2006, 45, 4071-4078.

Brennan et al. *Langmuir,* 2006, p. 10754-10761.

Pichler et al., *Chem. Commun.* 2013, 49, p. 2249-2251.

The invention claimed is:

1. A method of photodynamic therapy comprising administering to an animal or a human in need thereof an effective amount of a compound selected from the group consisting of:

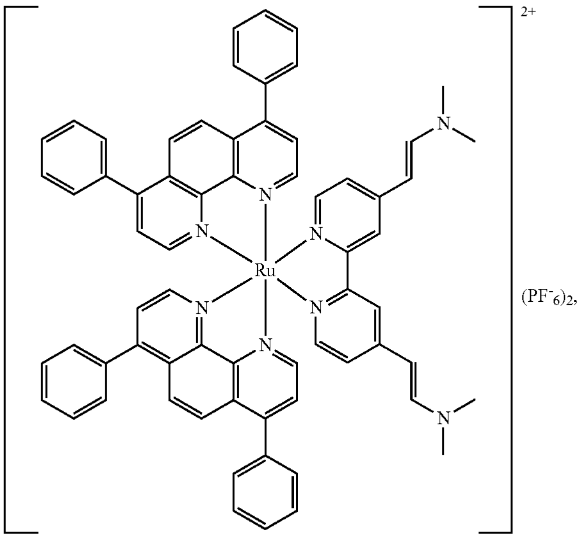

-continued

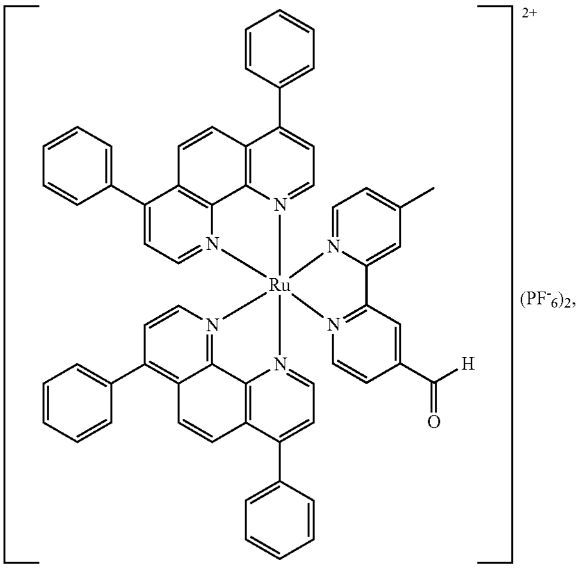

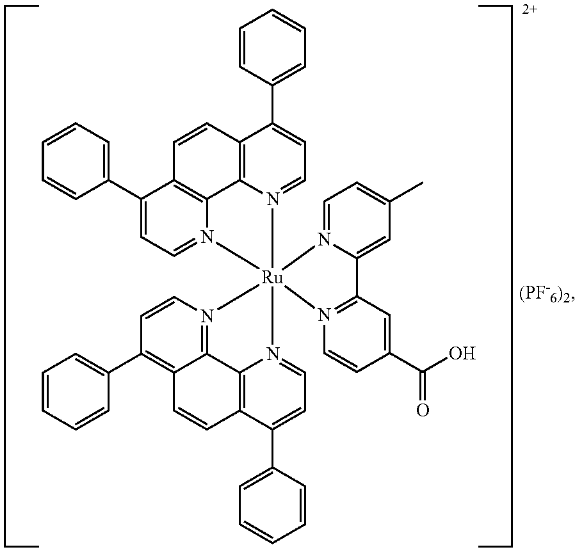

-continued

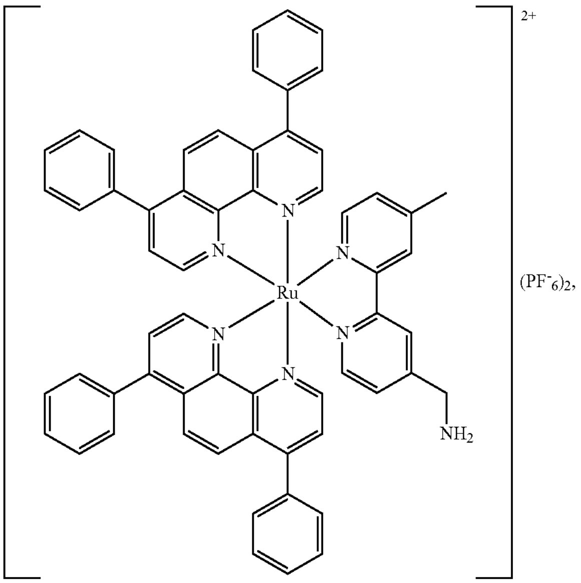

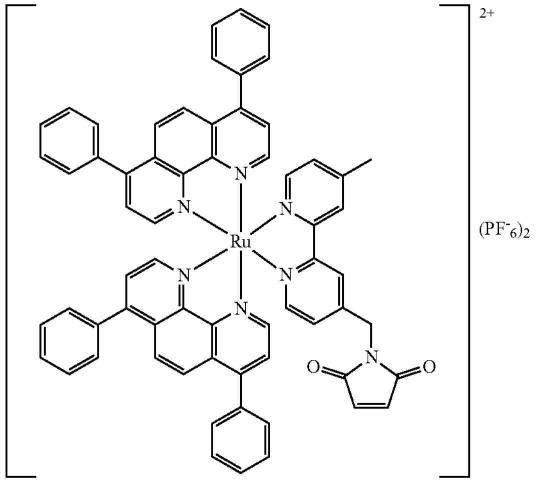

and the pharmaceutically acceptable salts and/or solvates thereof.

2. The method according to claim 1, wherein the photodynamic therapy is intended to treat a disease selected from the group consisting of a cancer, a bacterial infection, a fungal infection, a viral infection, and a skin disorder.

3. The method according to claim 2, wherein the cancer is a lung cancer, a bladder cancer, an esophageal cancer, a colon cancer, a stomach cancer, a liver cancer, a skin cancer, an ovarian cancer, a pancreatic cancer, a head and neck cancer, or a brain cancer; the bacterial infection is a sinusitis, a diabetic foot, or a burned wound; the fungal infection is a mycosis; the viral infection is herpes; and the skin disorder is acne, or a port wine stain.

* * * * *